United States Patent
Wu

(10) Patent No.: US 8,182,809 B1
(45) Date of Patent: May 22, 2012

(54) METHODS FOR TREATING CANCER BY INHIBITING MIC SHEDDING

(75) Inventor: Jennifer D. Wu, Seattle, WA (US)

(73) Assignee: University of Washington, Seattle, WA (US)

(*) Notice: Subject to any disclaimer, the term of this patent is extended or adjusted under 35 U.S.C. 154(b) by 138 days.

(21) Appl. No.: 12/555,194

(22) Filed: Sep. 8, 2009

Related U.S. Application Data

(60) Provisional application No. 61/095,004, filed on Sep. 8, 2008, provisional application No. 61/153,412, filed on Feb. 18, 2009.

(51) Int. Cl.
*A61K 39/00* (2006.01)
*A61K 39/395* (2006.01)

(52) U.S. Cl. ............ 424/130.1; 424/139.1; 424/141.1; 424/155.1

(58) Field of Classification Search ............ 424/141.1, 424/172.1, 136.1
See application file for complete search history.

(56) References Cited

U.S. PATENT DOCUMENTS

| | | | | |
|---|---|---|---|---|
| 6,852,318 | B1* | 2/2005 | Varner | 424/130.1 |
| 2003/0105000 | A1* | 6/2003 | Pero et al. | 514/12 |
| 2007/0248607 | A1* | 10/2007 | Spies et al. | 424/141.1 |

OTHER PUBLICATIONS

Gura (Science, 1997, 278:1041-1042).*
Kaiser (Science, 2006, 313: 1370).*
Rudikoff et al, (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444, see abstract in particular).*
Burgess et al (J of Cell Bio. 111:2129-2138, 1990).*
Busche et al., "Natural Killer Cell-mediated Rejection of Experimental Human Lung Cancer by Genetic Overexpression of Major Histocompatibility Complex Class I Chain-related Gene A," Hum Gene Ther 17: 135-46 (2006).
Carayannopoulos et al., "Cutting Edge: Murine UL16-binding Protein-like Transcript 1: A Newly Described Transcript Encoding a High-affinity Ligand for Murine NKG2D," J Immunol 169: 4079-83 (2002).
Cerwenka et al., "Ectopic Expression of Retinoic Acid Early Inducible-1 Gene (RAE-1) Permits Natural Killer Cell-mediated Rejection of a MHC Class I-bearing Tumor in Vivo," Proc Natl Acad Sci U S A 98: 11521-6 (2001).
Cerwenka et al., "NKG2D Ligands: Unconventional MHC Class I-like Molecules Exploited by Viruses and Cancer," Tissue Antigens 61: 335-43 (2003).
Cerwenka et al., "Retinoic Acid Early Inducible Genes Define a Ligand Family for the Activating NKG2D Receptor in Mice," Immunity 12: 721-7 (2000).
Diefenbach et al., "A Novel Ligand for the NKG2D Receptor Activates NK Cells and Macrophages and Induces Tumor Immunity," Eur J Immunol 33: 381-91 (2003).
Diefenbach et al., "Rae1 and H60 Ligands of the NKG2D Receptor Stimulate Tumour Immunity," Nature 413: 165-71 (2001).
Doubrovina et al., "Evasion from NK Cell Immunity by MHC Class I Chain-related Molecules Expressing Colon Adenocarcinoma," J Immunol 171:6891-9 (2003).
Friese et al., "MICA/NKG2D-mediated Immunogene Therapy of Experimental Gliomas," Cancer Res 63: 8996-9006 (2003).
Groh et al., "Broad Tumor-associated Expression and Recognition by Tumor-derived Gamma Delta T Cells of MICA and MICB," Proc Natl Acad Sci U S A 96:6879-84 (1999).
Groh et al., "Tumour-derived Soluble MIC Ligands Impair Expression of NKG2D and T-cell Activation," Nature 419: 734-8 (2002).
Holdenrieder et al., "Soluble MICA in Malignant Diseases," Int J Cancer 118: 684-7 (2006).
Jinushi et al., "Expression and Role of MICA and MICB in Human Hepatocellular Carcinomas and Their Regulation by Retinoic Acid," Int J Cancer 104: 354-61 (2003).
Long, E.O., "Tumor Cell Recognition by Natural Killer Cells," Semin Cancer Biol 12: 57-61 (2002).
Marten et al., "Soluble MIC is Elevated in the Serum of Patients with Pancreatic Carcinoma Diminishing Gamma Delta T Cell Cytotoxicity," Int J Cancer 119:2359-65 (2006).
Rafaghello et al., Neoplasia 6: 558-68 (2004). "Downregulation and/or Release of NKG2D Ligands as Immune Evasion Strategy of Human Neuroblastoma."
Raulet, D.H., "Roles of the NKG2D Immunoreceptor and its Ligands," Nat Rev Immunol 3: 781-90 (2003).
Salih et al., "Down-Regulation of MICA on Human Tumors by Proteolytic Shedding," J Immunol 169: 4098-102 (2002).
Smyth et al., "NKG2D Function Protects the Host from Tumor Initiation," J Exp Med 202: 583-8 (2005).
Vetter et al., "Expression of Stress-induced MHC Class I Related Chain Molecules on Human Melanoma," J Invest Dermatol 118: 600-5 (2002).
Wu et al., "Prevalent Expression of the Immunostimulatory MHC Class I Chain-related Molecule is Counteracted by Shedding in Prostate Cancer," J Clin Invest 114: 560-8 (2004).

* cited by examiner

*Primary Examiner* — Peter J Reddig
*Assistant Examiner* — Yan Xiao
(74) *Attorney, Agent, or Firm* — Mark J. FitzGerald; Nixon Peabody LLP

(57) ABSTRACT

Described herein are compositions and methods for treating cancer, comprising administering to an individual having cancer an agent to prevent MIC shedding (initiated at the alpha-3 ectodomain of MIC) by a tumor cell. Also provided herein are screening assays for identifying, or testing the efficacy of, an agent for increasing sensitivity of a tumor to immune cell-mediated killing.

6 Claims, 33 Drawing Sheets

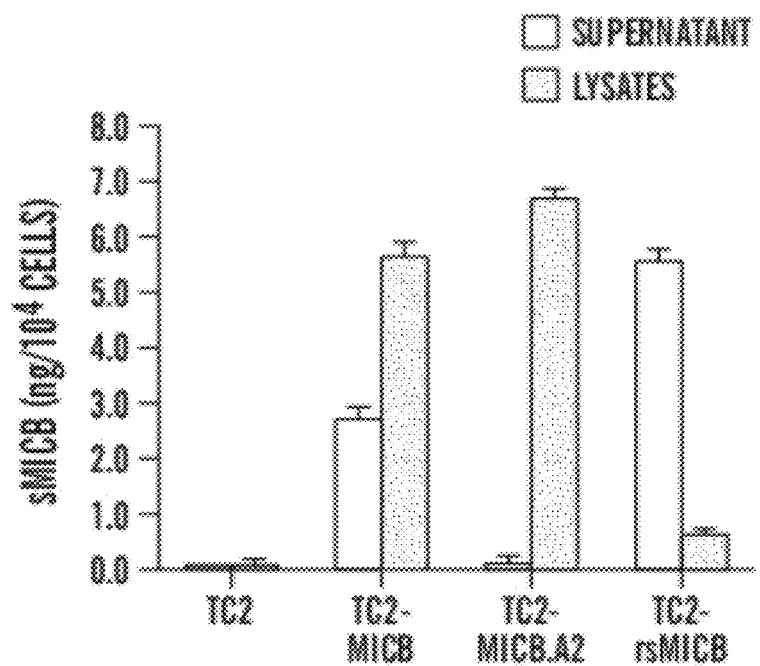
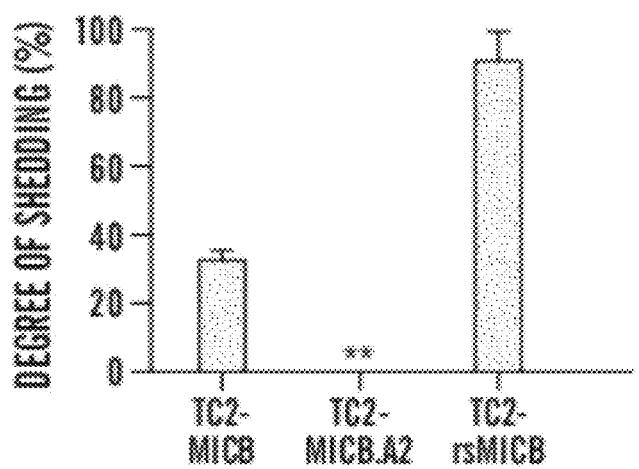
FIG. 2C

151 MKVKTHVHAMHADCLQELRRYLKSGVVLRRTVPPMVNVTRSEASEGNITV
201 TCRASGFYPWNITLSWR...
251 ...KVLVLQSHWQTFHVS AVAAAAIFVI
FIG. 7B
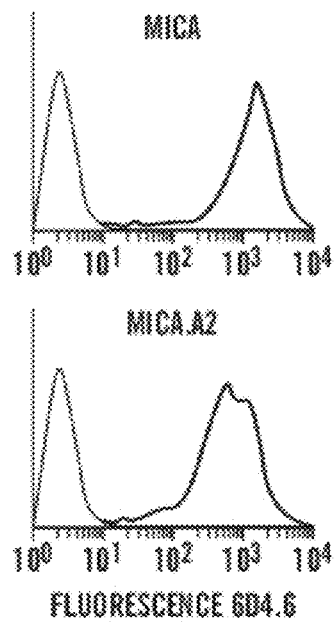
FIG. 7C
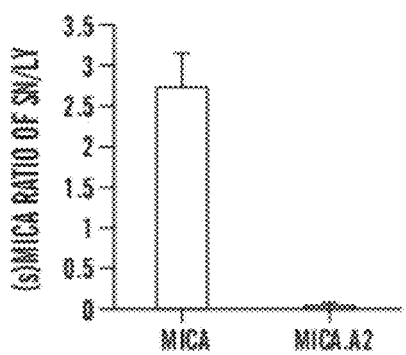
FIG. 7D

| Sequence | designation | shedding |
|---|---|---|
| EDQTQDTELV-ETRPAGDGTFQKWAAVVVPSGQEQRY | HLA-A2 | |
| VSLSHDTQQWGDVLPDGNGTYQTWVATRICQGEEQRF | wtMICA | |
| EDQTQDTELV-ETRPA | M1 | + |
| ---------------------VPSGQEQRY | M2 | + |
| -----------------DGTFQKWAAVV------------ | M3*** | + |
| -----------------DGTFQKWA--------------- | M4*** | |
| -----------------DGTFQK----------------- | M5* | |
| -----------------DGTFQ------------------ | M6 | |
| --------------------FQKSAAVV------------ | M7* | + |
| ---------------------QKSAAVV------------ | M8 | |
| --------------------FQKSAAV------------- | M9 | + |
| ---------------------------F----------- | M10 | + |
| ---------------------------A----------- | M11 | + |
| ---------------------------K----------- | M12 | + |

* sdMICA-TRAMP-C2    QDGVSLSHDTQQWGDVLPDGNGTYQT
                   QDGVSLSHDTQQWGDVLPDGNGTYQTW
                   FTCYME**
                   FTCYMEHSGNHSTHPVP sdMICA-C1R         QDGVSLSHDTQQWGDVLPDGNGTYQT
                   QDGVSLSHDTQQWGDVLPDGNGTYQTW
                   FTCYME**
                   FTCYMEHSGNHSTHPVP

Control rsMICA     QDGVSLSHDTQQWGDVLPDGNGTYQT
                   QDGVSLSHDTQQWGDVLPDGNGTYQTW
                   FTCYMEHSGNHSTHPVP

FIG. 10A

...RTCQGEEQRFTCYMEHSGNHSTHPVPSGKVLVLQSHWQTFHVSAVAAA... — TM
α3 domain

...RTCQGEEQRFTCYMEHSGNHSTHPVPSGKVLVLQSHWQTFHVSAVAAA... — TM
α3 domain

```
151 MKTKTHYHAMHADCLQELRRYLKSGVVLRRTVPPMVNVTRSEASEGNITV
201 TCRASGFYPWNITLSWRQDGVSLSHDTQQWGDVLPDGNGTYQTWVATRICQGEEQRF
251 CYMEHSGNHSTHPVPSGKVLVLQSHWQTFHVSAVAAAIFVI
                                        TM
```
α3

FIG. 13B

| Sequence | designation | shedding |
|---|---|---|
| 211 EDQTQDTELV-ETRPAGDGTFQKWAAVVVPSGQEQRY | HLA-A2 | |
| | | |
| 211 VSLSHDTQQWGDVLPDGNGTYQTWVATRICQGEEQRF | wtMICA | + |
| EDQTQDTELV-ETRPAGICTYQTWVATRICQGEEQRF | MICA-M1 | + |
| VSLSHDTQQWGDVLPDGNGTYQTWVATRVPSGQEQRY | MICA-M2 | + |
| VSLSHDTQQWGDVLPDGDGTFQKWAAVVICQGEEQRF | MICA-M3 | . |
| VSLSHDTQQWGDVLPDGDGTFQKWAATRICQGEEQRF | MICA-M4 | . |
| VSLSHDTQQWGDVLPDGDGTFQKWVATRICQGEEQRF | MICA-M5 | . |
| VSLSHDTQQWGDVLPDGDGTFQTWVATRICQGEEQRF | MICA-M6 | + |
| VSLSHDTQQWGDVLPDGNGTYQAWVATRICQGEEQRF | MICA-M11 | + |

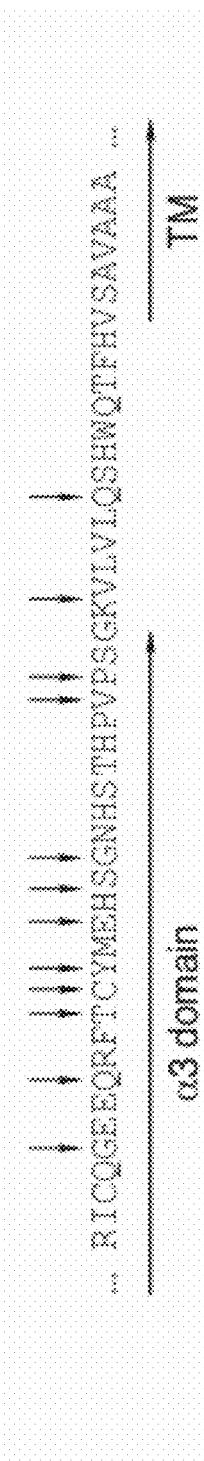
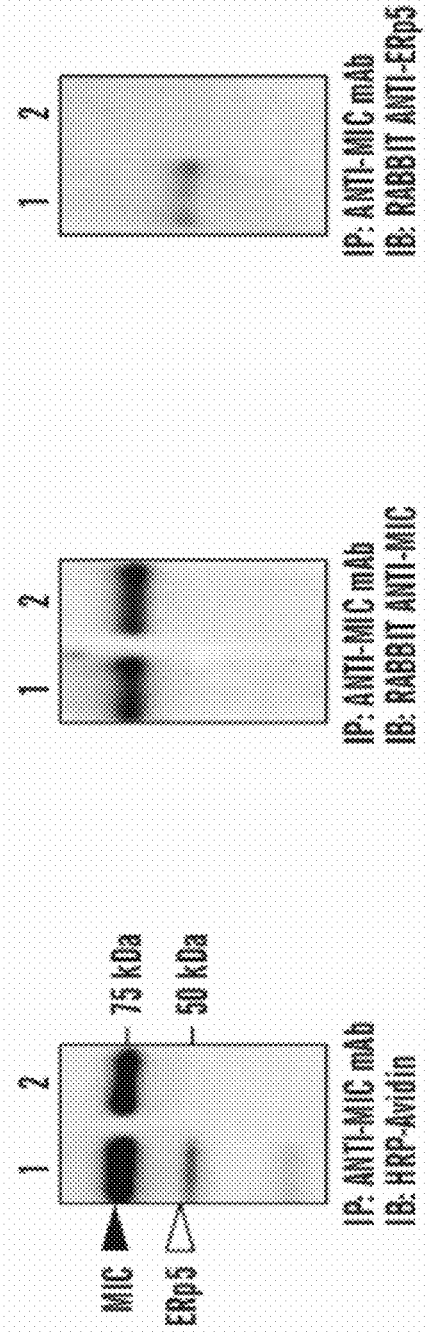
FIG. 15A
FIG. 15B
FIG. 15C
FIG. 15D

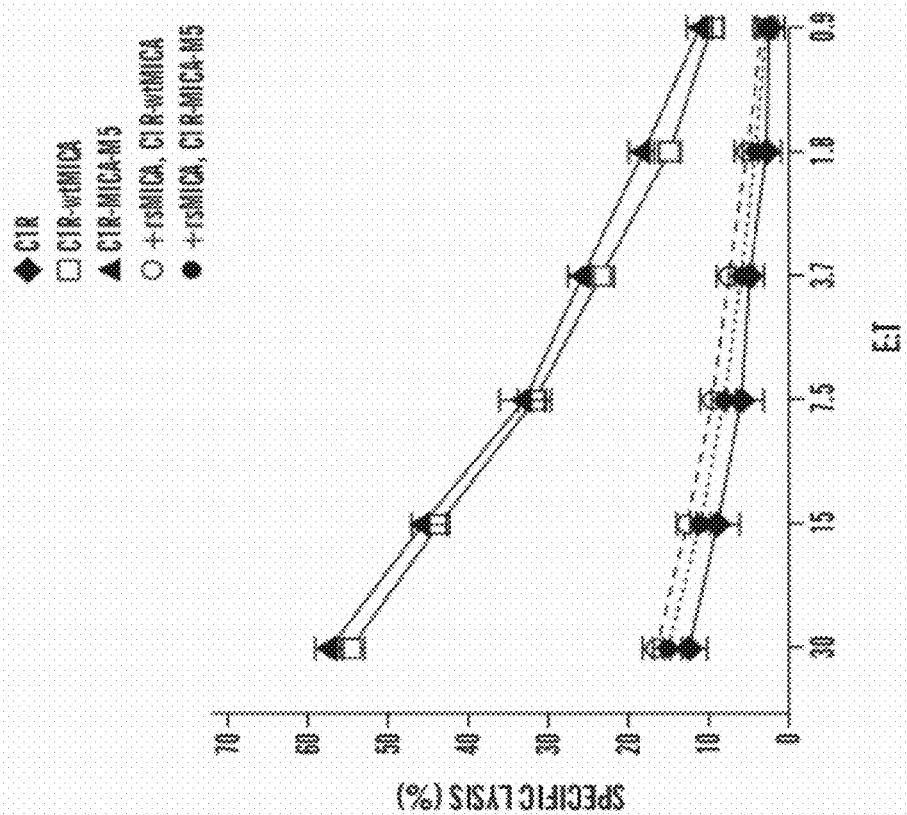
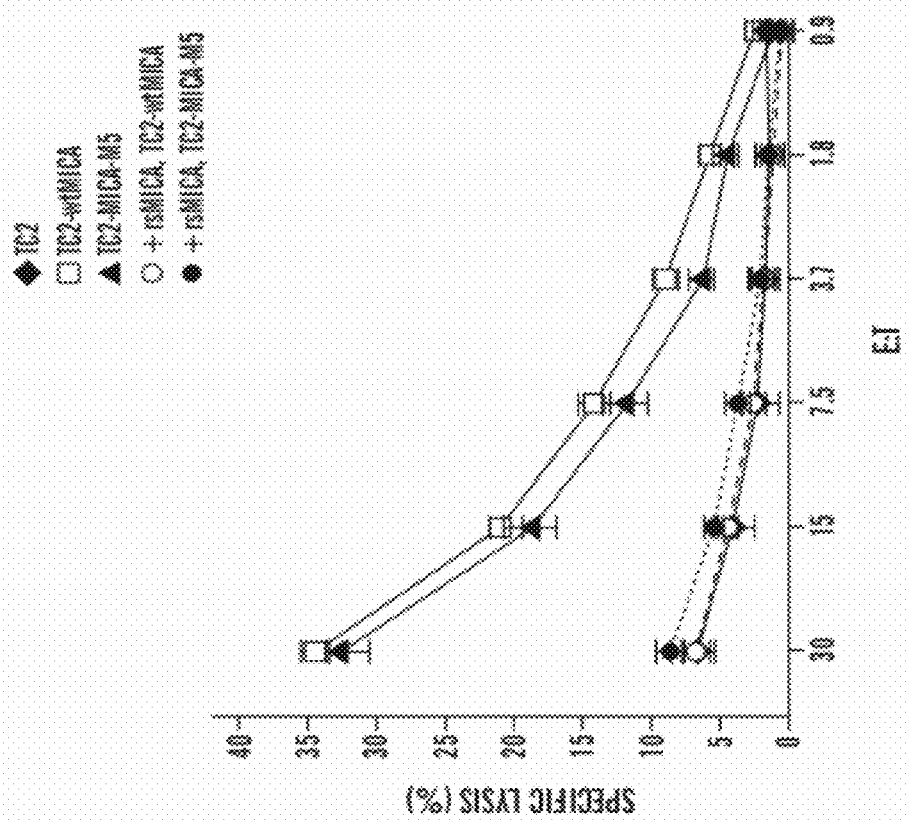
FIG. 16B

FIG. 19

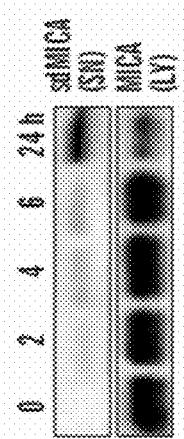
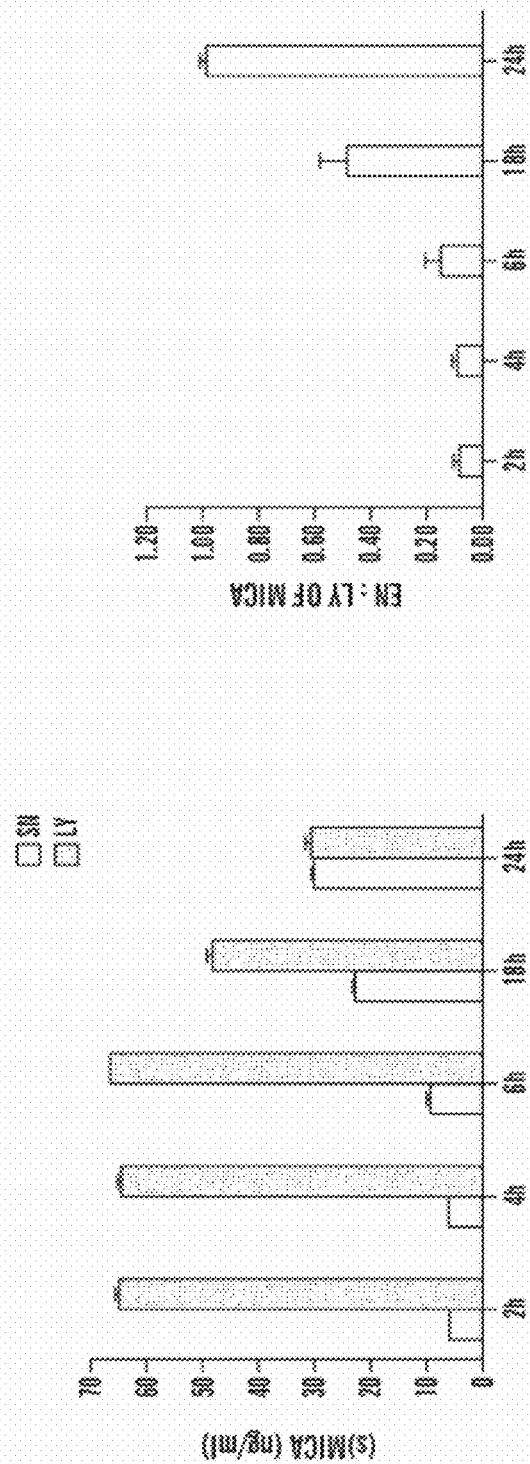

SEQUENCE LISTING

```
<160> NUMBER OF SEQ ID NOS: 116

<210> SEQ ID NO 1
<211> LENGTH: 6
<212> TYPE: PRT
<213> ORGANISM: Homo sapiens
```

```
<400> SEQUENCE: 1

Asn Gly Thr Tyr Gln Thr
1               5

<210> SEQ ID NO 2
<211> LENGTH: 8
<212> TYPE: PRT
<213> ORGANISM: Homo sapiens

<400> SEQUENCE: 2

Tyr Gln Thr Trp Val Ala Thr Arg
1               5

<210> SEQ ID NO 3
<211> LENGTH: 22
<212> TYPE: PRT
<213> ORGANISM: Homo sapiens

<400> SEQUENCE: 3

Thr Gln Gln Trp Gly Asp Val Leu Pro Asp Gly Asn Gly Thr Tyr Gln
1               5                  10                  15

Thr Trp Val Ala Thr Arg
            20

<210> SEQ ID NO 4
<211> LENGTH: 7
<212> TYPE: PRT
<213> ORGANISM: Homo sapiens

<400> SEQUENCE: 4

Gln Thr Trp Val Ala Thr Arg
1               5

<210> SEQ ID NO 5
<211> LENGTH: 4
<212> TYPE: PRT
<213> ORGANISM: Homo sapiens

<400> SEQUENCE: 5

Thr Trp Val Ala
1

<210> SEQ ID NO 6
<211> LENGTH: 440
<212> TYPE: PRT
<213> ORGANISM: Homo sapiens

<400> SEQUENCE: 6

Met Ala Leu Leu Val Leu Gly Leu Val Ser Cys Thr Phe Phe Leu Ala
1               5                  10                  15

Val Asn Gly Leu Tyr Ser Ser Ser Asp Asp Val Ile Glu Leu Thr Pro
            20                  25                  30

Ser Asn Phe Asn Arg Glu Val Ile Gln Ser Asp Ser Leu Trp Leu Val
        35                  40                  45

Glu Phe Tyr Ala Pro Trp Cys Gly His Cys Gln Arg Leu Thr Pro Glu
    50                  55                  60

Trp Lys Lys Ala Ala Thr Ala Leu Lys Asp Val Val Lys Val Gly Ala
65                  70                  75                  80

Val Asp Ala Asp Lys His His Ser Leu Gly Gly Gln Tyr Gly Val Gln
                85                  90                  95

Gly Phe Pro Thr Ile Lys Ile Phe Gly Ser Asn Lys Asn Arg Pro Glu
                100                 105                 110
```

-continued

Asp Tyr Gln Gly Gly Arg Thr Gly Glu Ala Ile Val Asp Ala Ala Leu
            115                 120                 125

Ser Ala Leu Arg Gln Leu Val Lys Asp Arg Leu Gly Arg Ser Gly
        130                 135                 140

Gly Tyr Ser Ser Gly Lys Gln Gly Arg Ser Asp Ser Ser Lys Lys
145                 150                 155                 160

Asp Val Ile Glu Leu Thr Asp Asp Ser Phe Asp Lys Asn Val Leu Asp
                165                 170                 175

Ser Glu Asp Val Trp Met Val Glu Phe Tyr Ala Pro Trp Cys Gly His
            180                 185                 190

Cys Lys Asn Leu Glu Pro Glu Trp Ala Ala Ala Ser Glu Val Lys
        195                 200                 205

Glu Gln Thr Lys Gly Lys Val Lys Leu Ala Ala Val Asp Ala Thr Val
        210                 215                 220

Asn Gln Val Leu Ala Ser Arg Tyr Gly Ile Arg Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270

Ala Pro Pro Pro Glu Leu Leu Glu Ile Ile Asn Glu Asp Ile Ala Lys
        275                 280                 285

Arg Thr Cys Glu Glu His Gln Leu Cys Val Val Ala Val Leu Pro His
        290                 295                 300

Ile Leu Asp Thr Gly Ala Ala Gly Arg Asn Ser Tyr Leu Glu Val Leu
305                 310                 315                 320

Leu Lys Leu Ala Asp Lys Tyr Lys Lys Lys Met Trp Gly Trp Leu Trp
                325                 330                 335

Thr Glu Ala Gly Ala Gln Ser Glu Leu Glu Thr Ala Leu Gly Ile Gly
            340                 345                 350

Gly Phe Gly Tyr Pro Ala Met Ala Ala Ile Asn Ala Arg Lys Met Lys
        355                 360                 365

Phe Ala Leu Leu Lys Gly Ser Phe Ser Glu Gln Gly Ile Asn Glu Phe
        370                 375                 380

Leu Arg Glu Leu Ser Phe Gly Arg Gly Ser Thr Ala Pro Val Gly Gly
385                 390                 395                 400

Gly Ala Phe Pro Thr Ile Val Glu Arg Glu Pro Trp Asp Gly Arg Asp
                405                 410                 415

Gly Glu Leu Pro Val Glu Asp Asp Ile Asp Leu Ser Asp Val Glu Leu
            420                 425                 430

Asp Asp Leu Gly Lys Asp Glu Leu
        435                 440

<210> SEQ ID NO 7
<211> LENGTH: 150
<212> TYPE: PRT
<213> ORGANISM: Homo sapiens

<400> SEQUENCE: 7

Met Lys Thr Lys Thr His Tyr His Ala Met His Ala Asp Cys Leu Gln
1               5                   10                  15

Glu Leu Arg Arg Tyr Leu Lys Ser Gly Val Val Leu Arg Arg Thr Val
            20                  25                  30

Pro Pro Met Val Asn Val Thr Arg Ser Glu Ala Ser Glu Gly Asn Ile
        35                  40                  45

```
Thr Val Thr Cys Arg Ala Ser Gly Phe Tyr Pro Trp Asn Ile Thr Leu
        50                  55                  60
Ser Trp Arg Gln Asp Gly Val Ser Leu Ser His Asp Thr Gln Gln Trp
 65                  70                  75                  80
Gly Asp Val Leu Pro Asp Gly Asn Gly Thr Tyr Gln Thr Trp Val Ala
                85                  90                  95
Thr Arg Ile Cys Gln Gly Glu Glu Gln Arg Phe Thr Cys Tyr Met Glu
               100                 105                 110
His Ser Gly Asn His Ser Thr His Pro Val Pro Ser Gly Lys Val Leu
               115                 120                 125
Val Leu Gln Ser His Trp Gln Thr Phe His Val Ser Ala Val Ala Ala
           130                 135                 140
Ala Ala Ile Phe Val Ile
145                 150

<210> SEQ ID NO 8
<211> LENGTH: 36
<212> TYPE: PRT
<213> ORGANISM: Homo sapiens

<400> SEQUENCE: 8

Glu Asp Gln Thr Gln Asp Thr Glu Leu Val Glu Thr Arg Pro Ala Gly
 1               5                  10                  15
Asp Gly Thr Phe Gln Lys Trp Ala Ala Val Val Val Pro Ser Gly Gln
                20                  25                  30
Glu Gln Arg Tyr
            35

<210> SEQ ID NO 9
<211> LENGTH: 37
<212> TYPE: PRT
<213> ORGANISM: Homo sapiens

<400> SEQUENCE: 9

Val Ser Leu Ser His Asp Thr Gln Gln Trp Gly Asp Val Leu Pro Asp
 1               5                  10                  15
Gly Asn Gly Thr Tyr Gln Thr Trp Val Ala Thr Arg Ile Cys Gln Gly
                20                  25                  30
Glu Glu Gln Arg Phe
            35

<210> SEQ ID NO 10
<211> LENGTH: 36
<212> TYPE: PRT
<213> ORGANISM: Artificial
<220> FEATURE:
<223> OTHER INFORMATION: mutant

<400> SEQUENCE: 10

Glu Asp Gln Thr Gln Asp Thr Glu Leu Val Glu Thr Arg Pro Ala Gly
 1               5                  10                  15
Asn Gly Thr Tyr Gln Thr Trp Val Ala Thr Arg Ile Cys Gln Gly Glu
                20                  25                  30
Glu Gln Arg Phe
            35

<210> SEQ ID NO 11
<211> LENGTH: 37
<212> TYPE: PRT
<213> ORGANISM: Artificial
```

<220> FEATURE:
<223> OTHER INFORMATION: mutant

<400> SEQUENCE: 11

Val Ser Leu Ser His Asp Thr Gln Gln Trp Gly Asp Val Leu Pro Asp
1               5                   10                  15

Gly Asn Gly Thr Tyr Gln Thr Trp Val Ala Thr Arg Val Pro Ser Gly
            20                  25                  30

Gln Glu Gln Arg Tyr
            35

<210> SEQ ID NO 12
<211> LENGTH: 37
<212> TYPE: PRT
<213> ORGANISM: Artificial
<220> FEATURE:
<223> OTHER INFORMATION: mutant

<400> SEQUENCE: 12

Val Ser Leu Ser His Asp Thr Gln Gln Trp Gly Asp Val Leu Pro Asp
1               5                   10                  15

Gly Asp Gly Thr Phe Gln Lys Trp Ala Ala Val Val Ile Cys Gln Gly
            20                  25                  30

Glu Glu Gln Arg Phe
            35

<210> SEQ ID NO 13
<211> LENGTH: 37
<212> TYPE: PRT
<213> ORGANISM: Artificial
<220> FEATURE:
<223> OTHER INFORMATION: mutant

<400> SEQUENCE: 13

Val Ser Leu Ser His Asp Thr Gln Gln Trp Gly Asp Val Leu Pro Asp
1               5                   10                  15

Gly Asp Gly Thr Phe Gln Lys Trp Ala Ala Thr Arg Ile Cys Gln Gly
            20                  25                  30

Glu Glu Gln Arg Phe
            35

<210> SEQ ID NO 14
<211> LENGTH: 37
<212> TYPE: PRT
<213> ORGANISM: Artificial
<220> FEATURE:
<223> OTHER INFORMATION: mutant

<400> SEQUENCE: 14

Val Ser Leu Ser His Asp Thr Gln Gln Trp Gly Asp Val Leu Pro Asp
1               5                   10                  15

Gly Asp Gly Thr Phe Gln Lys Trp Val Ala Thr Arg Ile Cys Gln Gly
            20                  25                  30

Glu Glu Gln Arg Phe
            35

<210> SEQ ID NO 15
<211> LENGTH: 37
<212> TYPE: PRT
<213> ORGANISM: Artificial
<220> FEATURE:
<223> OTHER INFORMATION: mutant

<400> SEQUENCE: 15

Val Ser Leu Ser His Asp Thr Gln Gln Trp Gly Asp Val Leu Pro Asp
1               5                   10                  15

Gly Asp Gly Thr Phe Gln Thr Trp Val Ala Thr Arg Ile Cys Gln Gly
                20                  25                  30

Glu Glu Gln Arg Phe
            35

<210> SEQ ID NO 16
<211> LENGTH: 37
<212> TYPE: PRT
<213> ORGANISM: Artificial
<220> FEATURE:
<223> OTHER INFORMATION: mutant

<400> SEQUENCE: 16

Val Ser Leu Ser His Asp Thr Gln Gln Trp Gly Asp Val Leu Pro Asp
1               5                   10                  15

Gly Asn Gly Thr Phe Gln Lys Ser Ala Ala Val Val Ile Cys Gln Gly
                20                  25                  30

Glu Glu Gln Arg Phe
            35

<210> SEQ ID NO 17
<211> LENGTH: 37
<212> TYPE: PRT
<213> ORGANISM: Artificial
<220> FEATURE:
<223> OTHER INFORMATION: mutant

<400> SEQUENCE: 17

Val Ser Leu Ser His Asp Thr Gln Gln Trp Gly Asp Val Leu Pro Asp
1               5                   10                  15

Gly Asn Gly Thr Tyr Gln Lys Ser Ala Ala Val Val Ile Cys Gln Gly
                20                  25                  30

Glu Glu Gln Arg Phe
            35

<210> SEQ ID NO 18
<211> LENGTH: 37
<212> TYPE: PRT
<213> ORGANISM: Artificial
<220> FEATURE:
<223> OTHER INFORMATION: mutant

<400> SEQUENCE: 18

Val Ser Leu Ser His Asp Thr Gln Gln Trp Gly Asp Val Leu Pro Asp
1               5                   10                  15

Gly Asn Gly Thr Phe Gln Lys Ser Ala Ala Val Arg Ile Cys Gln Gly
                20                  25                  30

Glu Glu Gln Arg Phe
            35

<210> SEQ ID NO 19
<211> LENGTH: 37
<212> TYPE: PRT
<213> ORGANISM: Artificial
<220> FEATURE:
<223> OTHER INFORMATION: mutant

<400> SEQUENCE: 19

Val Ser Leu Ser His Asp Thr Gln Gln Trp Gly Asp Val Leu Pro Asp
1               5                   10                  15

Gly Asn Gly Thr Phe Gln Thr Trp Val Ala Thr Arg Ile Cys Gln Gly
            20                  25                  30

Glu Glu Gln Arg Phe
        35

<210> SEQ ID NO 20
<211> LENGTH: 37
<212> TYPE: PRT
<213> ORGANISM: Artificial
<220> FEATURE:
<223> OTHER INFORMATION: mutant

<400> SEQUENCE: 20

Val Ser Leu Ser His Asp Thr Gln Gln Trp Gly Asp Val Leu Pro Asp
1               5                   10                  15

Gly Asn Gly Thr Tyr Ala Thr Trp Val Ala Thr Arg Ile Cys Gln Gly
            20                  25                  30

Glu Glu Gln Arg Phe
        35

<210> SEQ ID NO 21
<211> LENGTH: 37
<212> TYPE: PRT
<213> ORGANISM: Artificial
<220> FEATURE:
<223> OTHER INFORMATION: mutant

<400> SEQUENCE: 21

Val Ser Leu Ser His Asp Thr Gln Gln Trp Gly Asp Val Leu Pro Asp
1               5                   10                  15

Gly Asn Gly Thr Tyr Gln Lys Trp Val Ala Thr Arg Ile Cys Gln Gly
            20                  25                  30

Glu Glu Gln Arg Phe
        35

<210> SEQ ID NO 22
<211> LENGTH: 26
<212> TYPE: PRT
<213> ORGANISM: Homo sapiens

<400> SEQUENCE: 22

Gln Asp Gly Val Ser Leu Ser His Asp Thr Gln Gln Trp Gly Asp Val
1               5                   10                  15

Leu Pro Asp Gly Asn Gly Thr Tyr Gln Thr
            20                  25

<210> SEQ ID NO 23
<211> LENGTH: 27
<212> TYPE: PRT
<213> ORGANISM: Homo sapiens

<400> SEQUENCE: 23

Gln Asp Gly Val Ser Leu Ser His Asp Thr Gln Gln Trp Gly Asp Val
1               5                   10                  15

Leu Pro Asp Gly Asn Gly Thr Tyr Gln Thr Trp
            20                  25

<210> SEQ ID NO 24
<211> LENGTH: 6
<212> TYPE: PRT
<213> ORGANISM: Homo sapiens

<400> SEQUENCE: 24

Phe Thr Cys Tyr Met Glu
1               5

<210> SEQ ID NO 25
<211> LENGTH: 17
<212> TYPE: PRT
<213> ORGANISM: Homo sapiens

<400> SEQUENCE: 25

Phe Thr Cys Tyr Met Glu His Ser Gly Asn His Ser Thr His Pro Val
1               5                   10                  15

Pro

<210> SEQ ID NO 26
<211> LENGTH: 48
<212> TYPE: PRT
<213> ORGANISM: Homo sapiens

<400> SEQUENCE: 26

Arg Ile Cys Gln Gly Glu Glu Gln Arg Phe Thr Cys Tyr Met Glu His
1               5                   10                  15

Ser Gly Asn His Ser Thr His Pro Val Pro Ser Gly Lys Val Leu Val
            20                  25                  30

Leu Gln Ser His Trp Gln Thr Phe His Val Ser Ala Val Ala Ala Ala
        35                  40                  45

<210> SEQ ID NO 27
<211> LENGTH: 56
<212> TYPE: PRT
<213> ORGANISM: Homo sapiens

<400> SEQUENCE: 27

Val Pro Ser Gly Gln Glu Gln Arg Tyr Thr Cys His Val Gln His Glu
1               5                   10                  15

Gly Leu Pro Lys Pro Leu Thr Leu Arg Trp Glu Leu Ser Ser Gln Pro
            20                  25                  30

Thr Ile Pro Ile Val Gly Ile Ile Ala Gly Leu Val Leu Leu Gly Ala
        35                  40                  45

Val Ile Thr Gly Ala Val Val Ala
    50                  55

<210> SEQ ID NO 28
<211> LENGTH: 46
<212> TYPE: PRT
<213> ORGANISM: Homo sapiens

<400> SEQUENCE: 28

Ile Cys Gln Gly Glu Glu Gln Arg Phe Thr Cys Tyr Met Glu His Ser
1               5                   10                  15

Gly Asn His Ser Thr His Pro Val Pro Ser Gly Lys Val Leu Val Leu
            20                  25                  30

Gln Ser His Trp Gln Thr Phe His Val Ser Ala Val Ala Ala
        35                  40                  45

<210> SEQ ID NO 29
<211> LENGTH: 46
<212> TYPE: PRT
<213> ORGANISM: Artificial
<220> FEATURE:
<223> OTHER INFORMATION: mutant

<400> SEQUENCE: 29

Ile Cys Gln Gly Glu Glu Gln Arg Tyr Thr Cys His Val Gln His Glu
1               5                   10                  15

Gly Leu Pro Lys Pro Leu Thr Leu Arg Trp Gly Lys Val Leu Val Leu
            20                  25                  30

Gln Ser His Trp Gln Thr Phe His Val Ser Ala Val Ala Ala
            35                  40                  45

<210> SEQ ID NO 30
<211> LENGTH: 56
<212> TYPE: PRT
<213> ORGANISM: Artificial
<220> FEATURE:
<223> OTHER INFORMATION: mutant

<400> SEQUENCE: 30

Ile Cys Gln Gly Glu Glu Gln Arg Phe Thr Cys Tyr Met Glu His Ser
1               5                   10                  15

Gly Asn His Ser Thr His Pro Val Pro Ser Glu Leu Ser Ser Gln Pro
            20                  25                  30

Thr Ile Pro Ile Val Gly Ile Ile Ala Gly Leu Val Leu Leu Gly Ala
            35                  40                  45

Val Ile Thr Ser Ala Val Ala Ala
        50                  55

<210> SEQ ID NO 31
<211> LENGTH: 80
<212> TYPE: PRT
<213> ORGANISM: Homo sapiens

<400> SEQUENCE: 31

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
            50                  55                  60

Gly Asn His Ser Thr His Pro Val Pro Ser Gly Lys Val Leu Val Leu
65                  70                  75                  80

<210> SEQ ID NO 32
<211> LENGTH: 80
<212> TYPE: PRT
<213> ORGANISM: Homo sapiens

<400> SEQUENCE: 32

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
            50                  55                  60

Gly Asn His Ser Thr His Pro Val Pro Ser Gly Lys Val Leu Val Leu
65                  70                  75                  80

<210> SEQ ID NO 33
<211> LENGTH: 74

```
<212> TYPE: PRT
<213> ORGANISM: Homo sapiens

<400> SEQUENCE: 33

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 34
<211> LENGTH: 80
<212> TYPE: PRT
<213> ORGANISM: Homo sapiens

<400> SEQUENCE: 34

Thr Cys Arg Ala Ser Ser Phe Tyr Pro Arg Asn Ile Thr Leu Thr Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 35
<211> LENGTH: 74
<212> TYPE: PRT
<213> ORGANISM: Homo sapiens

<400> SEQUENCE: 35

Thr Cys Arg Ala Ser Ser Phe Tyr Pro Arg Asn Ile Thr Leu Thr Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Arg Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 36
<211> LENGTH: 80
<212> TYPE: PRT
<213> ORGANISM: Homo sapiens

<400> SEQUENCE: 36

Thr Cys Arg Ala Ser Ser Phe Tyr Pro Arg Asn Ile Thr Leu Thr Trp
1               5                   10                  15

Arg Gln Asp Gly Val Ser Leu Ser His Asp Thr Gln Gln Trp Gly Asp
            20                  25                  30
```

-continued

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
 50                  55                  60

Gly Asn His Ser Thr His Pro Val Pro Ser Gly Lys Val Leu Val Leu
 65                  70                  75                  80

<210> SEQ ID NO 37
<211> LENGTH: 80
<212> TYPE: PRT
<213> ORGANISM: Homo sapiens

<400> SEQUENCE: 37

Thr Cys Arg Ala Ser Gly Phe Tyr Pro Trp Asn Ile Thr Leu Ser Trp
 1               5                  10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
 50                  55                  60

Gly Asn His Ser Thr His Pro Val Pro Ser Gly Lys Val Leu Val Leu
 65                  70                  75                  80

<210> SEQ ID NO 38
<211> LENGTH: 74
<212> TYPE: PRT
<213> ORGANISM: Homo sapiens

<400> SEQUENCE: 38

Thr Cys Arg Ala Ser Gly Phe Tyr Pro Trp Asn Ile Thr Leu Ser Trp
 1               5                  10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
 50                  55                  60

Gly Asn His Ser Thr His Pro Val Pro Ser
 65                  70

<210> SEQ ID NO 39
<211> LENGTH: 80
<212> TYPE: PRT
<213> ORGANISM: Homo sapiens

<400> SEQUENCE: 39

Thr Cys Arg Ala Ser Gly Phe Tyr Pro Trp Asn Ile Thr Leu Ser Trp
 1               5                  10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
 50                  55                  60

Gly Asn His Ser Thr His Pro Val Pro Ser Gly Lys Val Leu Val Leu
 65                  70                  75                  80

<210> SEQ ID NO 40

```
<211> LENGTH: 81
<212> TYPE: PRT
<213> ORGANISM: Homo sapiens

<400> SEQUENCE: 40

Thr Cys Arg Ala Ser Ser Phe Tyr Pro Arg Asn Ile Ile Thr Thr Ser
1               5                   10                  15

Trp Arg Gln Asp Gly Val Ser Leu Ser His Asp Thr Gln Gln Trp Gly
                20                  25                  30

Asp Val Leu Pro Asp Gly Asn Gly Thr Tyr Gln Thr Trp Val Ala Thr
            35                  40                  45

Arg Ile Cys Arg Gly Glu Glu Gln Arg Phe Thr Cys Tyr Met Glu His
        50                  55                  60

Ser Gly Asn His Ser Thr His Pro Val Pro Ser Gly Lys Val Leu Val
65                  70                  75                  80

Leu

<210> SEQ ID NO 41
<211> LENGTH: 81
<212> TYPE: PRT
<213> ORGANISM: Homo sapiens

<400> SEQUENCE: 41

Thr Cys Arg Ala Ser Ser Phe Tyr Pro Arg Asn Ile Ile Thr Thr Ser
1               5                   10                  15

Trp Arg Gln Asp Gly Val Ser Leu Ser His Asp Thr Gln Gln Trp Gly
                20                  25                  30

Asp Val Leu Pro Asp Gly Asn Gly Thr Tyr Gln Thr Trp Val Ala Thr
            35                  40                  45

Arg Ile Cys Arg Gly Glu Glu Gln Arg Phe Thr Cys Tyr Met Glu His
        50                  55                  60

Ser Gly Asn His Ser Thr His Pro Val Pro Ser Gly Lys Val Leu Val
65                  70                  75                  80

Leu

<210> SEQ ID NO 42
<211> LENGTH: 75
<212> TYPE: PRT
<213> ORGANISM: Homo sapiens

<400> SEQUENCE: 42

Thr Cys Arg Ala Ser Ser Phe Tyr Pro Arg Asn Ile Ile Thr Thr Ser
1               5                   10                  15

Trp Arg Gln Asp Gly Val Ser Leu Ser His Asp Thr Gln Gln Trp Gly
                20                  25                  30

Asp Val Leu Pro Asp Gly Asn Gly Thr Tyr Gln Thr Trp Val Ala Thr
            35                  40                  45

Arg Ile Cys Arg Gly Glu Glu Gln Arg Phe Thr Cys Tyr Met Glu His
        50                  55                  60

Ser Gly Asn His Ser Thr His Pro Val Pro Ser
65                  70                  75

<210> SEQ ID NO 43
<211> LENGTH: 80
<212> TYPE: PRT
<213> ORGANISM: Homo sapiens

<400> SEQUENCE: 43

Thr Cys Arg Ala Ser Ser Phe Tyr Pro Arg Asn Ile Thr Leu Thr Trp
```

-continued

```
                1               5                  10                 15
Arg Gln Asp Gly Val Ser Leu Ser His Asp Thr Gln Gln Trp Gly Asp
            20                  25                 30

Val Leu Pro Asp Gly Asn Gly Thr Tyr Gln Thr Trp Val Ala Thr Arg
            35                  40                 45

Ile Cys Gln Gly Glu Glu Gln Arg Phe Thr Cys Tyr Met Glu His Ser
        50                  55                 60

Gly Asn His Ser Thr His Pro Val Pro Ser Gly Lys Val Leu Val Leu
65                  70                  75                      80
```

<210> SEQ ID NO 44
<211> LENGTH: 80
<212> TYPE: PRT
<213> ORGANISM: Homo sapiens

<400> SEQUENCE: 44

```
Thr Cys Arg Ala Ser Ser Phe Tyr Pro Arg Asn Ile Thr Leu Thr Trp
1               5                   10                 15

Arg Gln Asp Gly Val Ser Leu Ser His Asp Thr Gln Gln Trp Gly Asp
            20                  25                 30

Val Leu Pro Asp Gly Asn Gly Thr Tyr Gln Thr Trp Val Ala Thr Arg
            35                  40                 45

Ile Cys Gln Gly Glu Glu Gln Arg Phe Thr Cys Tyr Met Glu His Ser
        50                  55                 60

Gly Asn His Ser Thr His Pro Val Pro Ser Gly Lys Val Leu Val Leu
65                  70                  75                      80
```

<210> SEQ ID NO 45
<211> LENGTH: 80
<212> TYPE: PRT
<213> ORGANISM: Homo sapiens

<400> SEQUENCE: 45

```
Thr Cys Arg Ala Ser Ser Phe Tyr Pro Arg Asn Ile Ile Leu Thr Trp
1               5                   10                 15

Arg Gln Asp Gly Val Ser Leu Ser His Asp Thr Gln Gln Trp Gly Asp
            20                  25                 30

Val Leu Pro Asp Gly Asn Gly Thr Tyr Gln Thr Trp Val Ala Thr Arg
            35                  40                 45

Ile Cys Arg Gly Glu Glu Gln Arg Phe Thr Cys Tyr Met Glu His Ser
        50                  55                 60

Gly Asn His Ser Thr His Pro Val Pro Ser Gly Lys Val Leu Val Leu
65                  70                  75                      80
```

<210> SEQ ID NO 46
<211> LENGTH: 80
<212> TYPE: PRT
<213> ORGANISM: Homo sapiens

<400> SEQUENCE: 46

```
Thr Cys Arg Ala Ser Gly Phe Tyr Pro Trp Asn Ile Thr Leu Ser Trp
1               5                   10                 15

Arg Gln Asp Gly Val Ser Leu Ser His Asp Thr Gln Gln Trp Gly Asp
            20                  25                 30

Val Leu Pro Asp Gly Asn Gly Thr Tyr Gln Thr Trp Val Ala Thr Arg
            35                  40                 45

Ile Cys Gln Gly Glu Glu Gln Arg Phe Thr Cys Tyr Met Glu His Ser
        50                  55                 60
```

Gly Asn His Ser Thr His Ala Val Pro Ser Gly Lys Val Leu Val Leu
65                  70                  75                  80

<210> SEQ ID NO 47
<211> LENGTH: 80
<212> TYPE: PRT
<213> ORGANISM: Homo sapiens

<400> SEQUENCE: 47

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
        50                  55                  60

Gly Asn His Ser Thr His Pro Val Pro Ser Gly Lys Val Leu Val Leu
65                  70                  75                  80

<210> SEQ ID NO 48
<211> LENGTH: 74
<212> TYPE: PRT
<213> ORGANISM: Homo sapiens

<400> SEQUENCE: 48

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
        50                  55                  60

Gly Asn His Ser Thr His Pro Val Pro Ser
65                  70

<210> SEQ ID NO 49
<211> LENGTH: 74
<212> TYPE: PRT
<213> ORGANISM: Homo sapiens

<400> SEQUENCE: 49

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Arg Gly Glu Glu Gln Arg Phe Thr Cys Tyr Met Glu His Ser
        50                  55                  60

Gly Asn His Ser Thr His Pro Val Pro Ser
65                  70

<210> SEQ ID NO 50
<211> LENGTH: 74
<212> TYPE: PRT
<213> ORGANISM: Homo sapiens

<400> SEQUENCE: 50

```
Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
50                  55                  60

Gly Asn His Ser Thr His Pro Val Pro Ser
65                  70
```

<210> SEQ ID NO 51
<211> LENGTH: 80
<212> TYPE: PRT
<213> ORGANISM: Homo sapiens

<400> SEQUENCE: 51

```
Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
50                  55                  60

Gly Asn His Ser Thr His Pro Val Pro Ser Gly Lys Cys Trp Cys Phe
65                  70                  75                  80
```

<210> SEQ ID NO 52
<211> LENGTH: 80
<212> TYPE: PRT
<213> ORGANISM: Homo sapiens

<400> SEQUENCE: 52

```
Thr Cys Arg Ala Ser Ser Phe Tyr Pro Arg Asn Ile Ile Leu Thr Trp
1               5                   10                  15

Arg Gln Asp Gly Leu Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Arg Gly Glu Glu Gln Arg Phe Thr Cys Tyr Met Glu His Ser
50                  55                  60

Gly Asn His Ser Thr His Pro Val Pro Ser Gly Lys Val Leu Val Leu
65                  70                  75                  80
```

<210> SEQ ID NO 53
<211> LENGTH: 80
<212> TYPE: PRT
<213> ORGANISM: Homo sapiens

<400> SEQUENCE: 53

```
Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
50                  55                  60
```

Gly Asn His Ser Thr His Pro Val Pro Ser Gly Lys Cys Trp Cys Phe
65                  70                  75                  80

<210> SEQ ID NO 54
<211> LENGTH: 80
<212> TYPE: PRT
<213> ORGANISM: Homo sapiens

<400> SEQUENCE: 54

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
        50                  55                  60

Gly Asn His Ser Thr His Pro Val Pro Ser Gly Lys Val Leu Val Leu
65                  70                  75                  80

<210> SEQ ID NO 55
<211> LENGTH: 80
<212> TYPE: PRT
<213> ORGANISM: Homo sapiens

<400> SEQUENCE: 55

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
        50                  55                  60

Gly Asn His Ser Thr His Pro Val Pro Ser Gly Lys Val Leu Val Leu
65                  70                  75                  80

<210> SEQ ID NO 56
<211> LENGTH: 81
<212> TYPE: PRT
<213> ORGANISM: Homo sapiens

<400> SEQUENCE: 56

Thr Cys Arg Ala Ser Ser Phe Tyr Pro Arg Asn Ile Ile Leu Thr Ser
1               5                   10                  15

Trp Arg Gln Asp Gly Val Ser Leu Ser His Asp Thr Gln Gln Trp Gly
                20                  25                  30

Asp Val Leu Pro Asp Gly Asn Gly Thr Tyr Gln Thr Trp Val Ala Thr
            35                  40                  45

Arg Ile Cys Arg Gly Glu Glu Gln Arg Phe Thr Cys Tyr Met Glu His
        50                  55                  60

Ser Gly Asn His Ser Thr His Pro Val Pro Ser Gly Lys Val Leu Val
65                  70                  75                  80

Leu

<210> SEQ ID NO 57
<211> LENGTH: 80
<212> TYPE: PRT
<213> ORGANISM: Homo sapiens

```
<400> SEQUENCE: 57

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 58
<211> LENGTH: 74
<212> TYPE: PRT
<213> ORGANISM: Homo sapiens

<400> SEQUENCE: 58

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 59
<211> LENGTH: 74
<212> TYPE: PRT
<213> ORGANISM: Homo sapiens

<400> SEQUENCE: 59

Thr Cys Arg Ala Ser Ser Phe Tyr Pro Arg Asn Ile Ile Leu Thr Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Arg Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 60
<211> LENGTH: 80
<212> TYPE: PRT
<213> ORGANISM: Homo sapiens

<400> SEQUENCE: 60

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45
```

```
Ile Cys Gln Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 61
<211> LENGTH: 74
<212> TYPE: PRT
<213> ORGANISM: Homo sapiens

<400> SEQUENCE: 61

Thr Cys Arg Ala Ser Ser Phe Tyr Pro Arg Asn Ile Thr Leu Thr Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 62
<211> LENGTH: 74
<212> TYPE: PRT
<213> ORGANISM: Homo sapiens

<400> SEQUENCE: 62

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 63
<211> LENGTH: 80
<212> TYPE: PRT
<213> ORGANISM: Homo sapiens

<400> SEQUENCE: 63

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 64
<211> LENGTH: 80
<212> TYPE: PRT
```

<213> ORGANISM: Homo sapiens

<400> SEQUENCE: 64

Thr Cys Arg Ala Ser Ser Phe Tyr Pro Arg Asn Ile Ile Leu Thr Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Arg Gly Glu Glu Gln Arg Phe Thr Cys Tyr Met Glu His Ser
        50                  55                  60

Gly Asn His Ser Thr His Pro Val Pro Ser Gly Lys Val Leu Val Leu
65                  70                  75                  80

<210> SEQ ID NO 65
<211> LENGTH: 80
<212> TYPE: PRT
<213> ORGANISM: Homo sapiens

<400> SEQUENCE: 65

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
        50                  55                  60

Gly Asn His Ser Thr His Pro Val Pro Ser Gly Lys Val Leu Val Leu
65                  70                  75                  80

<210> SEQ ID NO 66
<211> LENGTH: 80
<212> TYPE: PRT
<213> ORGANISM: Homo sapiens

<400> SEQUENCE: 66

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
        50                  55                  60

Gly Asn His Ser Thr His Pro Val Pro Ser Gly Lys Val Leu Val Leu
65                  70                  75                  80

<210> SEQ ID NO 67
<211> LENGTH: 74
<212> TYPE: PRT
<213> ORGANISM: Homo sapiens

<400> SEQUENCE: 67

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg

```
            35                  40                  45
Ile Cys Gln Gly Glu Glu Gln Arg Phe Thr Cys Tyr Met Glu His Ser
 50                  55                  60

Gly Asn His Ser Thr His Ala Val Pro Ser
 65                  70
```

<210> SEQ ID NO 68
<211> LENGTH: 74
<212> TYPE: PRT
<213> ORGANISM: Homo sapiens

<400> SEQUENCE: 68

```
Thr Cys Arg Ala Ser Gly Phe Tyr Pro Trp Asn Ile Thr Leu Ser Trp
 1               5                  10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
 50                  55                  60

Gly Asn His Ser Thr His Pro Val Pro Ser
 65                  70
```

<210> SEQ ID NO 69
<211> LENGTH: 74
<212> TYPE: PRT
<213> ORGANISM: Homo sapiens

<400> SEQUENCE: 69

```
Thr Cys Arg Ala Ser Gly Phe Tyr Pro Trp Asn Ile Thr Leu Ser Trp
 1               5                  10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
            35                  40                  45

Ile Cys Gln Gly Glu Glu Gln Arg Phe Thr Cys Tyr Met Glu His Ser
 50                  55                  60

Gly Asn His Ser Thr His Pro Val Pro Ser
 65                  70
```

<210> SEQ ID NO 70
<211> LENGTH: 81
<212> TYPE: PRT
<213> ORGANISM: Homo sapiens

<400> SEQUENCE: 70

```
Thr Cys Arg Ala Ser Ser Phe Tyr Pro Arg Asn Ile Thr Leu Thr Ser
 1               5                  10                  15

Trp Arg Gln Asp Gly Val Ser Leu Ser His Asp Thr Gln Gln Trp Gly
                20                  25                  30

Asp Val Leu Pro Asp Gly Asn Gly Thr Tyr Gln Thr Trp Val Ala Thr
            35                  40                  45

Arg Ile Cys Arg Gly Glu Glu Gln Arg Phe Cys Tyr Met Glu His
 50                  55                  60

Ser Gly Asn His Ser Thr His Pro Val Pro Ser Gly Lys Val Leu Val
 65                  70                  75                  80

Leu
```

```
<210> SEQ ID NO 71
<211> LENGTH: 75
<212> TYPE: PRT
<213> ORGANISM: Homo sapiens

<400> SEQUENCE: 71

Thr Cys Arg Ala Ser Ser Phe Tyr Pro Arg Asn Ile Thr Leu Thr Ser
1               5                   10                  15

Trp Arg Gln Asp Gly Val Ser Leu Ser His Asp Thr Gln Gln Trp Gly
            20                  25                  30

Asp Val Leu Pro Asp Gly Asn Gly Thr Tyr Gln Thr Trp Val Ala Thr
        35                  40                  45

Arg Ile Cys Gln Gly Glu Glu Gln Arg Phe Thr Cys Tyr Met Glu His
    50                  55                  60

Ser Gly Asn His Ser Thr His Pro Val Pro Ser
65                  70                  75

<210> SEQ ID NO 72
<211> LENGTH: 74
<212> TYPE: PRT
<213> ORGANISM: Homo sapiens

<400> SEQUENCE: 72

Thr Cys Arg Ala Ser Ser Phe Tyr Pro Arg Asn Ile Ile Leu Thr Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Arg Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 73
<211> LENGTH: 74
<212> TYPE: PRT
<213> ORGANISM: Homo sapiens

<400> SEQUENCE: 73

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 74
<211> LENGTH: 74
<212> TYPE: PRT
<213> ORGANISM: Homo sapiens

<400> SEQUENCE: 74

Thr Cys Arg Ala Ser Ser Phe Tyr Pro Arg Asn Ile Ile Leu Thr Trp
1               5                   10                  15

Arg Gln Asp Gly Val Ser Leu Ser His Asp Thr Gln Gln Trp Gly Asp
```

```
                    20                  25                  30

Val Leu Pro Asp Gly Asn Gly Thr Tyr Gln Thr Trp Val Ala Thr Arg
                35                  40                  45

Ile Cys Arg Gly Glu Glu Gln Arg Phe Thr Cys Tyr Met Glu His Ser
            50                  55                  60

Gly Asn His Ser Thr His Pro Val Pro Ser
65                  70

<210> SEQ ID NO 75
<211> LENGTH: 74
<212> TYPE: PRT
<213> ORGANISM: Homo sapiens

<400> SEQUENCE: 75

Thr Cys Arg Ala Ser Ser Phe Tyr Pro Arg Asn Ile Thr Leu Thr Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
                35                  40                  45

Ile Cys Gln Gly Glu Glu Gln Arg Phe Thr Cys Tyr Met Glu His Ser
            50                  55                  60

Gly Asn His Ser Thr His Pro Val Pro Ser
65                  70

<210> SEQ ID NO 76
<211> LENGTH: 75
<212> TYPE: PRT
<213> ORGANISM: Homo sapiens

<400> SEQUENCE: 76

Thr Cys Arg Ala Ser Ser Phe Tyr Pro Arg Asn Ile Ile Leu Thr Trp
1               5                   10                  15

Arg Gln Asp Gly Leu Ser Leu Ser His Asp Thr Gln Gln Trp Gly Asp
                20                  25                  30

Val Leu Pro Asp Gly Asn Gly Thr Tyr Gln Thr Trp Val Ala Thr Arg
                35                  40                  45

Ile Cys Arg Gln Gly Glu Glu Gln Arg Phe Thr Cys Tyr Met Glu His
            50                  55                  60

Ser Gly Asn His Ser Thr His Pro Val Pro Ser
65                  70                  75

<210> SEQ ID NO 77
<211> LENGTH: 74
<212> TYPE: PRT
<213> ORGANISM: Homo sapiens

<400> SEQUENCE: 77

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
                35                  40                  45

Ile Cys Gln Gly Glu Glu Gln Arg Phe Thr Cys Tyr Met Glu His Ser
            50                  55                  60

Gly Asn His Ser Thr His Pro Val Pro Ser
65                  70
```

<210> SEQ ID NO 78
<211> LENGTH: 80
<212> TYPE: PRT
<213> ORGANISM: Homo sapiens

<400> SEQUENCE: 78

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 79
<211> LENGTH: 74
<212> TYPE: PRT
<213> ORGANISM: Homo sapiens

<400> SEQUENCE: 79

Thr Cys Arg Ala Ser Arg Phe Tyr Pro Arg Asn Ile Ile Leu Thr Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Arg Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 80
<211> LENGTH: 80
<212> TYPE: PRT
<213> ORGANISM: Homo sapiens

<400> SEQUENCE: 80

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Ser Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 81
<211> LENGTH: 74
<212> TYPE: PRT
<213> ORGANISM: Homo sapiens

<400> SEQUENCE: 81

Thr Cys Arg Ala Ser Ser Phe Tyr Pro Arg Asn Ile Thr Leu Thr Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 82
<211> LENGTH: 80
<212> TYPE: PRT
<213> ORGANISM: Homo sapiens

<400> SEQUENCE: 82

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Glu Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 83
<211> LENGTH: 80
<212> TYPE: PRT
<213> ORGANISM: Homo sapiens

<400> SEQUENCE: 83

Thr Cys Arg Ala Ser Gly Phe Cys Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 84
<211> LENGTH: 80
<212> TYPE: PRT
<213> ORGANISM: Homo sapiens

<400> SEQUENCE: 84

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Ala Val Pro Ser Gly Lys Val Leu Val Leu
65                  70                  75                  80

<210> SEQ ID NO 85
<211> LENGTH: 80
<212> TYPE: PRT
<213> ORGANISM: Homo sapiens

<400> SEQUENCE: 85

Thr Cys Arg Ala Ser Ser Phe Tyr Pro Arg Asn Ile Ile Leu Thr Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Arg Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 86
<211> LENGTH: 81
<212> TYPE: PRT
<213> ORGANISM: Homo sapiens

<400> SEQUENCE: 86

Thr Cys Arg Ala Ser Ser Phe Tyr Pro Arg Asn Ile Thr Leu Thr Ser
1               5                   10                  15

Trp Arg Gln Asp Gly Val Ser Leu Ser His Asp Thr Gln Gln Trp Gly
            20                  25                  30

Asp Val Leu Pro Asp Gly Asn Gly Thr Tyr Gln Thr Trp Val Ala Thr
        35                  40                  45

Arg Ile Cys Gln Gly Glu Glu Gln Arg Phe Thr Cys Tyr Met Glu His
    50                  55                  60

Ser Gly Asn His Ser Thr His Pro Val Pro Ser Gly Lys Val Leu Val
65                  70                  75                  80

Leu

<210> SEQ ID NO 87
<211> LENGTH: 80
<212> TYPE: PRT
<213> ORGANISM: Homo sapiens

<400> SEQUENCE: 87

Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
            20                  25                  30

Val Leu Pro Asp Gly Asn Gly Thr Tyr Gln Thr Trp Val Ala Thr Arg
        35                  40                  45

Ile Cys Gln Gly Glu Glu Gln Arg Phe Thr Cys Tyr Met Glu His Ser
    50                  55                  60

Gly Asn His Ser Thr His Pro Val Pro Ser Gly Lys Val Leu Val Leu
65                  70                  75                  80

<210> SEQ ID NO 88
<211> LENGTH: 80
<212> TYPE: PRT
<213> ORGANISM: Homo sapiens

<400> SEQUENCE: 88

```
Thr Cys Arg Ala Ser Gly Phe Tyr Pro Trp Asn Ile Thr Leu Ser Trp
1               5                   10                  15

Arg Gln Asp Gly Val Ser Leu Ser His Asp Thr Gln Gln Trp Gly Asp
                20                  25                  30

Val Leu Pro Asp Gly Asn Gly Thr Tyr Gln Thr Trp Val Ala Thr Arg
                35                  40                  45

Ile Cys Gln Gly Glu Glu Gln Arg Phe Thr Cys Tyr Met Glu His Ser
            50                  55                  60

Gly Asn His Ser Thr His Pro Val Pro Ser Gly Lys Val Leu Val Leu
65                  70                  75                  80
```

<210> SEQ ID NO 89
<211> LENGTH: 80
<212> TYPE: PRT
<213> ORGANISM: Homo sapiens

<400> SEQUENCE: 89

```
Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
                20                  25                  30

Val Leu Pro Asp Gly Asn Gly Thr Tyr Gln Thr Trp Val Ala Thr Arg
                35                  40                  45

Ile Arg Gln Gly Glu Glu Gln Arg Phe Thr Cys Tyr Met Glu His Ser
            50                  55                  60

Gly Asn His Gly Thr His Pro Val Pro Ser Gly Lys Val Leu Val Leu
65                  70                  75                  80
```

<210> SEQ ID NO 90
<211> LENGTH: 80
<212> TYPE: PRT
<213> ORGANISM: Homo sapiens

<400> SEQUENCE: 90

```
Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
                20                  25                  30

Val Leu Pro Asp Gly Asn Gly Thr Tyr Gln Thr Trp Val Ala Thr Arg
                35                  40                  45

Ile Arg Gln Gly Glu Glu Gln Arg Phe Thr Cys Tyr Met Glu His Ser
            50                  55                  60

Gly Asn His Gly Thr His Pro Val Pro Ser Gly Lys Ala Leu Val Leu
65                  70                  75                  80
```

<210> SEQ ID NO 91
<211> LENGTH: 80
<212> TYPE: PRT
<213> ORGANISM: Homo sapiens

<400> SEQUENCE: 91

```
Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
                20                  25                  30

Val Leu Pro Asp Gly Asn Gly Thr Tyr Gln Thr Trp Val Ala Thr Arg
                35                  40                  45

Ile Arg Gln Gly Glu Glu Gln Arg Phe Thr Cys Tyr Met Glu His Ser
            50                  55                  60
```

Gly Asn His Gly Thr His Pro Val Pro Ser Gly Lys Ala Leu Val Leu
65                  70                  75                  80

<210> SEQ ID NO 92
<211> LENGTH: 80
<212> TYPE: PRT
<213> ORGANISM: Homo sapiens

<400> SEQUENCE: 92

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
                20                  25                  30

Val Leu Pro Asp Gly Asn Gly Thr Tyr Gln Thr Trp Val Ala Thr Arg
            35                  40                  45

Ile Arg Gln Gly Glu Glu Gln Arg Phe Thr Cys Tyr Met Glu His Ser
        50                  55                  60

Gly Asn His Gly Thr His Pro Val Pro Ser Gly Lys Ala Leu Val Leu
65                  70                  75                  80

<210> SEQ ID NO 93
<211> LENGTH: 80
<212> TYPE: PRT
<213> ORGANISM: Homo sapiens

<400> SEQUENCE: 93

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
                20                  25                  30

Val Leu Pro Asp Gly Asn Gly Thr Tyr Gln Thr Trp Val Ala Thr Arg
            35                  40                  45

Ile Arg Gln Gly Glu Glu Gln Arg Phe Thr Cys Tyr Met Glu His Ser
        50                  55                  60

Gly Asn His Gly Thr His Pro Val Pro Ser Gly Lys Ala Leu Val Leu
65                  70                  75                  80

<210> SEQ ID NO 94
<211> LENGTH: 80
<212> TYPE: PRT
<213> ORGANISM: Homo sapiens

<400> SEQUENCE: 94

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
                20                  25                  30

Val Leu Pro Asp Gly Asn Gly Thr Tyr Gln Thr Trp Val Ala Thr Arg
            35                  40                  45

Ile Arg Gln Gly Glu Glu Gln Arg Phe Thr Cys Tyr Met Glu His Ser
        50                  55                  60

Gly Asn His Gly Thr His Pro Val Pro Ser Gly Lys Ala Leu Val Leu
65                  70                  75                  80

<210> SEQ ID NO 95
<211> LENGTH: 80
<212> TYPE: PRT
<213> ORGANISM: Homo sapiens

<400> SEQUENCE: 95

```
Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser Gly Lys Ala Leu Val Leu
65                  70                  75                  80

<210> SEQ ID NO 96
<211> LENGTH: 80
<212> TYPE: PRT
<213> ORGANISM: Homo sapiens

<400> SEQUENCE: 96

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser Gly Lys Ala Leu Val Leu
65                  70                  75                  80

<210> SEQ ID NO 97
<211> LENGTH: 80
<212> TYPE: PRT
<213> ORGANISM: Homo sapiens

<400> SEQUENCE: 97

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser Gly Lys Ala Leu Val Leu
65                  70                  75                  80

<210> SEQ ID NO 98
<211> LENGTH: 80
<212> TYPE: PRT
<213> ORGANISM: Homo sapiens

<400> SEQUENCE: 98

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Lys Phe Thr Cys Tyr Met Glu His Ser
```

```
                    50                  55                  60
Gly Asn His Gly Thr His Pro Val Pro Ser Gly Lys Ala Leu Val Leu
 65                  70                  75                  80

<210> SEQ ID NO 99
<211> LENGTH: 80
<212> TYPE: PRT
<213> ORGANISM: Homo sapiens

<400> SEQUENCE: 99

Thr Cys Arg Ala Ser Ser Phe Tyr Pro Arg Asn Ile Thr Leu Thr Trp
  1               5                  10                  15

Arg Gln Asp Gly Val Ser Leu Ser His Asn Thr Gln Gln Trp Gly Asp
                 20                  25                  30

Val Leu Pro Asp Gly Asn Gly Thr Tyr Gln Thr Trp Val Ala Thr Arg
             35                  40                  45

Ile Arg Gln Gly Glu Glu Gln Arg Phe Thr Cys Tyr Met Glu His Ser
         50                  55                  60

Gly Asn His Gly Thr His Pro Val Pro Ser Gly Lys Ala Leu Val Leu
 65                  70                  75                  80

<210> SEQ ID NO 100
<211> LENGTH: 80
<212> TYPE: PRT
<213> ORGANISM: Homo sapiens

<400> SEQUENCE: 100

Thr Cys Arg Ala Ser Ser Phe Tyr Pro Arg Asn Ile Thr Leu Thr Trp
  1               5                  10                  15

Arg Gln Asp Gly Val Ser Leu Ser His Asn Thr Gln Gln Trp Gly Asp
                 20                  25                  30

Val Leu Pro Asp Gly Asn Gly Thr Tyr Gln Thr Trp Val Ala Thr Arg
             35                  40                  45

Ile Arg Gln Gly Glu Glu Gln Arg Phe Thr Cys Tyr Met Glu His Ser
         50                  55                  60

Gly Asn His Gly Thr His Pro Val Pro Ser Gly Lys Ala Leu Val Leu
 65                  70                  75                  80

<210> SEQ ID NO 101
<211> LENGTH: 80
<212> TYPE: PRT
<213> ORGANISM: Homo sapiens

<400> SEQUENCE: 101

Thr Cys Arg Ala Ser Ser Phe Tyr Pro Arg Asn Ile Thr Leu Thr Trp
  1               5                  10                  15

Arg Gln Asp Gly Val Ser Leu Ser His Asn Thr Gln Gln Trp Gly Asp
                 20                  25                  30

Val Leu Pro Asp Gly Asn Gly Thr Tyr Gln Thr Trp Val Ala Thr Arg
             35                  40                  45

Ile Arg Gln Gly Glu Glu Gln Arg Phe Thr Cys Tyr Met Glu His Ser
         50                  55                  60

Gly Asn His Gly Thr His Pro Val Pro Ser Gly Lys Ala Leu Val Leu
 65                  70                  75                  80

<210> SEQ ID NO 102
<211> LENGTH: 80
<212> TYPE: PRT
<213> ORGANISM: Homo sapiens
```

<400> SEQUENCE: 102

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser Gly Lys Ala Leu Val Leu
65                  70                  75                  80

<210> SEQ ID NO 103
<211> LENGTH: 80
<212> TYPE: PRT
<213> ORGANISM: Homo sapiens

<400> SEQUENCE: 103

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Ser Thr His Pro Val Pro Ser Gly Lys Ala Leu Val Leu
65                  70                  75                  80

<210> SEQ ID NO 104
<211> LENGTH: 80
<212> TYPE: PRT
<213> ORGANISM: Homo sapiens

<400> SEQUENCE: 104

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Ser Thr His Pro Val Pro Ser Gly Lys Ala Leu Val Leu
65                  70                  75                  80

<210> SEQ ID NO 105
<211> LENGTH: 80
<212> TYPE: PRT
<213> ORGANISM: Homo sapiens

<400> SEQUENCE: 105

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
            50                  55                  60

Gly Asn His Ser Thr His Pro Val Pro Ser Gly Lys Ala Leu Val Leu
65                  70                  75                  80

<210> SEQ ID NO 106
<211> LENGTH: 74
<212> TYPE: PRT
<213> ORGANISM: Homo sapiens

<400> SEQUENCE: 106

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Ser Thr His Pro Val Pro Ser
65                  70

<210> SEQ ID NO 107
<211> LENGTH: 74
<212> TYPE: PRT
<213> ORGANISM: Homo sapiens

<400> SEQUENCE: 107

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser
65                  70

<210> SEQ ID NO 108
<211> LENGTH: 74
<212> TYPE: PRT
<213> ORGANISM: Homo sapiens

<400> SEQUENCE: 108

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser
65                  70

<210> SEQ ID NO 109
<211> LENGTH: 74
<212> TYPE: PRT
<213> ORGANISM: Homo sapiens -continued

```
<400> SEQUENCE: 109

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser
65                  70

<210> SEQ ID NO 110
<211> LENGTH: 74
<212> TYPE: PRT
<213> ORGANISM: Homo sapiens

<400> SEQUENCE: 110

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser
65                  70

<210> SEQ ID NO 111
<211> LENGTH: 74
<212> TYPE: PRT
<213> ORGANISM: Homo sapiens

<400> SEQUENCE: 111

Thr Cys Arg Ala Ser Ser Phe Tyr Pro Arg Asn Ile Thr Leu Thr Trp
1               5                   10                  15

Arg Gln Asp Gly Val Ser Leu Ser His Asn Thr Gln Gln Trp Gly Asp
            20                  25                  30

Val Leu Pro Asp Gly Asn Gly Thr Tyr Gln Thr Trp Val Ala Thr Arg
        35                  40                  45

Ile Arg Gln Gly Glu Glu Gln Arg Phe Thr Cys Tyr Met Glu His Ser
    50                  55                  60

Gly Asn His Gly Thr His Pro Val Pro Ser
65                  70

<210> SEQ ID NO 112
<211> LENGTH: 11
<212> TYPE: PRT
<213> ORGANISM: Homo sapiens

<400> SEQUENCE: 112

Asn Gly Thr Tyr Gln Thr Trp Val Ala Thr Arg
1               5                   10

<210> SEQ ID NO 113
<211> LENGTH: 7
<212> TYPE: PRT
<213> ORGANISM: Artificial
```

-continued

```
<220> FEATURE:
<223> OTHER INFORMATION: epitope tag

<400> SEQUENCE: 113

Asp Lys Tyr Asp Asp Asp Lys
1               5

<210> SEQ ID NO 114
<211> LENGTH: 6
<212> TYPE: PRT
<213> ORGANISM: Homo sapiens

<400> SEQUENCE: 114

Phe Thr Cys Tyr Met Glu
1               5

<210> SEQ ID NO 115
<211> LENGTH: 6
<212> TYPE: PRT
<213> ORGANISM: Homo sapiens

<400> SEQUENCE: 115

Pro Val Pro Ser Gly Lys
1               5

<210> SEQ ID NO 116
<211> LENGTH: 7
<212> TYPE: PRT
<213> ORGANISM: Homo sapiens

<400> SEQUENCE: 116

Phe Thr Cys Tyr Met Glu His
1               5
```

METHODS FOR TREATING CANCER BY INHIBITING MIC SHEDDING

This application claims the benefit under 35 U.S.C. §119 (e) of U.S. Provisional Patent Application Ser. No. 61/095,004, filed Sep. 8, 2008, and U.S. Provisional Patent Application Ser. No. 61/153,412, filed Feb. 18, 2009, which are hereby incorporated by reference in their entireties.

This invention was made with U.S. Government support under grant numbers 1K01CA116002 and 1P50CA097186-03 awarded by National Institutes of Health. The U.S. Government has certain rights in this invention.

FIELD OF THE INVENTION

The present invention relates to methods and compositions for treating cancer.

BACKGROUND OF THE INVENTION

Expression of murine NKG2D ligands on tumor cells has been shown to be effective in activating NK-mediated tumor elimination experimentally (Cerwenka et al., "Retinoic Acid Early Inducible Genes Define A Ligand Family for the Activating NKG2D Receptor in Mice,"*Immunity* 12: 721-7 (2000); Diefenbach et al., "Rae1 and H60 Ligands of the NKG2D Receptor Stimulate Tumour Immunity," *Nature* 413: 165-71 (2001); Cerwenka et al., "Ectopic Expression of Retinoic Acid Early Inducible-1 Gene (RAE-1) Permits Natural Killer Cell-mediated Rejection of a MHC Class I-bearing Tumor In Vivo," *Proc Natl Acad Sci USA* 98: 11521-6 (2001); Diefenbach et al., "A Novel Ligand for the NKG2D Receptor Activates NK Cells and Macrophages and Induces Tumor Immunity," *Eur J Immunol* 33: 381-91 (2003)). In murine systems, identified NKG2D ligands include the retinoic acid early inducible family of proteins RAE-1 (Cerwenka et al., "Retinoic Acid Early Inducible Genes Define A Ligand Family for the Activating NKG2D Receptor in Mice," *Immunity* 12: 721-7 (2000); Diefenbach et al., "Rae1 and H60 Ligands of the NKG2D Receptor Stimulate Tumour Immunity," *Nature* 413: 165-71 (2001)), the minor histocompatibility antigen H60 (Cerwenka et al., "Retinoic Acid Early Inducible Genes Define A Ligand Family for the Activating NKG2D Receptor in Mice," *Immunity* 12: 721-7 (2000); Diefenbach et al., "Rae1 and H60 Ligands of the NKG2D Receptor Stimulate Tumour Immunity," *Nature* 413: 165-71 (2001)), and the murine ULBP-like transcript 1 (Diefenbach et al., "A Novel Ligand for the NKG2D Receptor Activates NK Cells and Macrophages and Induces Tumor Immunity," *Eur J Immunol* 33: 381-91 (2003); Carayannopoulos et al., "Cutting Edge: Murine UL16-binding Protein-like Transcript 1: A Newly Described Transcript Encoding a High-affinity Ligand for Murine NKG2D," *J Immunol* 169: 4079-83 (2002)). Cells expressing these molecules are sensitive to the cytotoxicity of mouse NK cells. Ectopic expression of RAE-1 and H-60 results in rejection of tumor cell lines expressing normal levels of MHC I molecule (Diefenbach et al., "Rae1 and H60 Ligands of the NKG2D Receptor Stimulate Tumour Immunity," *Nature* 413: 165-71 (2001); Cerwenka et al., "Ectopic Expression of Retinoic Acid Early Inducible-1 Gene (RAE-1) Permits Natural Killer Cell-mediated Rejection of a MHC Class I-bearing Tumor In Vivo," *Proc Natl Acad Sci USA* 98: 11521-6 (2001); Diefenbach et al., "A Novel Ligand for the NKG2D Receptor Activates NK Cells and Macrophages and Induces Tumor Immunity," *Eur J Immunol* 33: 381-91 (2003)). Immune depletion and other experiments showed that the tumor rejection is due to NK cells and CD8 T cells (Diefenbach et al., "Rae1 and H60 Ligands of the NKG2D Receptor Stimulate Tumour Immunity," *Nature* 413: 165-71 (2001); Cerwenka et al., "Ectopic Expression of Retinoic Acid Early Inducible-1 Gene (RAE-1) Permits Natural Killer Cell-mediated Rejection of a MHC Class I-bearing Tumor In Vivo," *Proc Natl Acad Sci USA* 98: 11521-6 (2001)). NKG2D neutralization in vivo enhances host sensitivity to carcinogen-induced spontaneous tumor initiation (Smyth et al., "NKG2D Function Protects the Host from Tumor Initiation," *J Exp Med* 202: 583-8 (2005)). These studies have proven the principal function of NKG2D ligand-receptor mediated NK cell immunity in tumor rejection.

In humans, the MHC class I chain-related molecule A (MICA) and MICB (generally termed as MIC) are the most investigated NKG2D ligands, which were proposed to play roles in tumor rejection (Long E O., "Tumor Cell Recognition by Natural Killer Cells," *Semin Cancer Biol* 12: 57-61 (2002); Raulet D H., "Roles of the NKG2D Immunoreceptor and its Ligands," *Nat Rev Immunol* 3: 781-90 (2003); Cerwenka et al., "NKG2D Ligands: Unconventional MHC Class I-like Molecules Exploited by Viruses and Cancer," *Tissue Antigens* 61: 335-43 (2003)). MIC is rarely expressed by normal human tissues but induced in most human epithelial tumors (Groh et al., "Broad Tumor-associated Expression and Recognition By Tumor-derived Gamma Delta T Cells of MICA and MICB," *Proc Natl Acad Sci USA* 96:6879-84 (1999); Vetter et al., "Expression of Stress-induced MHC Class I Related Chain Molecules on Human Melanoma," *J Invest Dermatol* 118: 600-5 (2002); Jinushi et al., "Expression and Role of MICA and MICB in Human Hepatocellular Carcinomas and Their Regulation by Retinoic Acid," *Int J Cancer* 104: 354-61 (2003); Wu et al., "Prevalent Expression of the Immunostimulatory MHC Class I Chain-related Molecule is Counteracted by Shedding in Prostate Cancer," *J Clin Invest* 114: 560-8 (2004)). Expression of MIC on the tumor cell surface can markedly enhance the sensitivity of tumor cells to NK cells in vitro and has been shown to inhibit the growth of human gliomas or small lung carcinomas in experimental models (Friese et al., "MICA/NKG2D-mediated Immunogene Therapy of Experimental Gliomas," *Cancer Res* 63: 8996-9006 (2003); Busche et al., "Natural Killer Cell-mediated Rejection of Experimental Human Lung Cancer by Genetic Overexpression of Major Histocompatibility Complex Class I Chain-related Gene A," *Hum Gene Ther* 17: 135-46 (2006)). These studies suggest that NK cells can potentially eliminate MIC-positive tumor cells in cancer patients. However, as clinically observed, most of the human epithelial tumors are found to be MIC+ rather than MIC– (Groh et al., "Broad Tumor-associated Expression and Recognition By Tumor-derived Gamma Delta T Cells of MICA and MICB," *Proc Natl Acad Sci USA* 96: 6879-84 (1999); Vetter et al., "Expression of Stress-induced MHC Class I Related Chain Molecules on Human Melanoma," *J Invest Dermatol* 118: 600-5 (2002); Jinushi et al., "Expression and Role of MICA and MICB in Human Hepatocellular Carcinomas and Their Regulation by Retinoic Acid," *Int J Cancer* 104:354-61 (2003); Wu et al., "Prevalent Expression of the Immunostimulatory MHC Class I Chain-related Molecule is Counteracted by Shedding in Prostate Cancer," *J Clin Invest* 114: 560-8 (2004)), which suggests the functional compromise of the MIC ligand-NKG2D receptor system in cancer patients to permit the growth of MIC+ tumor cells. It has been shown that tumor-derived soluble MIC (sMIC), which occurs as a result of tumor shedding is one of the factors causing the ineffectiveness of NKG2D—mediated immunity in cancer patients (Wu et al., "Prevalent Expression of the Immunostimulatory MHC Class I Chain-related Molecule is Counteracted by Shedding in Prostate Cancer," *J Clin Invest* 114: 560-8 (2004); Groh et al., "Tumour-derived Soluble MIC Ligands Impair Expression of NKG2D and T-cell Activation," *Nature* 419: 734-8 (2002); Doubrovina et al., "Evasion from NK Cell Immunity by MHC Class I Chain-related Molecules Expressing Colon Adenocarcinoma," *J Immunol* 171: 6891-9 (2003); Raffaghello L, et al., *Neoplasia* 6: 558-68 (2004); Salih et al., "Down-Regulation of MICA on Human Tumors by Proteolytic Shedding," *J Immunol* 169: 4098-102 (2002); Holdenrieder et al., "Soluble MICA in Malignant Diseases," *Int J Cancer* 118: 684-7 (2006); Marten et al., "Soluble MIC is Elevated in the Serum of Patients with Pancreatic Carcinoma Diminishing Gamma Delta T Cell Cytotoxicity," *Int J Cancer* 119: 2359-65 (2006)). In vitro studies have shown that engagement of soluble MICA to NKG2D results in marked reduction in surface NKG2D expression on NK cells and T cells (13, 16, 21). Thus, sMIC is believed to induce down-modulation of NKG2D expression on systemic and tumor infiltrated NK and T cells and thus result in functional impairment of NK and T cells in MIC+ cancer patients (Wu et al., "Prevalent Expression of the Immunostimulatory MHC Class I Chain-related Molecule is Counteracted by Shedding in Prostate Cancer," *J Clin Invest* 114: 560-8 (2004); Groh et al., "Tumour-derived Soluble MIC Ligands Impair Expression of NKG2D and T-cell Activation," *Nature* 419: 734-8 (2002); Doubrovina et al., "Evasion from NK Cell Immunity by MHC Class I Chain-related Molecules Expressing Colon Adenocarcinoma," *J Immunol* 171:6891-9 (2003)). A reduction in the density of MIC expressed on the tumor cell surface due to MIC shedding from tumors is also one of the mechanisms for tumor evasion (Marten et al., "Soluble MIC is Elevated in the Serum of Patients with Pancreatic Carcinoma Diminishing Gamma Delta T Cell Cytotoxicity," *Int J Cancer* 119:2359-65 (2006)).

SUMMARY OF THE INVENTION

Described herein are methods for treating cancer comprising administering a therapeutically effective amount of an agent that prevents MIC shedding mediated by the alpha-3 ectodomain of MIC of a tumor cell, thus rendering the tumor cell more sensitive to innate immune cell rejection. Also described herein is a cell-based screening assay for identifying or testing the efficacy of an agent for increasing sensitivity of a tumor to immune cell-mediated killing, by measuring MIC shedding in the presence and absence of a candidate agent.

In one aspect, provided herein is a method for treating MIC-positive cancer, the method comprising administering to an individual in need thereof, a therapeutically effective amount of an agent that binds a region in the alpha-3 ectodomain of a MIC polypeptide, whereby the MIC-positive cancer is treated.

In one embodiment of this aspect, the agent inhibits shedding of the MIC polypeptide, or a fragment thereof.

In another embodiment of this aspect, the agent is selected from the group consisting of an antibody or a polypeptide comprising an antigen-binding fragment thereof, a peptide, an aptamer, and a small molecule.

In another embodiment of this aspect, the agent binds a region of the α3 ectodomain comprising the amino acid sequence NGTYQT (SEQ ID NO: 1). In another embodiment of this aspect, the agent physically contacts at least one amino acid of the amino acid sequence NGTYQT (SEQ ID NO: 1) comprised by the α3 ectodomain of a MIC polypeptide.

In another embodiment of this aspect, the agent inhibits the interaction of said MIC polypeptide with ERp5 polypeptide.

In another embodiment of this aspect, the cancer comprises an epithelial cell tumor or a hematopoietic malignancy.

In another aspect, provided herein is a method for increasing sensitivity of a MIC-positive tumor to immune cell-mediated killing, the method comprising administering to an individual having a MIC-positive tumor, a therapeutically effective amount of an agent that binds a region in the alpha-3 ectodomain of a MIC polypeptide, whereby the MIC-positive tumor is rendered more sensitive to immune cell-mediated killing.

In one embodiment of this aspect, the agent inhibits shedding of said MIC polypeptide, or a fragment thereof.

In another embodiment of this aspect, the agent is selected from the group consisting of an antibody or a polypeptide comprising an antigen-binding fragment thereof, a peptide, an aptamer, and a small molecule.

In another embodiment of this aspect, the agent binds a region comprising the amino acid sequence NGTYQT (SEQ ID NO: 1). In another embodiment of this aspect, the agent physically contacts at least one amino acid of the amino acid sequence NGTYQT (SEQ ID NO: 1) comprised by the α3 ectodomain of a MIC polypeptide.

In another embodiment of this aspect, the agent inhibits the interaction of the MIC polypeptide with ERp5 polypeptide.

In another embodiment of this aspect, the tumor comprises an epithelial cell tumor or a hematopoietic malignancy.

In another aspect, provided herein is a method for reducing MIC shedding by a cancer cell, the method comprising contacting a MIC-positive cancer cell with an agent that binds a region in the alpha-3 ectodomain of a MIC polypeptide, wherein the agent inhibits shedding of said MIC polypeptide, or a fragment thereof.

In one embodiment of this aspect, the agent is selected from the group consisting of an antibody or a polypeptide comprising an antigen-binding fragment thereof, a peptide, an aptamer, and a small molecule.

In another embodiment of this aspect, the agent binds a region comprising the amino acid sequence NGTYQT (SEQ ID NO: 1). In another embodiment of this aspect, the agent physically contacts at least one amino acid of the amino acid sequence NGTYQT (SEQ ID NO: 1) comprised by the α3 ectodomain of a MIC polypeptide.

In another embodiment of this aspect, the agent inhibits the interaction of a MIC polypeptide with ERp5 polypeptide.

In another embodiment of this aspect, the cancer comprises an epithelial cell tumor or a hematopoietic malignancy.

In another aspect, provided herein is a method for inhibiting tumor formation in an individual, the method comprising administering to an individual a therapeutically effective amount of an agent that binds a region in the alpha-3 ectodomain of a MIC polypeptide.

In one embodiment of this aspect, the agent inhibits shedding of said MIC polypeptide, or a fragment thereof.

In another embodiment of this aspect, the agent is selected from the group consisting of an antibody or a polypeptide comprising an antigen-binding fragment thereof, a peptide, an aptamer, and a small molecule.

In another embodiment of this aspect, the agent binds a region comprising the amino acid sequence NGTYQT (SEQ ID NO: 1). In another embodiment of this aspect, the agent physically contacts at least one amino acid of the amino acid sequence NGTYQT (SEQ ID NO: 1) comprised by the α3 ectodomain of a MIC polypeptide.

In another embodiment of this aspect, the agent inhibits the interaction of a MIC polypeptide with ERp5 polypeptide.

In another aspect, provided herein is a method for screening for an agent that inhibits MIC shedding, the method comprising: (a) expressing a polypeptide construct in a tumor cell, the construct comprising a first and second polypeptide moiety, linked by a heterologous polypeptide comprising MIC structure or sequence necessary for MIC shedding; (b) contacting the tumor cell with an agent; and (c) detecting cleavage of the polypeptide construct that separates the first and second polypeptide moieties, wherein decreased cleavage indicates the agent is an inhibitor of MIC shedding. Structures and sequences necessary for MIC shedding are described herein, and include, but are not limited to the sequences NGTYQT (SEQ ID NO: 1) and YQTWVATR (SEQ ID NO: 2), preferably in the context of the larger sequence TQQWGDVLPDGNGTYQTWVATR (SEQ ID NO: 3) and more preferably in the context of sequence identified in FIG. 7b as critical for shedding, up to and including the whole α3 domain of MIC as indicated in FIG. 7b. Any of these amino acid sequences can be targeted for the inhibition of MIC shedding by methods as described herein.

In one embodiment of this aspect, first and second polypeptide moieties comprise a FRET donor/acceptor pair. In another embodiment of this aspect, the first and second polypeptide moieties comprise a modular enzyme. In another embodiment of this aspect, the first and second polypeptide moieties can be detected by antibody reagents directed to each separate moiety.

In another aspect, provided herein is an antibody or antigen-binding fragment thereof that specifically binds a structural determinant of a MIC polypeptide required for MIC shedding. In one embodiment of this aspect, the antibody or antigen-binding fragment thereof specifically binds a polypeptide comprising the amino acid sequence NGTYQT (SEQ ID NO: 1), the sequence YQTWVATR (SEQ ID NO: 2), the sequence TQQWGDVLPDGNGTYQTWVATR (SEQ ID NO: 3), alone or, for example, in the context of the sequence identified by arrowheads in FIG. 7b. Any of these sequences can be therapeutically targeted to inhibit MIC shedding and thereby inhibit tumor growth. The 8 amino acid motif "YQTWVATR" (SEQ ID NO: 2) is also important for shedding—while not wishing to be bound by theory, it is thought that this sequence may sustain or stabilize the conformation of MIC necessary for contact with ERp5.

An antibody or antigen-binding fragment of this aspect will bind a MIC polypeptide within the region necessary for MIC shedding and will inhibit the cleavage of the MIC polypeptide that is normally involved in shedding. The inhibition by antibody or antigen-binding fragment thereof preferably will not substantially interfere with the cleavage of non-MIC polypeptide targets for the cleavage enzyme(s).

In another embodiment, provided herein is an antibody or antigen-binding fragment thereof that specifically binds the amino acid sequence NGTYQT (SEQ ID NO: 1) alone or in the context of a larger polypeptide, and that inhibits the interaction of a MIC polypeptide with an ERp5 polypeptide.

In another aspect, provided herein is a MIC fusion reporter construct composition, comprising a fusion polypeptide comprising a donor fluorescent polypeptide moiety, and an acceptor fluorescent polypeptide moiety, linked by amino acid sequence or structure necessary for the cleavage of MIC involved in MIC shedding, wherein said donor moiety upon excitation emits energy within the excitation range of said acceptor moiety.

In one embodiment of this aspect, the acceptor moiety comprises a quencher. In another embodiment of this aspect, the acceptor moiety comprises a fluorophore.

DEFINITIONS

As used herein, the term "increasing sensitivity" refers to the ability of an agent to prevent MIC shedding by a tumor cell, such that the tumor cell is more susceptible to immune cell mediated killing by the innate immune system than in the absence of the agent, with the result being an increase in host rejection of a tumor. By "increased sensitivity" is meant a reduction in MIC shedding of at least 10% as measured using an in vitro cell shedding assay e.g., as described herein in the Example section; preferably at least a 20% decrease, at least 30%, at least 40%, at least 50%, at least 60%, at least 70%, at least 80%, at least 90%, at least 95%, at least 99%, or even 100% (i.e., no measurable shedding) decrease in MIC shedding as assessed using an in vitro cell shedding assay.

As used herein the term "immune cell-mediated killing" refers to the rejection of a tumor cell by activation of natural killer cells (NK cells) and/or CD8 T cells, which results in death of a tumor cell by apoptosis or necrosis. The term "immune cell-mediated killing" indicates that the agent used for treatment need not be cytotoxic or anti-angiogenic directly on a tumor cell, but rather that the agent as that term is used herein, instead increases the susceptibility of the tumor cell to be rejected by the host's own innate immune system. Thus, the term "immune cell-mediated killing" encompasses any host immune response that initiates tumor rejection by promoting a cell death process, such as apoptosis or necrosis.

The term "cancer" as used herein is defined as a new growth of tissue comprising uncontrolled and progressive multiplication. The term "tumor" or "tumor cell" used interchangeably herein refers to the tissue mass or tissue type or cell type that is undergoing uncontrolled proliferation.

As used herein the term "agent" refers to any organic or inorganic molecule, including but not limited to, modified and unmodified nucleic acids such as antisense nucleic acids, RNAi agents such as siRNA or shRNA, peptides, peptidomimetics, aptamers, small molecules, and antibodies.

As used herein, the term "therapeutically effective amount" refers to the amount of an agent that is effective, at dosages and for periods of time necessary to achieve the desired therapeutic result, e.g., a diminishment or prevention of MIC shedding. A therapeutically effective amount of the inhibitors described herein, or functional derivatives thereof, may vary according to factors such as disease state, age, sex, and weight of the subject, and the ability of the therapeutic compound to elicit a desired response in the subject. The effective amount of a given therapeutic agent will also vary with factors such as the nature of the agent, the route of administration, the size and species of the mammal to receive the therapeutic agent, and the purpose of the administration. A therapeutically effective amount is also one in which any toxic or detrimental effects of the therapeutic agent are outweighed by the therapeutically beneficial effects. The effective amount in each individual case may be determined empirically by a skilled artisan according to established methods in the art. In general, an inhibitor is determined to be "therapeutically effective" in the methods described herein if (a) measurable symptom(s) of, for example, tumor size or growth rate are reduced, for example by at least 10% compared to the measurement prior to treatment onset, (b) the progression of the disease is halted (e.g., patients do not worsen or the tumor does not continue to grow, or (c) symptoms are reduced or even ameliorated, for example, by measuring a reduction in tumor size or growth rate. Thus, while a cure for a given cancer would certainly be desirable, "effective treatment" as the term is used herein requires only an amelioration of tumor size or growth rate. As a non-limiting example, a reduction in the rate of tumor growth by at least 10% can constitute effective treatment. Slowing the growth of a tumor, even without necessarily stopping such growth can have benefits to the patient, and can, for example, render the tumor more susceptible to other modes of attack. Efficacy of treatment can be judged by an ordinarily skilled practitioner. Efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a cessation or slowing of the rate of growth of the tumor indicates effective treatment.

As used herein, the phrase "region in the alpha-3 ectodomain of MIC" comprises at least the amino acid sequence NGTYQT (SEQ ID NO: 1) sequence necessary for MIC interaction with ERp5 polypeptide. The term refers generally to that region that is necessary for shedding of MIC from a tumor cell. In one embodiment, the region that is necessary for MIC shedding comprises or alternatively, consists essentially of, the amino acid sequence TQQWGDVLP-DGNGTYQTWVATR (SEQ ID NO: 3). In another embodiment, the region that is necessary for MIC shedding comprises, or alternatively, consists essentially of, the amino acid sequence NGTYQT (SEQ ID NO: 1). In another embodiment, the region comprises the amino acid sequence QTWVATR (SEQ ID NO: 4), YQTWVATR (SEQ ID NO: 2) or TWVA (SEQ ID NO: 5).

As used herein, the term "MIC peptide cleavage site" refers to a sequence of the alpha-3 ectodomain of a MIC polypeptide that is sufficient to direct cleavage in an ERp5-dependent manner. At a minimum, while the peptide is not necessarily cleaved at the amino acid sequence NGTYQT (SEQ ID NO: 1), a MIC peptide cleavage site peptide will comprise an NGTYQT (SEQ ID NO: 1) sequence, e.g., in the context of a larger peptide, e.g., a peptide comprising sequence identified as critical for MIC shedding in FIG. 7b.

As used herein, the term "MIC-positive tumor" is used to describe a tumor cell, a cluster of tumor cells or a tumor mass, which produces a MIC protein. This term is intended to encompass all tumor cells and/or tumor masses that shed all or part of a MIC protein, thus these cells may only display a MIC protein on it surface for a short time period—that is, the term encompasses tumors that shed MIC protein, regardless of whether detectable MIC protein remains present on their cell surface or not. However, any tumor that is capable of escaping innate immune rejection by shedding MIC is considered to be a "MIC-positive tumor" as that term is used herein. Some non-limiting examples of MIC-positive tumors include epithelial cell tumors and hematopoietic malignancies.

As used herein, the term "ERp5 polypeptide" refers to a protein disulfide isomerase enzyme, endoplasmic reticulum protein 5, that specifically interacts with MIC polypeptides and is involved in MIC shedding. In one embodiment the ERp5 polypeptide is a human ERp5 polypeptide, e.g., the polypeptide described at GenBank Accession No. NP 005733. The amino acid sequence of the human ERp5 polypeptide is as follows (SEQ ID NO: 6):

```
  1 mallvlglvs ctfflavngl ysssddviel tpsnfnrevi qsdslwlvef yapwcghcqr
 61 ltpewkkaat alkdvvkvga vdadkhhslg gqygvqgfpt ikifgsnknr pedyqggrtg
121 eaivdaalsa lrqlvkdrlg grsggyssgk qgrsdssskk dvieltddsf dknvldsedv
181 wmvefyapwc ghcknlepew aaaasevkeq tkgkvklaav datvnqvlas rygirgfpti
241 kifqkgespv dydggrtrsd ivsraldlfs dnapppelle iinediakrt ceehqlcvva
301 vlphildtga agrnsylevl lkladkykkk mwgwlwteag aqseletalg iggfgypama
361 ainarkmkfa llkgsfseqg ineflrelsf grgstapvgg gafptivere pwdgrdgelp
421 veddidlsdv elddlgkdel
```

As used herein, the term "inhibiting tumor formation" refers to an action of an agent that permits immune cell-mediated killing of single tumor cells or small clusters of cells, such that a tumor is not able to amass and/or grow in size. This is particularly useful for preventing or reducing the likelihood of cancer metastases from occurring by treating tumor cells prior to the formation of a detectable metastatic tumor mass. In one embodiment, the agent can be used prophylactically to inhibit tumor formation in a person having an increased risk of cancer (e.g., family history, previous cancer history, etc).

As used herein, the phrase "specifically binds" refers to binding of, for example, an antibody or antigen-binding fragment thereof to an epitope or antigen or antigenic determinant in such a manner that binding can be displaced or competed with a second preparation of identical or similar epitope, antigen or antigenic determinant.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

BRIEF DESCRIPTION OF THE FIGURES

FIG. 1 shows the MICB cleaved site(s) in TC2 cells.

FIG. 2 shows construction and expression of shedding-resistant non-cleavable and soluble recombinant forms of MICB (rsMICB) in TC2 cell lines. FIG. 2c shows that MICB.A2 is shedding-resistant. The top graph shows an amount of shed soluble MICB in the culture supernatant and MICB in the cell lysates. $4\times10^5$ cells/well were plated on a 6-well plate overnight. Media were removed and replaced with 1 ml of serum-free media. 6 hrs later, Media were collected and filtered. Cells were lysed with 1 ml lysis buffer. 50 ul of culture supernatant and cell lysates were used for (s) MICB ELISA assay. The bottom graph represents the degree of shedding as calculated by molar concentration of soluble MICB in the supernatant vs. total molar concentration of soluble MICB and MICB (a sum of supernatant and cell lysates). The final results were normalized by cell numbers at the time of the assay. Results represent three independent experiments. *, P<0.001.

FIG. 3 shows the overexpression of MICB and MICB.A2 increases the sensitivity of TC2 cells to NK cell killing.

FIG. 4 shows that expression of MICB.A2 but not the cleavable MICB prevents tumor formation in vivo. Six animals were used in each group. Tumor growth was monitored twice weekly. Tumor volume was estimated by the formula Volume=L2×W/2.

FIG. 5 shows that shedding of MICB by TC2-MICB cells compromises NK cell activity in vivo.

FIG. 6 shows that soluble MICB induced NK cell dysfunction.

FIG. 7 shows patterns of MIC shedding. FIG. 7b shows a partial (SEQ ID NO: 7) of the MICA sequence and the region (gray area) in the α3 domain that is critical for shedding. The gray area was replaced with corresponding sequence of HLA.A2 to generate mutant MICA.A2. Box region, near-transmembrane region (stalk region). Asterisks indicate the two residues (C202 and C259) that form a disulphite bond. Arrows indicate beginning and end of the α3 domain. FIG. 7c depicts a histogram of flow cytometry showing surface expression of MICA and MICA.A2 (filled profiles) in TRAMP-C2 cells. Cells were stained with mAb 6D4.6 followed by a PE-conjugated secondary reagent. Open profiles, negative control TRAMP-C2 cells were stained with 6D4.6. FIG. 7d depicts an ELISA assay quantitatively showing that TRAMP-C2 cells shed MICA, not MICA.A2. Cells were seeded at the density of 4×10$^5$ cells/well in a 6-well plate in complete media overnight and replaced with 1 ml/well serum-free media for 24 hrs. Supernatant was collected and filtered through 0.45 µm membrane. Cells were lysed with 1 ml lysis buffer. Amount of soluble MICA in the supernatant and MICA in the cell lysates was measured using human MICA DuoSet sandwich ELISA kit (R&D Systems). The degree of shedding is expressed as the ratio of sMICA in the supernatant (SN) to MICA in the lysates (LY). Results represent three independent experiments.

FIG. 8 shows motif(s) in the α3 domain of MICA are identified as shedding-sensitive by mutational analyses. FIG. 8a shows the sequence and designation of MICA mutants (SEQ ID NOs 8 to 21). The shedding assay results (from FIG. 3) are also indicated. +, shedding. –, non-shedding. wtMICA, wild-type MICA.

FIG. 9 shows the conserved shedding-sensitive motifs in C1R cells.

FIG. 10 shows the results of mass spectrometry analyses of sdMICA. FIG. 10a shows the results of mass spectrometry analyses of in-gel trypsin digests of sdMICA and control rsMICA (SEQ ID NOs 22 to 25). One peptide (marked with asterisks) with non-tryptic C-terminus was identified in sdMICA samples, but not in control rsMICA samples. sdMICA were purified from the culture supernatant of TRAMP-C2 or C1R cells with the mAb 6D4.6 and deglycosylated with PNGaseF before being digested in-gel with trypsin. The results are consistent in TRAMP-C2 and C1R cells. **, sdMICA-specific non-tryptic peptides, suggesting potential MICA cleavage site(s) resulted from tumor shedding. FIG. 10b shows results of mass spectrometry analyses of GluC digests of sdMICA (top, sequence is SEQ ID NO: 26) and control rsMICA (Bottom, sequence is SEQ ID NO: 26). Ragged C-termini were identified in the alpha-3 domain and the near-transmembrane region in both sdMICA and control rsMICA. Arrows indicate C-termini that were generated not due to Glu-C digestion, but by shedding. sdMICA from TRAMP-C2-MICA cells and C1R-MICA cells produced identical results.

FIG. 11 shows that mutations in the near-transmembrane region of MICA do not prevent shedding.

FIG. 12 depicts a cytotoxicity assay showing susceptibility of cells expressing shedding-resistant MICA to NK cell killing. A standard 4-h 51Cr release assay was performed. NK-92 cells are used as effectors. Pure populations of M5 or M7-expressing C1R and TRAMP-C2 cells were isolated by flow cytometry sorting and are used as target cells.

FIG. 13a shows a partial of the MICA sequence in the α3 domain (SEQ ID NO: 7). Residues in the gray area were selected for mutation analyses. Arrows indicate beginning and end of the α3 domain. Residues in the boxed region were identified to be critical for MICA shedding. Asterisks indicate the two Cysteine residues that form a disulphide bond. FIG. 13b shows the sequence and designation of MICA mutants (SEQ ID NOs 8 to 15, and 20). The underlined sequences were mutated. The shedding assay results (from FIG. 14) are also indicated. +, shedding. –, no shedding. wtMICA, wild type MICA.

FIG. 14 shows that mutation of an 6-aa motif prevents MICA shedding.

FIG. 15 shows that the 6-aa motif is critical for MICA to interact with ERp5. FIG. 15a depicts the results of mass spectrometry analyses showing that no shedding cleavage site was identified within or near the 6-aa motif. The sequence shown is SEQ ID NO: 26. Arrows indicate non-tryptic C-terminus, presumably generated by shedding, in the extracellular domain of MICA. FIGS. 15b-d show that mutation in the 6-aa prevents complex formation of MICA with ERp5. TRAMP-C2 cells expressing wtMICA (Lane 1) and MICA mutant M5 (lane 2) were surface biotinylated and lysed in 1% NP-40 lysis buffer. Cell lysates were immunoprecipitated with the anti-MIC mAb 6D4.6. The immunocomplexes were resolved on SDS-PAGE and immunoblotted with HRP-Streptavidin (FIG. 15b), or the polyclonal anti-MIC Ab H-300 (FIG. 15c), or the polyclonal anti-ERp5 Ab11432 (FIG. 15d).

FIG. 16 shows that mutation of the 6-aa motif does not interfere with recognition of MICA by NKG2D. FIG. 16b depicts a cytotoxicity assay showing comparable susceptibility of cells expressing shedding-resistant MICA and wtMICA to NK cell killing. E:T, effector:Target. Data also show that specific lysis was blocked by pre-incubating effector NK-92 cells with 30 ng/ml of rsMICA. Data represents three independent experiments.

FIG. 19 depicts MICB alleles (SEQ ID NOs 89 to 111). The sequences and alignment were extracted from Bahram et al., "MIC and Other NKG2D Ligands: From None to Too Many," Curr Opin Immunol 17:505-9 (2005), which is hereby incorporated by reference in its entirety. The 11-aa shedding-motif is bold and boxed.

FIG. 20 shows the time course of MICA shedding by tumor cells. FIG. 20a depicts Western-blots showing accumulation of sMICA in the culture. Top, shedding-derived soluble MICA (sdMICA) in the supernatant (SN). Bottom, MICA in the cell lysates (LY). FIG. 20b depicts an ELISA assay quantitatively showing accumulation of sMICA in the culture supernatant (SN) and reduction of MICA in the cell lysates (LY). FIG. 20C shows the calculated degree of shedding of MICA. In the ELISA assay, cells were plated in complete media overnight. The next day, media were removed, cells were washed and serum-free media were added to the culture. Supernatant and cell lysates were collected at indicated time. Note that there is no significant accumulation of high levels of sMICA in the supernatant before 6 h of culture.

DETAILED DESCRIPTION OF THE INVENTION

Figure 1A:
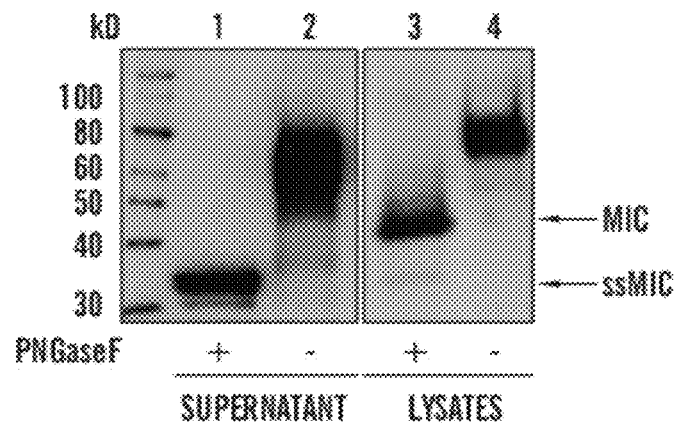
FIG. 1a depicts a Western-blot showing the predicted size of cleaved soluble MICB in TC2 cells. Supernatant and lysates of TC2-MICB cells were immunoprecipitated with anti-MIC mAb 6D4.6. The immune complexes were treated with PNGase F and resolved on SDS-PAGE. Proteins were transferred to nitrocellulose membrane and blotted with goat anti-MICB polyclonal Ab. Lane 1 and 2, detection of sMICB from TC2-MICB supernatant. The molecular mass of the deglycosylated cleaved sMICB is estimated to be 31-33 kDa. Lanes 3 and 4 indicate detection of full-length MICB from TC2-MICB cell lysates. The full-length deglycosylated MICB is estimated to be 41 kDa on 4-15% SDS-PAGE.

Clinical data indicate that MIC shedding from tumor cells is associated with tumor progression, and has prompted the investigation herein of whether tumor shedding of MIC is the mechanism by which MIC-positive tumors evade NK cell immune surveillance and progress in cancer patients.

As described in the Examples section herein below, MIC peptide sequences critical for MIC shedding have been discovered. Interference with MIC shedding by targeting the identified site(s) can be used to enhance the sensitivity, or susceptibility of a tumor cell to immune clearance. Accordingly, described herein are methods for treating cancer by inhibiting MIC shedding involving cleavage at a site in the alpha-3 ectodomain of MIC, and thereby enhancing a tumor cell's sensitivity to immune cell-mediated killing. Also described herein is a screening assay useful for testing a candidate agent for efficacy in inhibiting MIC shedding within the alpha-3 ectodomain of MIC.

In Vitro Shedding Assay

Described herein is an in vitro cell-based MIC shedding assay that can be used for screening inhibitors of MIC shedding within a region of the alpha-3 ectodomain of MIC. For the purpose of screening for an agent that prevents MIC shedding, a polypeptide fusion construct is expressed in a cell. The polypeptide fusion construct comprises MIC structure or sequence necessary for MIC shedding, fused to a heterologous polypeptide or polypeptides, e.g., flanked on either end by a first and second polypeptide moiety. Cells expressing this fusion construct are then treated in the presence or absence of a candidate agent, and assessed for a detectable signal such as e.g., fluorescence, enzyme product, or chemiluminescence etc. The first and second polypeptide moiety provide a detectable signal that is dependent on their spatial interaction. For example, a signal is produced only when the MIC peptide is cleaved, liberating the two polypeptide moieties or vice versa.

Structures and sequences necessary for MIC shedding are described herein, and include, but are not limited to the sequences NGTYQT (SEQ ID NO: 1) and YQTWVATR (SEQ ID NO: 2), preferably in the context of the larger sequence TQQWGDVLPDGNGTYQTWVATR (SEQ ID NO: 3) and more preferably in the context of sequence identified in FIG. 7b as critical for shedding, up to and including the whole α3 domain of MIC as indicated in FIG. 7b.

In one embodiment, the first and second polypeptide moiety when fused on either end of the MIC target peptide are unable to produce a detectable signal (e.g., fluorescence), thus only shed or cleaved MIC peptides produce a detectable signal. In this arrangement, however, when cells are cultured in the presence of an agent capable of inhibiting MIC shedding, the detectable signal is not generated, while cells with a detectable signal indicate MIC shedding. To be clear, in this embodiment the detectable signal is turned 'off' by an agent that inhibits shedding.

Alternatively, in another embodiment the fusion polypeptide produces a detectable signal, until separation of the two polypeptide moieties due to MIC shedding prevents further detection. In this alternate embodiment, cells with a detectable signal indicate that an agent prevents MIC shedding. Thus, an agent capable of inhibiting MIC shedding keeps or turns 'on' the detectable signal.

The first and second polypeptide moieties can comprise, for example, a FRET donor/acceptor pair, a modular enzyme or distinct antibody binding epitopes for immunoassay detection (see descriptions below for more detail). Methods for detecting intracellular polypeptide interactions are described in e.g., U.S. Pat. Nos. 7,413,862; 6,936,428, and 6,972,198, which are incorporated herein by reference in their entirety. Quantification of a detectable signal can be achieved, for example by FACS analysis.

FRET

In FRET, a fluorophore (called a "donor") transfers, after excitation by a light source, its energy to another fluorophore (called "acceptor"). The energy transfer occurs when the emission spectrum of the donor fluorophore overlaps significantly with the excitation spectrum of the acceptor. Sufficiently close juxtaposition of the two fluorophores, generally closer than 100 angstroms, but preferably closer than 50 angstroms, is essential for energy transfer between the donor/acceptor pair. FRET is usually based on the interaction between donor and acceptor fluorophores that are both fluorescent. However, FRET can also be detected by the quenching of donor fluorescence using a nonfluorescent acceptor fluorophore. Nonfluorescent acceptor fluorophores are in general advantageous because they eliminate the background fluorescence that results from direct acceptor excitation. For the methods described herein, it is possible to monitor juxtaposed probes on interacting molecules using a fluorescent donor fluorophore and a nonfluorescent acceptor fluorophore.

Specific binding of a set of probes to non-interacting molecules will give a basal fluorescence signal. Upon close interaction of the molecules, FRET between the probes will quench the donor fluorescence. Rather than measuring an increase in acceptor fluorescence, use of a nonfluorescent acceptor involves measuring a decrease in donor fluorescence. Generally, detection of a decreased signal is less sensitive compared to detection of an increased signal. Therefore, a method according to the invention is preferably practiced using a fluorescent donor and a fluorescent acceptor fluorophore.

Modular Enzyme

As used herein, the term "modular enzyme" refers to an assembly of enzyme subunits or enzymes that carry between them, a set of separate active sites for non-iteratively carrying out each step of an enzymatic reaction. (e.g., see Cortes et al., "An Unusually Large Multifunctional Polypeptide in the Erythromycin-producing Polyketide Synthase of *Saccharopolyspora erythraea,*" *Nature* 348:176 (1990); Donadio et al., "Modular Organization of Genes Required for Complex Polyketide Biosynthesis," *Science* 252:675 (1991); MacNeil et al., "Complex Organization of the *Streptomyces avermitilis* Genes Encoding the Avermectin Polyketide Synthase," *Gene* 115:119 (1992), which are incorporated herein by reference in their entirety). Thus, a modular enzyme activity is also dependent on the spatial relationship of the subunits or enzymes involved. For example, in one embodiment a modular enzyme when separated by an uncleaved MIC peptide has no enzymatic activity, thus agents that inhibit shedding of MIC would prevent detection of the enzymatic product. Upon MIC shedding, the two subunits or enzymes can interact to produce a detectable product. Alternatively, in another embodiment the enzyme has enzyme activity only when bound by the MIC peptide and disruption (i.e., cleavage) of the peptide results in a loss of enzyme activity. Non-limiting examples of modular enzymes include neuronal nitric oxide synthase, PKS enzymes in *streptomyces*, non-ribosomal peptide synthetases, a NRPS enzyme system, polyketide synthases or receptors with a modular structure.

Immunoassay Detection

As used herein, the term "ELISA" refers to an enzyme-linked immunosorbent assay. Numerous methods and applications for carrying out an ELISA are well known in the art, and provided in many sources (See, e.g., Crowther, "Enzyme-Linked Immunosorbent Assay (ELISA)," in Molecular Biomethods Handbook, Rapley et al. [eds.], pp. 595 617, Humana Press, Inc., Totowa, N.J. [1998]; Harlow and Lane (eds.), Antibodies: A Laboratory Manual, Cold Spring Harbor Laboratory Press (1988); and Ausubel et al. (eds.), Current Protocols in Molecular Biology, Ch. 11, John Wiley & Sons, Inc., New York (1994), which are incorporated herein by reference in their entirety).

In one embodiment, a "direct ELISA" protocol is provided, where an antigen is first bound and immobilized to a microtiter plate well. In an alternative embodiment, a "sandwich ELISA" is provided, where the antigen is attached to the stationary phase by capturing it with an antibody that has been previously bound to the microtiter plate well. The ELISA method detects an immobilized antigen by use of an antibody-enzyme conjugate, where the antibody is specific for the antigen of interest, and the enzyme portion allows visualization and quantitation by the generation of a colored or fluorescent reaction product. The conjugated enzymes commonly used in the ELISA include horseradish peroxidase, urease, alkaline phosphatase, glucoamylase or β-galactosidase. The intensity of color development is proportional to the amount of antigen present in the reaction well.

Agents

Essentially any agent that inhibits MIC shedding by e.g., blocking a MIC cleavage site from proteolytic cleavage can be used with the methods described herein. Some non-limiting examples of anti-MIC shedding agents include antibodies, small molecules, RNA interference molecules, aptamers, drugs, vitamins, receptors, ligands, peptides, nucleic acids, or a combination thereof.

Antibodies

Antibodies can be used to inhibit MIC shedding by e.g., recognition of an epitope such that a bound antibody shields a MIC shedding cleavage site or conformation required for protease-mediated cleavage. The production of non-human monoclonal antibodies, e.g., murine or rat, can be accomplished by, for example, immunizing the animal with an immunogenic peptide of the alpha-3 ectodomain of MIC (e.g., See Harlow & Lane, Antibodies, A Laboratory Manual (CSHP NY, 1988, which is herein incorporated by reference in its entirety). Such an immunogen can be obtained, for example, from a natural source, by peptide synthesis or by recombinant expression. Humanized forms of mouse antibodies can be generated by linking the CDR regions of murine or other non-human antibodies to human constant regions by recombinant DNA techniques. See Queen et al., *Proc Natl Acad Sci USA* 86:10029-10033 (1989) and WO 90/07861 (incorporated by reference herein in their entirety). Human antibodies can be obtained using phage-display methods. See, e.g., Dower et al., WO 91/17271; McCafferty et al., WO 92/01047, which are incorporated herein by reference in their entirety. In these methods, libraries of phage are produced in which members display different antibodies on their outer surfaces. Antibodies are usually displayed as Fv or Fab fragments. Phage displaying antibodies with a desired specificity are selected by binding to a region of the alpha-3 ectodomain of MIC or fragments thereof. Increased affinity can be selected by successive rounds to affinity enrichment by binding to the same fragment. Human antibodies against a region of the alpha-3 ectodomain of MIC can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991) (each of which is incorporated by reference in its entirety). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using a region of the alpha-3 ectodomain of MIC, as an affinity reagent. Human or humanized antibodies can be designed to have IgG, IgD, IgA and IgE constant region, and any isotype, including IgG1, IgG2, IgG3 and IgG4. Antibodies can be expressed as tetramers containing two light and two heavy chains, as separate heavy chains, light chains, as single variable domains (dAbs), e.g., $V_H$ or $V_L$, as Fab, Fab'F(ab')2, and Fv, or as single chain antibodies in which heavy and light chain variable domains are linked through a spacer.

Production of Non-Human Antibodies

The production of non-human monoclonal antibodies, e.g., murine, guinea pig, rabbit or rat, can be accomplished by, for example, immunizing the animal with an immunogenic peptide of the alpha-3 ectodomain of MIC, for example but not limited to a peptide with amino acid sequence TQQWGDVLPDGNGTYQTWVATR (SEQ ID NO: 3), NGTYQT (SEQ ID NO: 1), or YQTWVATR (SEQ ID NO: 2) for example. Any immunogenic peptide substantially similar to a region of the alpha-3 ectodomain is encompassed for use, for example immunogenic peptides substantially similar to e.g. TQQWGDVLPDGNGTYQTWVATR (SEQ ID NO: 3) or a portion thereof, e.g., a portion comprising or consisting essentially of NGTYQT (SEQ ID NO: 1) can be used. See e.g., Harlow Lane, Antibodies, A Laboratory Manual (CSHP NY, 1988); herein incorporated by reference in its entirety. Such immunogenic peptides can be obtained, e.g., from a natural source, by peptide synthesis or by recombinant expression. Optionally, immunogenic peptides can be administered fused or otherwise complexed with a carrier protein, as described herein and known in the art. Optionally, immunogenic peptides can be administered with an adjuvant. Several types of adjuvant can be used as described herein. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to the immunogen. Optionally, antibodies are further screened for binding to a specific region of the immunogen, for example the alpha-3 ectodomain of MIC or a portion comprising or consisting essentially of the sequence NGTYQT (SEQ ID NO: 1). Binding can be assessed, for example, by Western blot or ELISA. The smallest fragment to show specific binding to the antibody defines the epitope of the antibody. Alternatively, epitope specificity can be determined by a competition assay in which a test and reference antibody compete for binding to the component. If the test and reference antibodies compete, then they bind to the same epitope or epitopes sufficiently proximal that binding of one antibody interferes with binding of the other.

Chimeric and Humanized Antibodies

Chimeric and humanized antibodies having the same or similar binding specificity and affinity as a mouse or other nonhuman antibody provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions substantially from a mouse-antibody, (referred to as the donor immunoglobulin). See, Queen et al., *Proc Natl Acad Sci USA* 86:10029-10033 (1989) and WO 90/07861, U.S. Pat. No. 5,693,762, U.S. Pat. No. 5,693,761, U.S. Pat. No. 5,585,089, U.S. Pat. No. 5,530, 101 and Winter, U.S. Pat. No. 5,225,539, which are herein incorporated by reference in their entirety. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies. See Carter et al., WO 92/22653, which is herein incorporated by reference in its entirety.

Human Antibodies

Human antibodies against the alpha-3 ectodomain of MIC are provided by a variety of techniques described below. Some human antibodies are selected by competitive binding experiments, or otherwise, to have the same epitope specificity as a particular mouse antibody. (1) Trioma Methodology: The basic approach and an exemplary cell fusion partner, SPAZ-4, for use in this approach have been described by Ostberg et al., "Human X (Mouse X Human) Hybridomas Stably Producing Human Antibodies," *Hybridoma* 2:361-367 (1983); Oestberg, U.S. Pat. No. 4,634,664; and Engleman et al., U.S. Pat. No. 4,634,666 (each of which is incorporated by reference in its entirety). The antibody-producing cell lines obtained by this method are called triomas, because they are descended from three cells—two human and one mouse. Initially, a mouse multiple myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibodies more stably than ordinary hybridomas made from human cells. The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with the immunogenic peptides described herein, e.g., a region of the alpha-3 ectodomain of MIC. In some methods, B cells are isolated from the same patient who is ultimately to be administered antibody therapy. Although triomas are genetically stable they do not produce antibodies at very high levels. Expression levels can be increased by cloning antibody genes from the trioma into one or more expression vectors, and transforming the vector into standard mammalian, bacterial or yeast cell lines, according to methods well known in the art.

(2) Transgenic Non-Human Mammals. Human antibodies against MIC peptide can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin peptide component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625, 126, U.S. Pat. No. 5,569,825, U.S. Pat. No. 5,545,806, *Nature* 148, 1547-1553 (1994), Neuberger et al., "Generating Highavidity Human Mabs in Mice," *Nature Biotechnology* 14, 826 (1996), Kucherlapati, WO 91/10741 (1991) (each of which is incorporated by reference in its entirety). Transgenic mice are particularly suitable in this regard. Monoclonal antibodies are prepared by, e.g., fusing B-cells from such mammals to suitable multiple myeloma cell lines using conventional KohlerMilstein technology. Human polyclonal antibodies can also be provided in the form of serum from humans immunized with an immunogenic agent.

(3) Phage Display Methods. A further approach for obtaining MIC peptide-specific antibodies, for example antibodies that bind alpha-3 ectodomain sequences is to screen a DNA library from human B cells according to the general protocol outlined by Huse et al., "Generation of a Large Combinatorial Library of the Immunoglobulin Repertoire in Phage Lambda," *Science* 246:1275-1281 (1989), which is herein incorporated by reference in its entirety. For example, as described for trioma methodology, such B cells can be obtained from a human immunized with the MIC peptides described herein, for example a peptide comprising the amino acid sequence YQTWVATR (SEQ ID NO: 2) or NGTYQT (SEQ ID NO: 1). Optionally, such B cells are obtained from a patient who is ultimately to receive antibody treatment. Antibodies binding to an epitope of the MIC peptide, for example those binding to a peptide comprising a region of the alpha-3 ectodomain of MIC are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332 (each of which is incorporated by reference in its entirety). In these methods, libraries of phage are produced in which members display different antibodies on their outer surfaces. Antibodies are usually displayed as Fv or Fab fragments. Phage displaying antibodies with a desired specificity are selected by affinity enrichment to a MIC peptide, in particular peptides with a region of the alpha-3 ectodomain of MIC, e.g., the amino acid sequence NGTYQT (SEQ ID NO: 1) or YQTWVATR (SEQ ID NO: 2).

Antibodies can be expressed as tetramers containing two light and two heavy chains, as separate heavy chains, light chains, as Fab, Fab F(ab)$_2$, and Fv, or as single chain antibodies in which heavy and light chain variable domains are linked through a spacer. Antibodies can also be single domain antibodies, or dAbs.

Expression of Recombinant Antibodies

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Mammalian cells are a preferred host for expressing nucleotide segments encoding immunoglobulins or fragments thereof. See Winnacker, From Genes to Clones, (VCH Publishers, NY, 1987), which is incorporated herein by reference in its entirety. A number of suitable host cell lines capable of secreting intact heterologous proteins have been developed in the art, and include CHO cell lines, various COS cell lines, HeLa cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," *Immunol Rev* 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. See Co et al., "Chimeric and Humanized Antibodies with Specificity for the CD33 Antigen," *J Immunol* 148:1149 (1992), which is incorporated herein by reference in its entirety. Alternatively, antibody coding sequences can be incorporated in transgenes for introduction into the genome of a transgenic animal and subsequent expression in the milk of the transgenic animal (e.g., according to methods described in U.S. Pat. No. 5,741,957, U.S. Pat. No. 5,304,489, U.S. Pat. No. 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in is entirety). For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982), which is incorporated herein by reference in its entirety).

Small Molecules

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A small molecule inhibitor of MIC shedding can be tested for efficacy using an in vitro cell shedding assay as described herein.

Commercially available combinatorial small molecule drug libraries can be screened for such inhibitors using assay methods well known in the art and those described herein. For example, libraries from Vitas-M Lab and Biomol International, Inc. A comprehensive list of compound libraries can be found on the World Wide Web at www.broad.harvard.edu/chembio/platform/screening/compound_libraries/index.htm. Other chemical compound libraries such as those from of 10,000 compounds and 86,000 compounds from NIH Roadmap, Molecular Libraries Screening Centers Network (MLSCN) can be screened in a high throughput assay format. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Using, for example, crystal structures of MIC polypeptides, or crystal structures of MIC polypeptides interacting with ERp5, and aided by computer modeling programs, synthetic organic compounds that mimic the MIC-binding site of ERp5 polypeptide can be designed—such compounds would be expected to bind to the ERp5 binding sequence of MIC and block the functional interaction of that sequence with ERp5 to thereby inhibit MIC shedding. Li et al., 2001, Nature Immunol. 2: 443-451 and Li et al., 1999, Immunity 10: 577-584, incorporated herein by reference, describe the crystal structure of MICA. Holmes et al., 2002, J. Immunol. 169: 1395-1400, incorporated herein by reference, describes the crystal structure of MICB. In one embodiment, the sequence required for interaction of ERp5 with a MIC polypeptide includes or consists essentially of the amino acid sequence NGTYQT (SEQ ID NO: 1), the sequence YQTWVATR (SEQ ID NO: 2), or the sequence NGTYQTWVATR (SEQ ID NO: 112). In another embodiment, the sequence NGTYQT (SEQ ID NO: 1), YQTWVATR (SEQ ID NO: 2), or the sequence NGTYQTWVATR (SEQ ID NO: 112) is in the context of a larger polypeptide, e.g., the MIC domain noted by arrows in FIG. 7b. Software for computer assisted molecular (Drug) design is known in the art and can be found, for example, at www.netsci.org/Resources/Software/Modeling/CADD/, e.g. MOLSCAT, Chem3D, and ADAPT.

In one embodiment, the libraries of compounds, drugs, and/or small molecules used for screening can be obtained from commercial sources such as Biomol Inc., among others. Available compound libraries include, for example: bioactive lipid library, endocannabinoid library, fatty acid library, Harvard Institute of Chemistry and Cell Biology (ICCB) known bioactives library, ion channel ligand library, kinase inhibitor library, kinase/phosphatase inhibitor library neurotransmitter library, LOPAC 1280 compound library, natural products library, nuclear receptor ligand library, orphan ligand library, protease inhibitor library, phosphatase inhibitor library, and rare natural products library; libraries from TimTec, Inc, and many others in the Molecular Libraries Screening Centers Network (MLSCN). Alternately, custom libraries can be made using services of companies such as AsisChem, Inc. Existing libraries are also available among the community of academic researchers at Harvard University, Cambridge, USA and Whitehead Institute for Biomedical Research at MIT, Cambridge, USA.

Aptamers

Aptamers are relatively short RNA or DNA oligonucleotides, which bind ligands and can be isolated, for example, using the selection procedure termed SELEX (systematic evolution of ligands by exponential enrichment) (Tuerk & Gold, 1990; Ellington & Szostak, 1990, which are incorporated herein by reference in their entirety). Because the selection procedure is driven by binding of ligands, aptamers bind their ligands with high affinity and fold into secondary structures which are optimized for ligand binding (Herman & Patel, 2000, incorporated herein by reference in its entirety). In this respect aptamers resemble antibodies by selectively binding corresponding ligand from complex chemical or biological mixtures.

Aptamers are particularly useful in the methods described herein. For example, an aptamer can be used to bind to and inhibit recognition or function of a MIC cleavage site, a site required for a cleavable conformation, or a site that interacts with a regulatory factor or protein such that proteolytic cleavage and thus shedding does not occur.

The aptamer oligonucleotide of such an embodiment can be any useful aptamer now known or later developed. Methods to design and synthesize aptamers and aptamer binding sequences are known to those of skill in the art.

Dosage and Administration

In one aspect, the methods described herein provide a method for treating a MIC-positive tumor in a subject. In one embodiment, the subject can be a mammal. In another embodiment, the mammal can be a human, although the approach is effective with respect to all mammals. The method comprises administering to the subject an effective amount of a pharmaceutical composition comprising an agent that inhibits MIC shedding, in a pharmaceutically acceptable carrier.

The dosage ranges for the agent depends upon the potency, and are amounts large enough to produce the desired effect e.g., a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. Typically, the dosage ranges from 0.001 mg/kg body weight to 0.5 mg/kg body weight. In one embodiment, the dose range is from 5 µg/kg body weight to 30 µg/kg body weight. Alternatively, the dose range will be titrated to maintain serum levels between 5 µg/mL and 30 µg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy.

A therapeutically effective amount is an amount of an agent that is sufficient to produce a statistically significant, measurable change in tumor size, tumor growth etc. (see "Efficacy Measurement" below). Such effective amounts can be gauged in clinical trials as well as animal studies.

An agent can be administered intravenously by injection or by gradual infusion over time. Agents useful in the methods and compositions described herein can be administered intravenously, intranasally, orally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

An agent may be adapted for catheter-based delivery systems including coated balloons, slow-release drug-eluting stents or other drug-eluting formats, microencapsulated PEG liposomes, or nanobeads for delivery using direct mechanical intervention with or without adjunctive techniques such as ultrasound.

In some embodiments, an inhibitor may be combined with a therapeutically effective amount of another chemotherapeutic or anti-angiogenic agent for treatment of cancer (e.g., an epithelial cell tumor or hematopoietic malignancies). The terms "chemotherapeutic agent" or "chemotherapy agent" are used interchangeably herein and refer to an agent that can be used in the treatment of cancers and neoplasms. In some embodiments, a chemotherapeutic agent can be in the form of a prodrug which can be activated to a cytotoxic form. Chemotherapeutic agents are commonly known by persons of ordinary skill in the art and are encompassed for use in the methods described herein. For example, chemotherapeutic drugs for the treatment of e.g., brain tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall). The formulations and compositions as disclosed herein can further comprise administering to a subject a second therapy, wherein the second therapy is therapy for the treatment of abnormal angiogenesis or an anti-cancer therapy, for example an anti-angiogenic therapy or agent, chemotherapy, immunotherapy, surgery, radiotherapy, immunosuppresive agents, or gene therapy with a therapeutic polynucleotide. The second therapy can be administered to the subject before, during, after or a combination thereof relative to the administration of the compositions as disclosed herein. Anti-cancer therapies are well known in the art and are encompassed for use in the methods of the present invention. Chemotherapy includes, but is not limited to an alkylating agent, mitotic inhibitor, antibiotic, or antimetabolite, anti-angiogenic agents etc. The chemotherapy can comprise administration of CPT-11, temozolomide, or a platin compound. Radiotherapy can include, for example, x-ray irradiation, w-irradiation, γ-irradiation, or microwaves.

Other therapeutic approaches that take advantage of the discovery of structures necessary for MIC shedding include, for example, administering a soluble ectodomain of a shedding-resistant MIC mutant, e.g., a mutant described herein in Example 2, or administering a construct expressing such a mutant. This approach would render tumor cells more susceptible to NK cell-mediated killing. In one approach, shedding-resistant soluble MIC mutants can be used to decorate tumor cells using, e.g., polymer or nanoparticle technology, rendering them more susceptible to NK cell-mediated killing. In another approach, an antibody fusion with the shedding-resistant mutant (e.g. fusion protein of antibody (e.g. CD20) with mutant MIC ectodomain) can be used to target the mutant protein to the tumor cell and render the cell susceptible to NK-mediated killing. Methods for delivery of a shedding-resistant mutant to a tumor cell are known in the art, and include, for example, viral or retroviral delivery and nanoparticle approaches.

Pharmaceutical Compositions

The present invention involves therapeutic compositions useful for practicing the therapeutic methods described herein. Therapeutic compositions contain a physiologically tolerable carrier together with an active agent as described herein, dissolved or dispersed therein as an active ingredient.

In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

Efficacy Measurement

The efficacy of a given treatment for cancer can be determined by the skilled clinician. However, a treatment is considered "effective treatment," as the term is used herein, if any one or all of the signs or symptoms of e.g., a MIC-positive tumor are altered in a beneficial manner, other clinically accepted symptoms are improved, or even ameliorated, e.g., by at least 10% following treatment with an agent that inhibits MIC shedding. Efficacy can also be measured by a failure of an individual to worsen as assessed by hospitalization or need for medical interventions (i.e., progression of the disease is halted). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the growth of the tumor; or (2) relieving the disease, e.g., causing regression of symptoms, reducing size of the tumor; (3) preventing the development of a tumor mass from a tumor cell.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, such as e.g., tumor size, tumor mass, tumor density, angiogenesis, tumor growth rate, etc. In addition, efficacy of an agent can be measured by a decrease in circulating MIC peptides or fragments thereof in a subject being treated with an anti-MIC shedding agent.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

Obstructing Shedding of the Immune Stimulatory MIC-B Prevents Tumor Formation

Taking advantage of the fact that human MICB can be recognized by mouse NKG2D (Diefenbach et al., "Ligands for the Murine NKG2D Receptor: Expression by Tumor Cells and Activation of NK Cells and Macrophages," *Nat Immunol* 1: 119-26 (2000); Dunn et al., "Human Cytomegalovirus Glycoprotein UL16 Causes Intracellular Sequestration of NKG2D Ligands, Protecting Against Natural Killer Cell Cytotoxicity," *J Exp Med* 197: 1427-39 (2003), which are hereby incorporated by reference in their entirety) and that only the extracellular α1α2 domain of MIC interacts with NKG2D (Li et al., "Complex Structure of the Activating Immunoreceptor NKG2D and its MHC Class I-like Ligand MICA," *Nat Immunol* 2: 443-51 (2001); Holmes et al., "Structural Studies of Allelic Diversity of the MHC Class I Homolog MIC-B, a Stress-inducible Ligand for the Activating Immunoreceptor NKG2D," *J Immunol* 169: 1395-400 (2002); Strong R K., "Asymmetric Ligand Recognition by the Activating Natural Killer Cell Receptor NKG2D, a Symmetric Homodimer," *Mol Immunol* 38: 1029-37 (2002), which are incorporated herein by reference in their entirety), experiments described below indicate that shedding of MIC permits tumor growth and that sustained interaction between NKG2D and membrane-integrated form of MIC can cause tumor rejection. Using a well-characterized prostate tumor model TRAMP-C2 (Foster et al., "Characterization of Prostatic Epithelial Cell Lines Derived from Transgenic Adenocarcinoma of the Mouse Prostate (TRAMP) Model," *Cancer Res* 57: 3325-30 (1997), herein incorporated by reference in its entirety), it is demonstrated for the first time that expression of the shedding-resistant but not the natural form of MICB prevents tumor formation by transformed cells.

Material and Methods
Cells

TRAMP-C2 (TC2) cell line (gift of Dr. N M. Greenberg, Fred Hutchinson Cancer Research Center, WA) was maintained in DMEM medium as described (Foster et al., "Characterization of Prostatic Epithelial Cell Lines Derived from Transgenic Adenocarcinoma of the Mouse Prostate (TRAMP) Model," *Cancer Res* 57: 3325-30 (1997), herein incorporated by reference in its entirety). RMA-Rae-1β cells (gift of Dr. D. Raulet, Berkeley) was maintained in RPMI1640 supplemented with 10% FCS. Eco-phoenix cells (Orbigen, San Diego, Calif.) were maintained in DMEM supplemented with 10% FBS.

DNA Construction, Transfection, and Transduction.

cDNA encoding full-length of human MICB (allele 0101; Bahram S, et al., *Immunogenetics* 43: 230-3 (1996), herein incorporated by reference in its entirety) was provided by Dr. A. Steinle (University of Tubingen, Tubingen, Germany) and subcloned into the retroviral vector pBMNZ-IRES-GFP (Orbigen, San Diego, Calif.). To generate recombinant soluble MICB (rsMICB), cDNA encoding the extracellular domain of MICB was amplified by PCR. To generate a putative shedding-resistant form of MICB (designated as MICB.A2), aa 215-274 of MICB was replaced with the comparable sequence of the α3 domain of HLA-A2 using recombinant PCR of the cDNA sequences (Horton et al., "Gene Splicing by Overlap Extension: Tailor-made Genes Using the Polymerase Chain Reaction," *Biotechniques* 8: 528-35 (1990), herein incorporated by reference in its entirety). rsMICB-FLAG fusion peptide was generated by tagging the cDNA sequence of FLAG (DKYDDDK; SEQ ID NO: 113) to the S-end of the rsMICB cDNA using PCR. Error-free amplified cDNAs were identified by sequencing and subcloned into the retroviral vector pBMNZ-IRES-GFP (Orbigen). Plasmids were transfected into Eco-pheonix packaging cells to generate retrovirus. TC2 cells were transduced with respective retrovirus. Stable GFP-positive cell population was isolated by drug selection and sorted by flow cytometry.

Affinity Purification of rsMICB and rsMICB-FLAG Peptides

The HiTrip NHS-activated column (GE Healthcare) was conjugated with the mAb 6D4.6 (Santa Cruz Biotechnology, Santa Cruz, Calif.) before being loaded with conditioned media from TC2-rsMICB or TC2-rsMICB.FLAG cells. After washing, rsMICB or rsMICB.FLAG was eluted with 100 mM sodium citrate, pH2.5 and neutralized immediately with 1.5M Tris buffer (pH 8.8).

Immunoprecipitation and Western Blotting

Supernatant was collected from TC2-MICB cell culture and passed through a 0.45 μm filter to remove cell debris. Cells were washed and lyzed with lysis buffer (50 mM HEPES, pH 7.5, 150 mM NaCl, 1.5 mM $MgCl_2$, 1 mM EGTA, 1% Triton X-100). Clear supernatant and lysates were incubated with the mAb 6D4.6. Immunocomplexes were collected using protein A/G-agarose (Pierce, Rockford, Ill.). PNGase F (New England Biolabs, Beverly, Mass.) treatment was carried overnight at 37° C. Immunocomplexes were separated on a 4-15% SDS-PAGE, blotted onto a nitrocellulose membrane, and probed with a goat anti-MICB antibody AF1599 (R&D systems, Minneapolis, Minn.). Immunoreactive proteins were detected by incubating the blot with a horseradish peroxidase-conjugated secondary antibody (Pharmacia, Piscataway, N.J.) and ECL reagents (Pharmacia).

MICB Shedding Assay and (s)MICB ELISA

Cells were seeded at a density of $4 \times 10^5$ cells/well in a 6-well plate in complete media overnight, which was replaced with 1 ml/well serum-free media for 6 hrs. The supernatant was collected and filtered through a 0.45 μm filter. Cells were lyzed with 1 ml lysis buffer. The amount of soluble MICB in the supernatant and MICB in the cell lysates was measured using human MICB DuoSet sandwich ELISA kit (R&D Systems). For measuring mouse serum levels of soluble MICB, serum was diluted 1:2 with PBS for ELISA assay.

In Vivo Study

Animal studies were approved by Institutional Animal Care and Use Committee. Six to ten 6-week-old SCID male mice (Harlan Sprague Dawley, Ind.) were used in each group. $1 \times 10^6$/mouse of the following cells were subcutaneously injected into respective group of animals: TC2, TC2-MICB, TC2-MICB.A2, and TC2-rsMICB. All animals were monitored for tumor growth for up to 12 weeks. Tumor volume was estimated using the formula: volume=$L \times W^2/2$. Animals were euthanized when tumor volumes reached 1000 $mm^3$. Tumors, spleens, and peripheral blood were terminally collected. Serum was separated by centrifugation and used for rsMICB ELISA.

In Vivo NKG2D Blocking or Neutralization

To block the NKG2D receptor, 100 μg of the functional grade of anti-NKG2D blocking antibody CX5 (ebiosciences) was injected intraperitoneally (i.p.) on the day before and the day after tumor implantation and thereafter every three days. Blocking was confirmed by flow cytometry of peripheral lymphocytes collected from orbital sinus bleeding with PE-conjugated CX5 (ebiosciences). To modify NKG2D function, animals were injected i.p. with 50 ng of purified rsMICB prior to implantation of TC2-MICB.A2 cells and thereafter twice per week for four weeks. Blood was collected once a week from sinus orbital bleeding and serum levels of rsMICB was measured by ELISA.

Flow Cytometry

For detection of cell surface expression of NKG2D ligands, TC2 and its derivative cells were trypsinized, blocked with anti-mouse CD16/32 (eBiosciences, San Diego, Calif.), and incubated with anti-MICA/B mAb 6D4.6 or anti-MICB MAB1599 (R&D systems) or anti-pan-RAE-1 mAb17582 (R&D systems) followed by a PE-conjugated secondary reagent. For detection of rsMICB expression, the BD Cytofix/Cytoperm kit (BD Sciences) was used. Briefly, TC2-rsMICB cells were cultured in the presence of BD GolgiPlug for 3 hr to prevent the secretion of rsMICB before harvesting. Cells were resuspended in BD Fixation/permeabilization solution for 20 min at 4° C. and incubated with 6D4.6 followed with PE-conjugated secondary reagents. For a mouse NKG2D binding assay, cells were incubated with 10 μg/ml of the fusion protein of recombinant soluble mouse NKG2D and human Fc (smNKG2D-Fc, R&D Systems) followed by PE-conjugated F(ab)2 goat-anti-human IgG. For H-2Kb expression, cells were incubated with Alex647-conjugated anti-H-2Kb/Db mAb (Biolegend, San Diego, Calif.).

Single cell suspensions of splenocytes were prepared as described (Ho E L, et al., *J Immunol* 169: 3667-75 (2002)). Cells were stained with FITC-conjugated mAb DX5 (ebiosciences) and PE-conjugated anti-mouse NKG2D mAb CX5 (ebioscience) or A10 (ebiosciences) and analyzed using a BD FACscan or LSRII. For an ex vivo rsMICB competitive binding assay, freshly isolated splenocytes were incubated with 10 ng/µl of rsMICB-FLAG followed with FITC-conjugated mAb M2 (Sigma-Aldrich) and PE-conjugated mAb DX5 (ebioscience). Data were analyzed using the BD CellQuest-Pro (BD Biosciences) or FlowJo software (Tree Star Inc, Asland, Oreg.).

Cytotoxicity Assay

Fresh NK cells were prepared using Spinsep murine NK enrichment cocktail (Stem Cell Technology, Vancouver, BC) and were >90% DX5+. LAK cells were prepared by culturing NK cells for 4-7 days in 1000 U/ml of rhIL-2. Cytotoxicity was performed in triplicate using the standard 4 h $^{51}$Cr release assay (Wu et al., "Prevalent Expression of the Immunostimulatory MHC Class I Chain-related Molecule is Counteracted by Shedding in Prostate Cancer," *J Clin Invest* 114: 560-8 (2004), herein incorporated by reference in its entirety). Antibody blocking was performed by pre-incubating effector cells with 30 µg/ml NKG2D blocking mAb CX5 (ebiosciences) or pre-incubating target cells with 100 µg/ml of anti-pan RAE-1 pAb at 37° C. for 1 hr (Masuda H, et al., *Biochem Biophys Res Commun* 290: 140-5 (2002), herein incorporated by reference in its entirety).

Statistical Analysis

Data were analyzed using JMP software. Significance between two animal groups was determined by a student's t-test. $P<0.05$ was considered significant.

Results

Cleavage Region of MIC(B) in TRAMP-C2 Tumor Cells

TC2 is a mouse prostate tumor cell line generated from the TRAMP (TRansgenic Adenocarcinoma Mouse Prostate) mouse (Foster et al., "Characterization of Prostatic Epithelial Cell Lines Derived from Transgenic Adenocarcinoma of the Mouse Prostate (TRAMP) Model," *Cancer Res* 57: 3325-30 (1997), herein incorporated by reference in its entirety), which does not express any homologous molecules to human MIC (Bahram et al., "Nucleotide Sequence of a Human MHC Class I MICB cDNA," *Immunogenetics* 43: 230-3 (1996), herein incorporated by reference in its entirety). TC2 cells were transduced with retroviruses that carry cDNAs of human MICB and GFP. Transduced cells stably expressing high levels of MICB (designated as TC2-MICB cells) were generated by puromycin selection and multiple-rounds of flow cytometry cell sorting for GFP-positive cells.

Figure 1B:
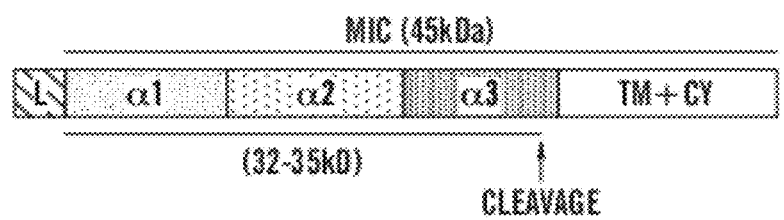
FIG. 1b shows a diagram depicting the MICB cleavage site(s).

In order to generate a shedding-resistant form of MICB, experiments were first performed to predict a putative cleavage region of MICB by tumor cells. Soluble MICB resulting from TC2 shedding (designated as ssMICB) was immunoprecipitated from the supernatant of TC2-MICB cells with a mouse monoclonal antibody (mAb) 6D4.6 specific to the $\alpha 1\alpha 2$ ectodomain of MICA/B (Groh et al., "Broad Tumor-associated Expression and Recognition By Tumor-derived Gamma Delta T Cells of MICA and MICB," *Proc Natl Acad Sci USA* 96:6879-84 (1999), herein incorporated by reference in its entirety). The full length MICB was immunoprecipitated from cell lysates with the same antibody. Immune complexes were separated and immunoblotted with a goat polyclonal antibody AF1599 specific to the ectodomain of MICB. After N-glycosidase (PNGaseF) treatment, ssMICB yield two bands of molecular mass approximately 31-33 kDa (FIG. 1a). The molecular mass is consistent with other studies showing soluble MICB and soluble MICA released by human tumor cells (Salih et al., "Release of MICB Molecules by Tumor Cells: Mechanism and Soluble MICB in Sera of Cancer Patients," *Hum Immunol* 67: 188-95 (2006); Kaiser et al., "Disulphide-isomerase-enabled Shedding of Tumour-associated NKG2D Ligands," *Nature* 447: 482-6 (2007), which are incorporated herein by reference in their entirety). When samples were treated with dinitrothiocyanobenzene (DNTB), a disulfide isomerase inhibitor, only a single band of soluble MICB was revealed (data not shown), suggesting that the two bands of soluble MICB released by TC2 cells are the reduced and non-reduced forms of ssMICB. Similar observation of soluble MICA shed by human tumor cell lines was shown by Kaiser et al. (Kaiser et al., "Disulphide-isomerase-enabled Shedding of Tumour-associated NKG2D Ligands," *Nature* 447: 482-6 (2007), herein incorporated by reference in its entirety). The deglycosylated full-length MICB is shown to be approximately 41 kDa in the cell lysates (FIG. 1a), consistent with other studies (Wu et al., "Intracellular Retention of the MHC Class I-related Chain B Ligand of NKG2D by the Human Cytomegalovirus UL16 Glycoprotein," *J Immunol* 170: 4196-200 (2003), herein incorporated by reference in its entirety). These data suggest that MICB was cleaved at the alpha-3 domain proximal to the transmembrane region to generate ssMICB (FIG. 1b). Similar cleavage region is also predicted for human tumor cell lines to generate soluble MICA (Kaiser et al., "Disulphide-isomerase-enabled Shedding of Tumour-associated NKG2D Ligands," *Nature* 447: 482-6 (2007), herein incorporated by reference in its entirety).

Generation of Tumor Cell Lines Expressing the Putative Shedding-Resistant MICB

Figure 2A:
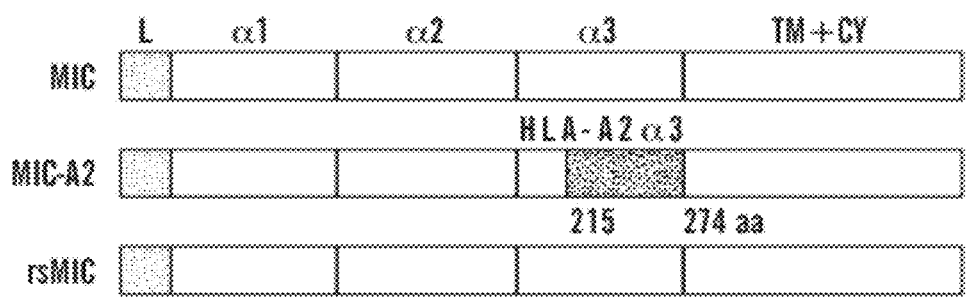
FIG. 2a depicts a diagram showing generation of the non-cleavable form MICB.A2 by replacing aa 215-274 of the MICB α3 domain with the corresponding sequence of HLA-A2. rsMICB was generated by deletion of the entire transmembrane and cytoplasmic region of MICB.
Figure 2B:
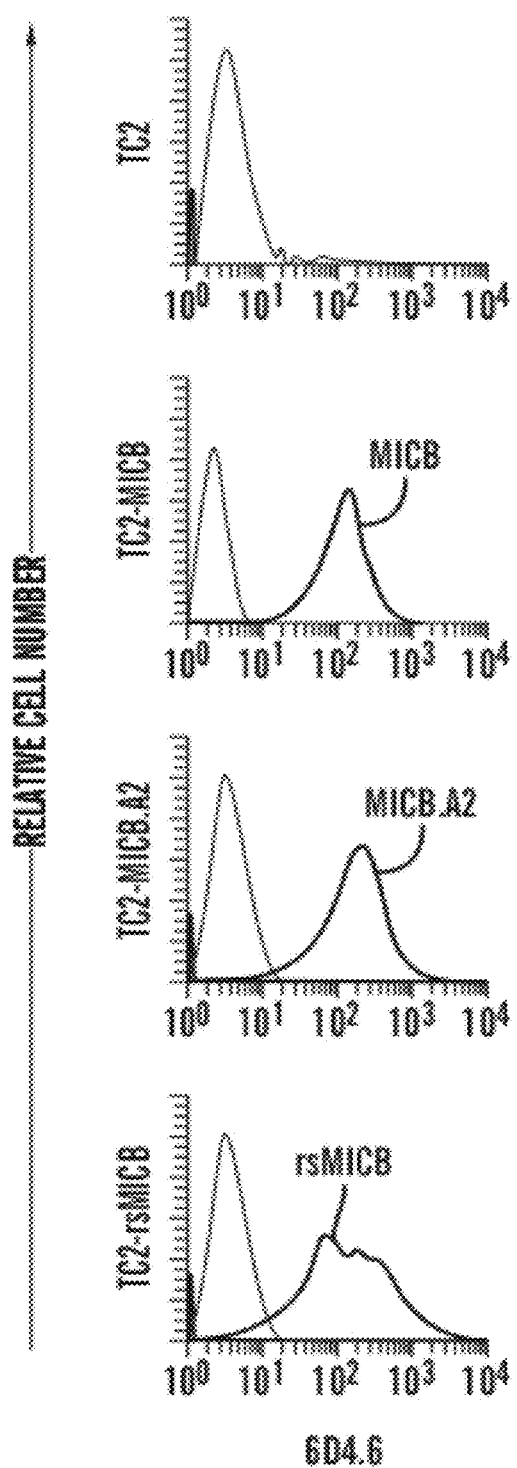
FIG. 2b depicts flow cytometry showing expression levels of MICB, MICB.A2, and rsMICB in TC2 cell lines. cDNAs of MICB, MICB.A2, or rsMICB were inserted into a IRES-GFP retroviral vector pBMNZ. TC2 cells were transduced with respective retrovirus. GFP-positive cells were sorted by flow cytometry. For detection of MICB and MICB.A2 expression, cells were directly incubated with anti-MIC 6D4.6 antibody followed with a PE-conjugated secondary reagent. For detection of the secretable rsMICB expression, TC2-rsMICB cells were cultured in the presence of BD GolgiPlug for 3 hr to prevent the secretion of rsMICB before harvesting. Cells were resuspended in BD Fixation/permeabilization solution for 20 min at 4° C. and incubated with 6D4.6 followed with a PE-conjugated secondary reagent.

To study the impact of MIC shedding on tumor formation and growth in vivo, two forms of MICB were generated, the recombinant secretable form of MICB (rsMICB) and a putative shedding-resistant form of MICB (MICB.A2). rsMICB was generated by deletion of the transmembrane and cytoplasmic domain. MICB.A2 was generated by replacing part of the $\alpha 3$ domain of MICB (aa 215-274) with the corresponding residues from HLA-A2 (FIG. 2a). Since NKG2D only interacts with the $\alpha 1\alpha 2$ domain of MIC (Li et al., "Complex Structure of the Activating Immunoreceptor NKG2D and its MHC Class I-like Ligand MICA," *Nat Immunol* 2: 443-51 (2001), herein incorporated by reference in its entirety), MICB.A2 would presumably continue to recognize NKG2D. rsMICB and MICB.A2 were overexpressed in TC2 cells using the GFP retroviral system described above. Positive-expressing clones were selected by puromycin and repeated sorting by flow cytometry for GFP-positive cells. The expression level of cellular rsMICB and surface MICB.A2 in TC2 cells were confirmed by flow cytometry with the anti-MIC mAb 6D4.6 (FIG. 2b).

Partial Replacement of the $\alpha 3$ Domain of MICB Protects from Tumor Cell Shedding An ELISA assay was used to assess the degree of shedding of MICB and MICB.A2 in TC2 cell lines. Both the capture and the detection antibodies are specific to the extracellular domain of MICB and can also detect MICB.A2 by western blotting (data not shown). With a given number of cells, the amount of cleaved soluble MIC in the culture supernatant and the amount of MIC in the lysates were measured by a sandwich ELISA assay (FIG. 2c). The degree of MIC shedding was estimated by the molar percentage of soluble MICB released into the supernatant. Approximately 30% of MICB was cleaved into the media in TC2 cells, whereas no cleaved form of MICB.A2 was detectable in the culture supernatant (FIG. 2c). This indicates that MICB.A2 cannot be cleaved into soluble forms by tumor cells and is shedding-resistant.

Expression of MICB.A2 in TC2 Cells Stimulates Mouse NK Cell Cytolytic Activity

Figure 3A:
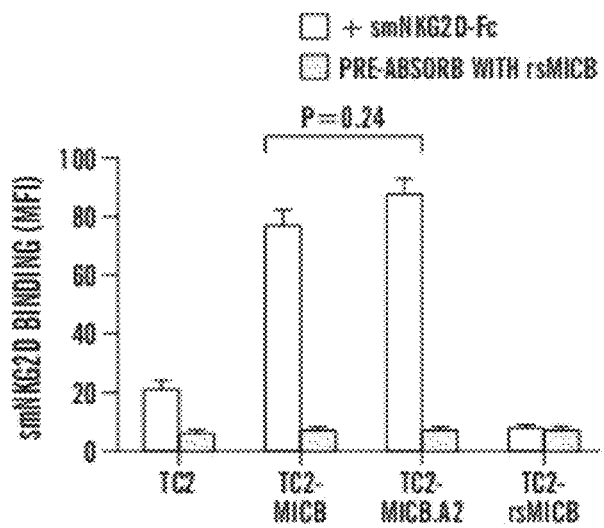
FIG. 3a shows binding of MICB and MICB.A2 by mouse NKG2D. Cells were incubated with the chimeric soluble mouse NKG2D-humanFc (smNKG2D-Fc) followed by PE-conjugated anti-human IgG. Cells were analyzed by flow cytometry. Data shown are mean fluorescence intensity (MFI). When smNKG2D-Fc was pre-absorbed with rsMICB, no binding was seen in any of the cell lines. No significant difference was shown in the binding ability between MICB and MICB.A2 (p=0.24).
Figure 3B:
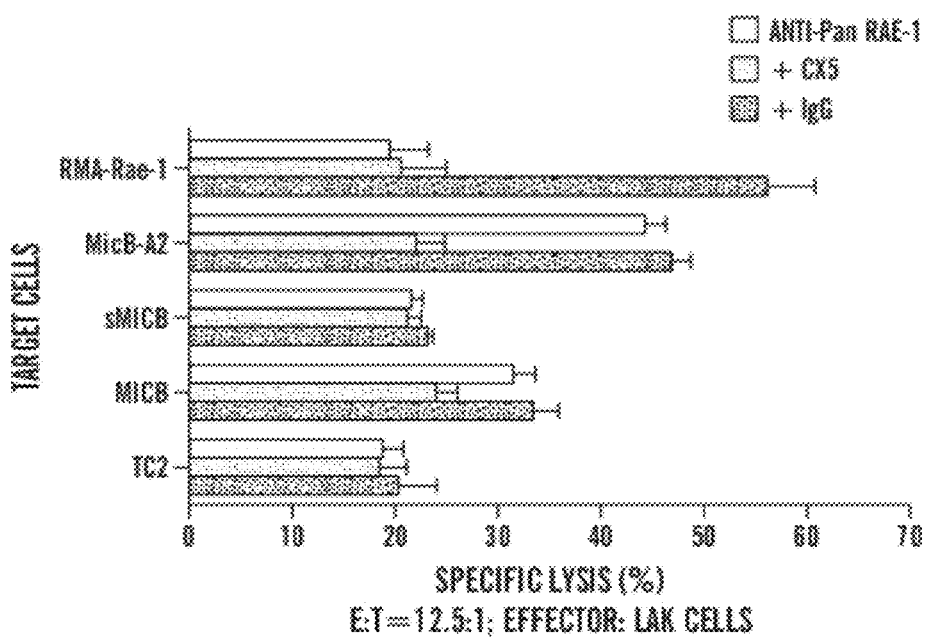
FIG. 3b shows sensitivity of various MICB-expressing TC2 cells to mouse NK cells. NK cells were isolated from SCID mice and cultured in complete media with 1000 U/ml of IL-2 for 4 days before used as effectors in standard 4-h 51Cr release assay. For blocking NKG2D receptor, effector cells were pre-incubated with 30 µg/ml of CX5 antibody. For blocking RAE-1, target cells were pre-incubated with 100 ug/ml of anti-pan RAE-1 pAb for 1 hr prior to the assay. RMA-Rae-1 cells were used positive controls for blocking antibodies. E:T, effector:target ratio. Bar, SE. *, P<0.01 compared to TC2 cells as targets.

Human MICB can be recognized by mouse NKG2D and activate mouse NK cells. To test whether overexpressing MICB.A2 can also activate mouse NK cells, the physical interaction of MICB.A2 with soluble mouse NKG2D-Fc (smNKG2D-Fc) fusion protein was addressed by flow cytometry analyses. As measured by mean fluorescence intensity (FIG. 3a), smNKG2D-Fc was more prominently bound by TC2-MICB and TC2-MICB.A2 cells and only weakly bound by TC2 and TC2-rsMICB cells. Accordingly, an in vitro cytotoxicity assay revealed a marked increase in sensitivity of TC2 cells to IL-2 activated mouse NK (LAK) cells when MICB or MICB.A2 was overexpressed (FIG. 3b, p<0.01). The increased susceptibility of TC2-MICB and TC2-MICB.A2 cells to LAK cells can be inhibited by pre-incubation of LAK cells with the NKG2D-specific blocking antibody CX5 (FIG. 3b), indicating a NKG2D-dependent LAK cell killing effect. Thus, the shedding-resistant MICB.A2 maintained the functional property of MICB to be recognized by mouse NKG2D.

Figure 3C:
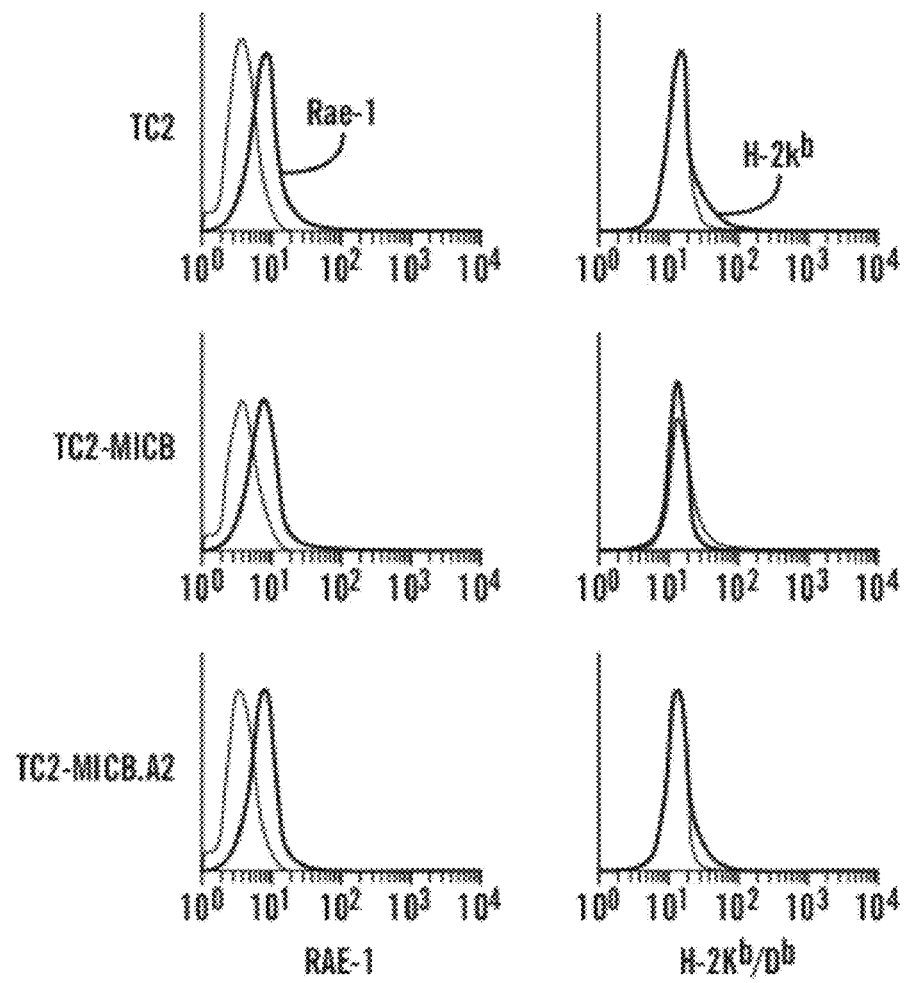
FIG. 3c depicts flow cytometry histograms showing surface expression of RAE-1 (left panel) and H-2Kb/Db (right panel) in TC2, TC2-MICB, and TC2-MICB.A2 cells. Filled histograms, cells were stained with control isotype antibodies. Open histograms, cells were stained with specific antibodies. Results represent three independent experiments.

Although not expressing any MIC homolog, TC2 cells express some endogenous NKG2D ligand RAE-1 variants, but not H60 (Diefenbach et al., "Ligands for the Murine NKG2D Receptor: Expression by Tumor Cells and Activation of NK Cells and Macrophages," *Nat Immunol* 1: 119-26. (2000); Diefenbach et al., "The Innate Immune Response to Tumors and Its Role in the Induction of T-cell Immunity," *Immunol Rev* 188: 9-21 (2002), which are herein incorporated by reference in its entirety). However, the level of endogenous NKG2D ligands is not sufficient to stimulate LAK cell in vitro cytotoxicity (FIG. 3b). To address whether the increased sensitivity of TC2-MICB and TC2-MICB.A2 cells to LAK cell killing is possibly due to increased expression of RAE-1, endogenous RAE-1 expression was analyzed on these cell lines by flow cytometry with a rat anti-pan RAE-1 monoclonal antibody. A consistency of RAE-1 expression among TC2, TC2-MICB, and TC2-MICB.A2 cell lines is shown in FIG. 3c. Furthermore, pre-incubation of target cells with an anti-pan RAE-1 blocking antibody (Ho E L, et al., *J Immunol* 169: 3667-75 (2002), herein incorporated by reference in its entirety) did not significantly reduce the susceptibility of TC2-MICB or TC2-MICB.A2 cells to LAK cells, whereas the sensitivity of the control RMA-Rae-1β cells to LAK cells was significantly reduced (FIG. 3b). These data indicate that the increased killing of TC2-MICB or TC2-MICB.A2 cells by LAK cells is not due to increased RAE-1 expression.

TC2 cells express a very low level of H-2Kb/Db (Grossmann M E, et al., *World J Urol* 19: 365-70 (2001), herein incorporated by reference in its entirety), which is a potential ligand for inhibitory Ly49 receptor families. H-2Kb/Db expression was analyzed on these cell lines by flow cytometry. Consistent levels of H-2Kb/Db expression were found in TC2 and cell lines expressing MICB or MICB.A2 (FIG. 3c), indicating that the increased sensitivity of TC2-MICB and TC2-MICB.A2 cells to LAK cells was not attributed to a reduced level of H-2Kb/Db expression.

Figure 4A:
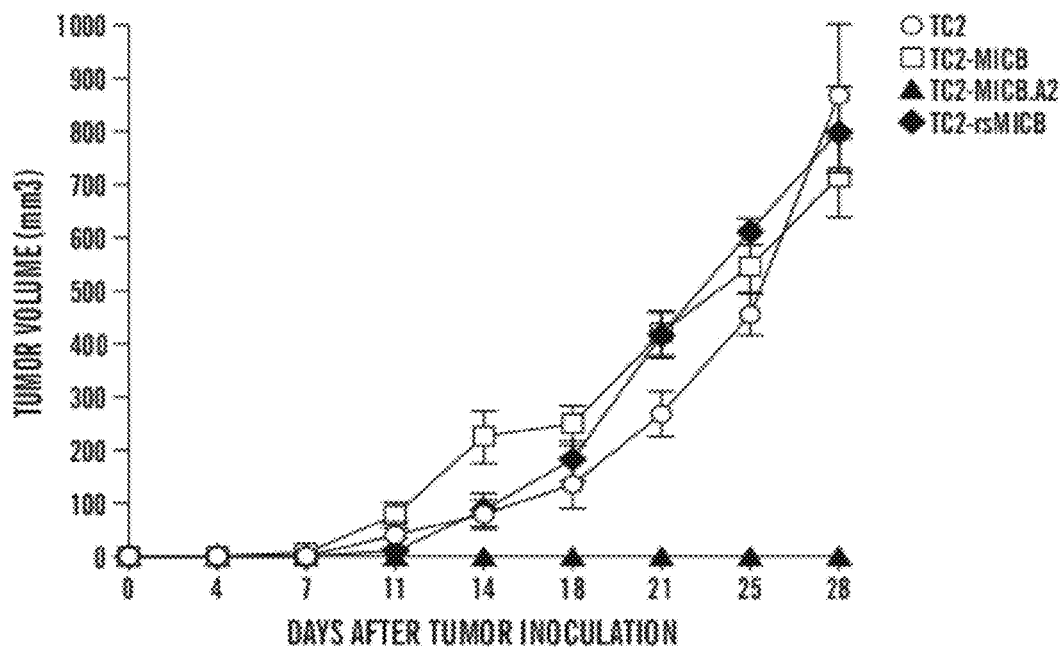
FIG. 4a shows tumor growth of various MICB expressing TC2 cells in SCID mice.
Figure 4B:
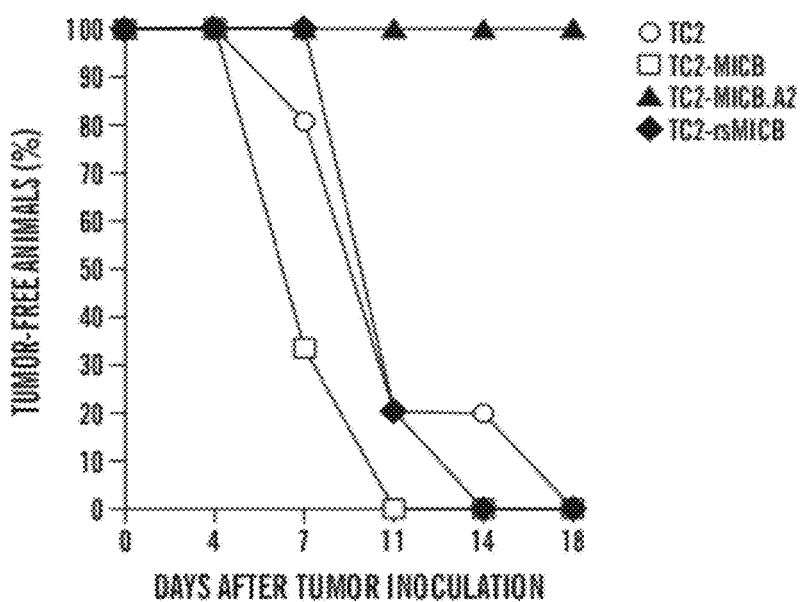
FIG. 4b shows the rate of tumor formation of various MICB expressing TC2 cells in SCID mice. $1\times10^6$ cells were injected subcutaneously (s.c.) into each animal in (a) and (b).
Figure 4C:
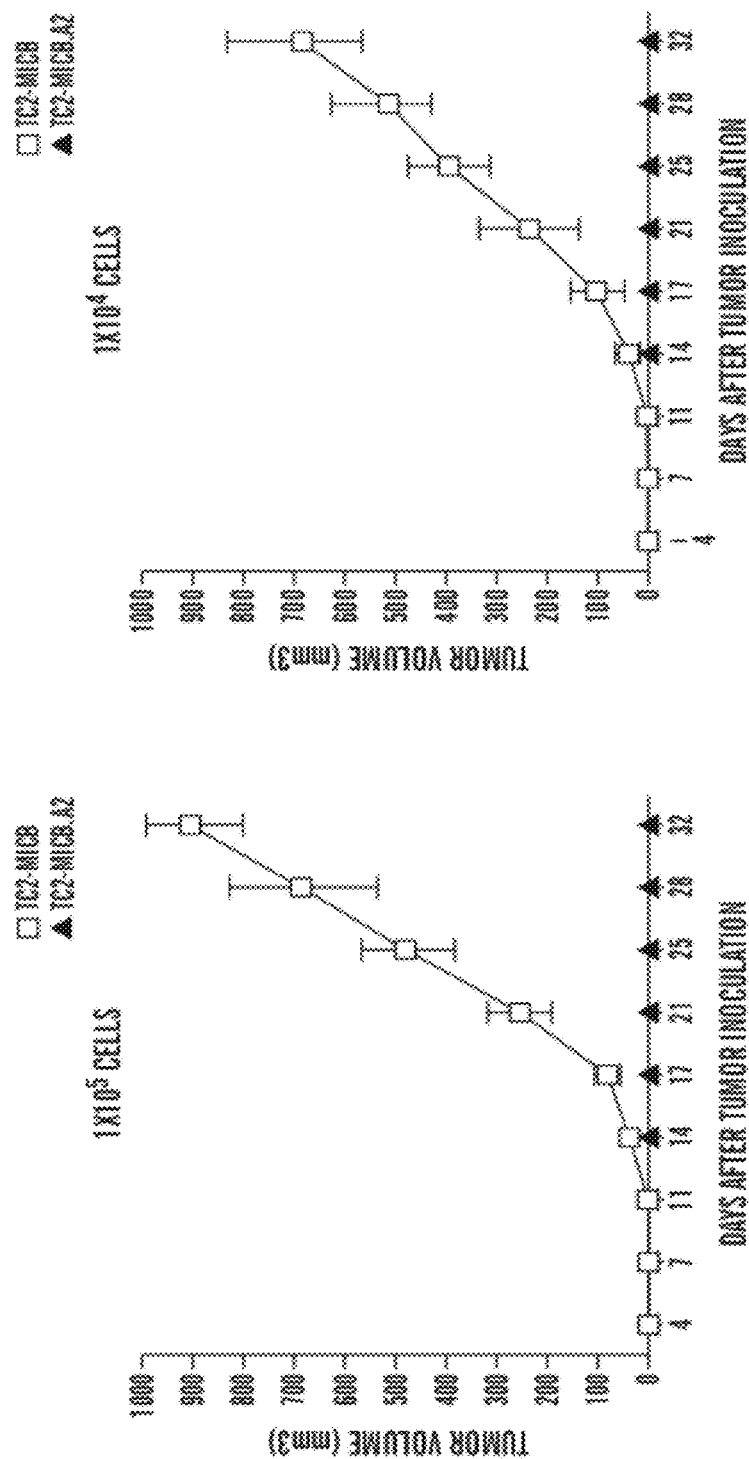
FIG. 4c shows tumor growth of TC2-MICB cells when injected at lower doses ($1\times10^5$ and $1\times10^4$ cells/animal).
Figure 4D:
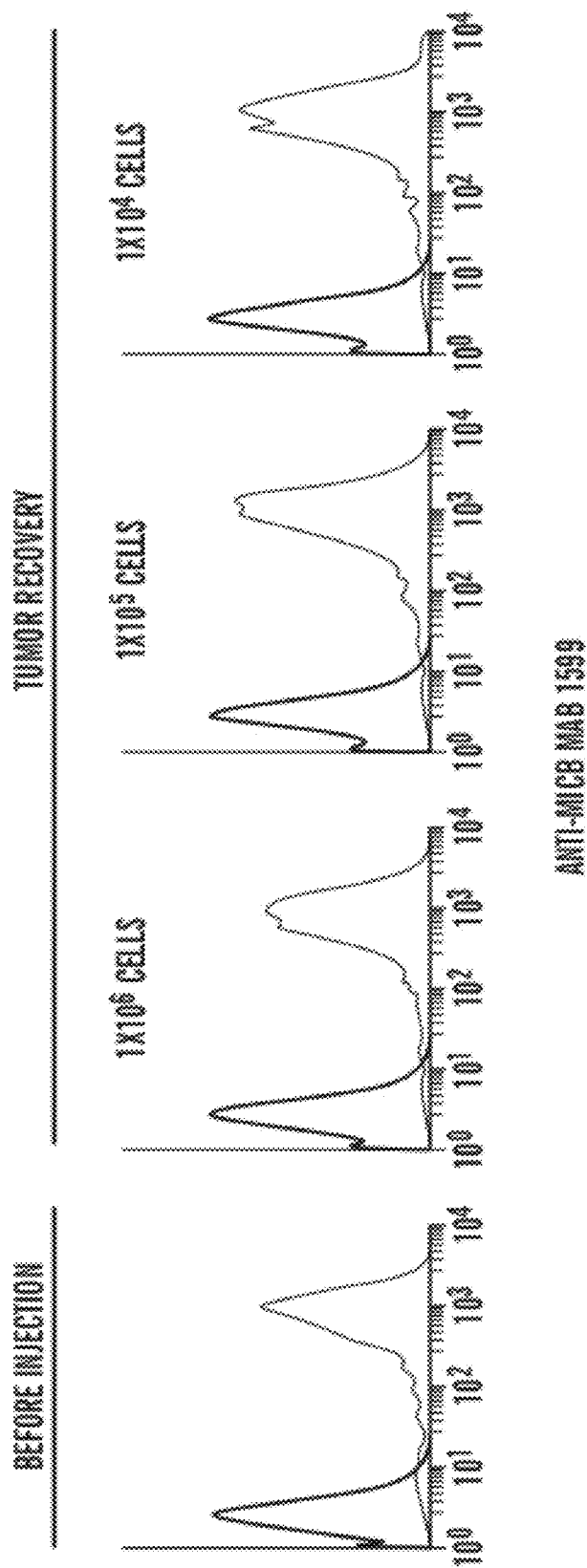
FIG. 4d depicts representative flow cytometry histoplots showing MICB expression in tumor cells extracted from animals inoculated with TC2-MICB cells compared to prior inoculation. The MICB-specific antibody MAB1599 (R & D systems) was used as a primary antibody. The filled histogram represents MICB expression in TC2 cells. The open histogram represents MICB expression in TC2-MICB cells or tumor cells. Results represent three independent experiments.

The Shedding-Resistant MICB.A2 but not the Natural MICB Prevents TC2 Tumor Formation in Vivo In three independent experiments, when SCID animals were implanted with TC2-rsMICB, TC2-MICB, or TC2-MICB.A2 cells, none of the animals that were implanted with the TC2-MICB.A2 cells developed tumors with a 12-week follow-up observation period, whereas all of the animals that were implanted with TC2-rsMICB or TC2-MICB cells developed tumors within three weeks (FIGS. 4a and 4b). In addition, no significant difference in tumor growth was observed among TC2, TC2-rsMICB, and TC2-MICB-originated tumors (FIG. 4a). To address whether the failure to reject TC2-MICB tumors is due to the large dose ($1\times10^6$) of tumor cells injected, we repeated the experiment with TC2-MICB and TC2-MICB.A2 cells using smaller numbers of inoculated cells. A tenfold ($1\times10^5$) and a 100-fold ($1\times10^4$) decrease in the number of inoculated tumor cells did not change the outcome (FIG. 4c). MICB expression was also examined in the TC2-MICB-originated tumor cells extracted from SCID animals by flow cytometry. All the extracted tumor cells expressed the similar levels of MICB as prior to implantation (FIG. 4d). This indicates that tumor growth in animals that were implanted with TC2-MICB cells is not due to NK cells selectively eliminating MICB-positive cells.

Shedding of MICB by TC2 Cells Allows TC2-MICB Tumor Growth in Mice

Figure 5A:
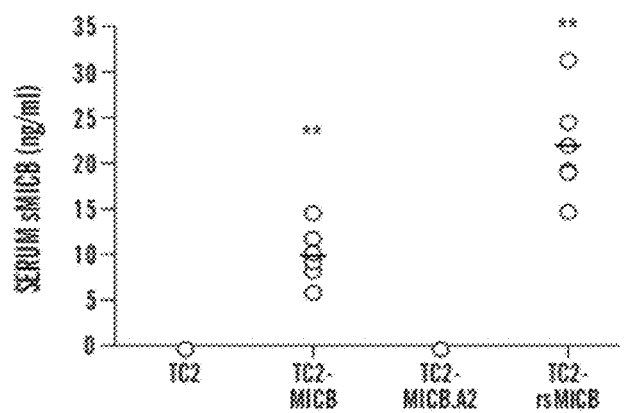
FIG. 5a shows serum levels of sMICB in all the tumor-bearing animals.
Figure 5B:
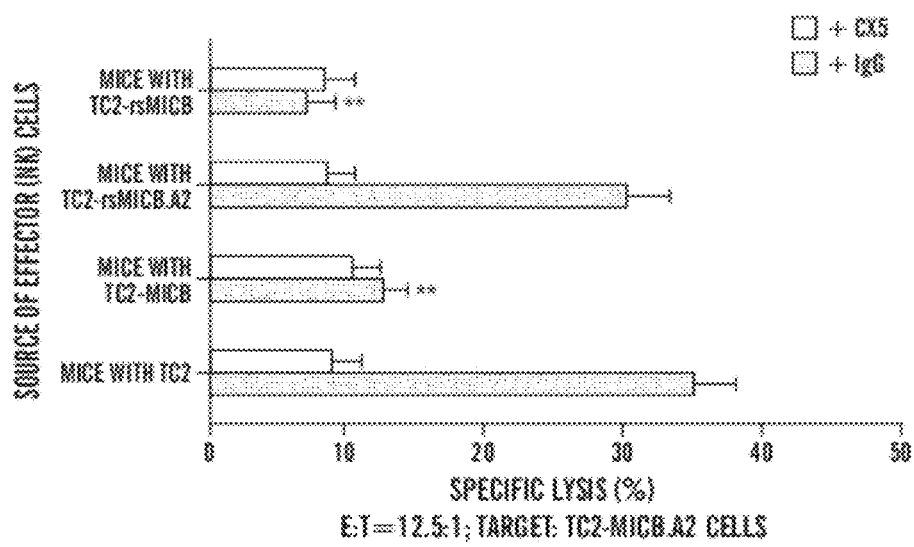
FIG. 5b shows reduced NKG2D-dependent NK cell cytotoxicity of splenic NK cells from animals bearing TC2-sMICB and TC2-MICB tumors. Freshly isolated NK cells were used as effectors; TC2-MICB.A2 cells were used as target cells. **, P<0.01 compared to which of TC2 or TC2-MICB.A2. Results represent three independent experiments.

In 4-h in vitro cytotoxicity assays, both TC2-MICB and TC2-MICB.A2 cells were sensitive to LAK cells (FIG. 3b). However, NK tumor immunity was effective only in animals when the non-cleavable MICB.A2 was expressed on tumor cells. Without wishing to be bound by theory, it is postulated that this discrepancy of in vivo and in vitro observation is attributed to tumor cell shedding of MICB in vivo which cumulatively compromises NK cell function in animals implanted with MICB-expressing tumor cells. To test this hypothesis, serum levels of soluble MICB were measured in all of the animals four weeks after tumor implantation using a sandwich ELISA assay. A significant level of soluble MICB was detected in the sera of animals that were implanted with tumor cells expressing rsMICB and MICB; whereas no soluble MICB was detectable in animals implanted with tumor cells expressing MICB.A2 (FIG. 5a). To address why TC2-MICB cells were sensitive to LAK cell in vitro, LAK cells were incubated with the supernatant of TC2-MICB cells for various time periods and used as effector cells to kill target TC2-MICB.A2 cells. Only after 8-h incubation, LAK cell killing ability was significantly affected. Therefore, in the 4-h in vitro cytotoxicity assay, the killing ability of LAK cells was not significantly affected by soluble MICB resulting from target TC2-MICB cells (data not shown). NK cell tumor killing ability from these animals was further examined. For this purpose, freshly isolated splenic NK cells were used as effector cells for an in vitro cytotoxicity assay. NK cells from mice bearing MICB and rsMICB-expressing tumors had a significant reduction in cytotoxicity against TC2-MICB.A2 target cells in comparison to those from TC2 tumor-bearing or tumor-free animals (P<0.01, FIG. 5b). The cytotoxicity of these NK cells was inhibited by pre-incubating with a NKG2D-specific inhibitory mAb CX5 (FIG. 5b), suggesting a NKG2D-dependent effect. Together, these results suggest that persistent presence of soluble MICB in vivo due to tumor cell shedding of MICB compromised NKG2D-mediated NK cell lytic activity and thus permitted the growth of MICB-expressing tumor cells.

Figure 6A:
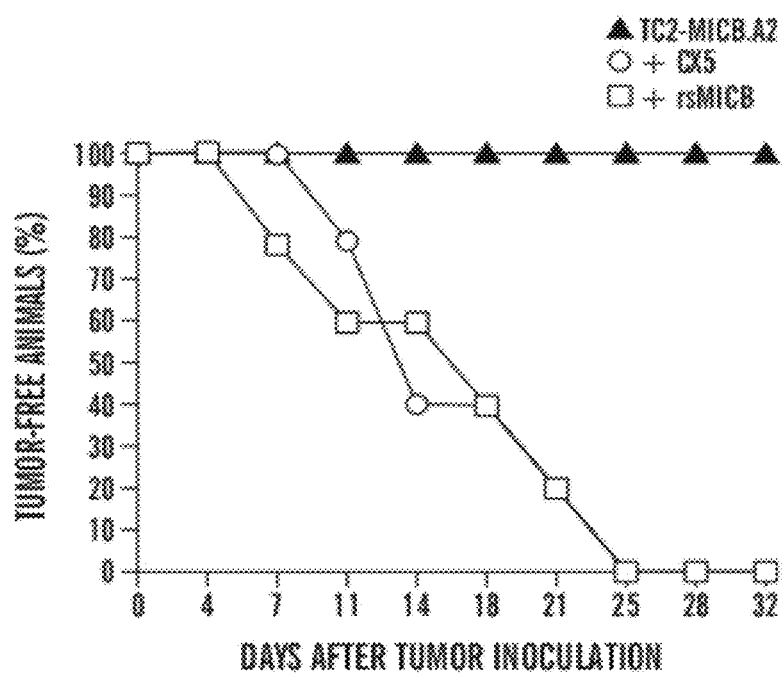
FIG. 6a shows that in vivo blocking NKG2D with CX5 antibody or neutralization of the function of NKG2D with rsMICB enables TC2-MICB.A2 cells to form tumors. To block NKG2D receptor in vivo, 100 µg of NKG2D-specific antibody CX5 was injected intraperitoneally (i.p.) on the day before and the day after tumor implantation and thereafter every three days. To modify NKG2D function, animals were i.p. injected with 50 ng of purified rsMICB prior to implantation of TC2-MICB.A2 cells and thereafter twice a week for four weeks.

Persistent Presence of Soluble MICB Blocks the NKG2D-Mediated NK Cell Recognition of Target Cells When animals were treated with the CX5 antibody to block NKG2D receptor, injection of TC2-MICB.A2 cells gave rise to tumor formation in all of the SCID animals (FIG. 6a). This indicates that the inhibition of TC2-MICB.A2 tumor formation in SCID animals is NKG2D-dependent. To test the effect of presence of soluble MICB on tumor formation of MICB.A2-expressing cells, animals were injected with purified rsMICB (50 ng) before and after implanting TC2-MICB.A2 cells. Under this experimental condition, implantation of TC2-MICB.A2 cells gave 100% tumor formation (FIG. 6a). Tumor cells extracted from these animals were shown to be GFP-positive and express MICB.A2 by flow cytometry analyses (data not shown). NK cells isolated from these animals showed very little cytolytic activity against TC2-MICB.A2 target cells (data not shown). These data indicate that persistent presence of soluble MICB compromises the cytotoxicity of NK cells against TC2-MICB.A2 cells.

Figure 6B:
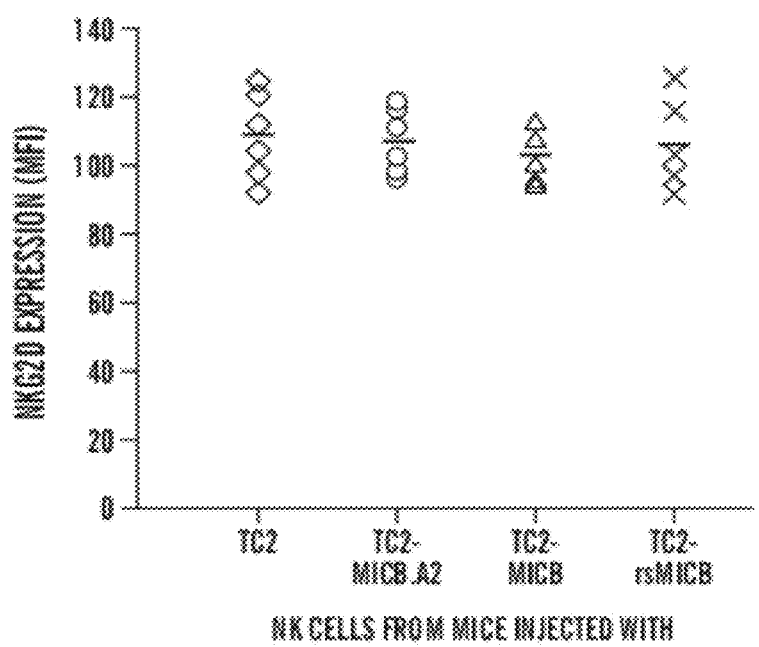
In FIG. 6b, measurements of NKG2D expression are shown as mean fluorescence intensity (MFI) on splenic NK cells freshly isolated from SCID animals (n=6) injected with various tumor cells. bar, mean value of MFI.
Figure 6C:
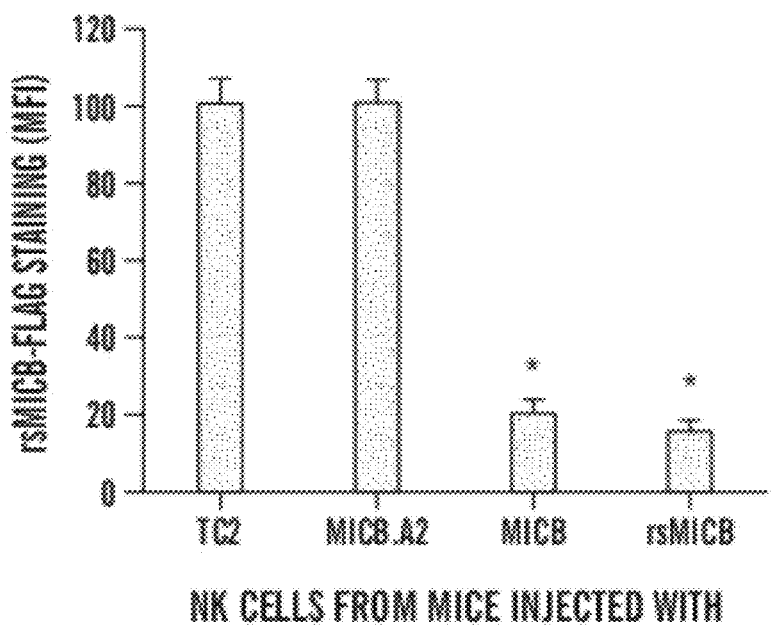
FIG. 6c shows a competitive binding assay indicating saturation of NKG2D receptor by sMICB in animals bearing TC2-MICB and TC2-rsMICB tumors. Freshly isolated splenocytes were incubated with 10 ng/µl of rsMICB-FLAG followed by FITC-conjugated anti-FLAG mAb M2 and PE-conjugated mAb DX5. Data shown are measurements of mean fluorescence intensity (MFI) of M2 staining from six animals of each experimental group. Bar, standard error.*, p<0.01 when compared to animals injected with TC2 or TC2-MICB.A2 tumor cells.

It was sought to determine the mechanisms by which tumor shedding-derived soluble MICB would diminish NK cell activity. Without wishing to be bound by theory, soluble MICB may down-modulate surface NKG2D expression on NK cells (Groh et al., "Tumour-derived Soluble MIC Ligands Impair Expression of NKG2D and T-cell Activation," *Nature* 419: 734-8 (2002), which is hereby incorporated by reference in its entirety) or block the recognition of NK cells to target cells by physical occupancy of the NKG2D receptor. To distinguish these two mechanisms, NKG2D expression was first analyzed on splenic NK cells freshly isolated from animals injected with various TC2 tumor cells using flow cytometry analyses with a non-blocking NKG2D antibody A10 (Horton et al., "Gene Splicing by Overlap Extension: Tailor-made Genes Using the Polymerase Chain Reaction," *Biotechniques* 8: 528-35 (1990), herein incorporated by reference in its entirety). There was no significant difference in surface NKG2D expression on NK cells from mice bearing TC2-MICB and TC2-sMICB tumors compared to those from animals bearing TC2 tumors or tumor-free animals (FIG. 6$b$), indicating that the suppressive effect of soluble MICB on NK cell activity was not through down-modulation of surface NKG2D receptor. The occupancy of NKG2D receptor on NK cells by tumor-derived sMICB was further examined using a competitive binding assay. Freshly isolated splenocytes were incubated with purified rsMICB-Flag and NK cell binding ability to rsMICB-Flag was measured by flow cytometry using the anti-Flag mAb M2. NK cells from animals inoculated with TC2-MICB or TC2-rsMICB cells had significantly reduced binding to rsMICB-Flag compared to those from animals inoculated with TC2 or TC2-MICB.A2 cells ($p<0.01$, FIG. 6$c$). Together, these data show that soluble MICB dampens NKG2D-dependent NK cell activity mainly by masking the NKG2D receptor and thus blocking the interaction of NKG2D with target molecules.

This study has provided conclusive evidence supporting the hypothesis that shedding of MIC by transformed cells can promote tumor growth. In this study, a shedding-resistant NKG2D ligand MICB.A2 was generated by partially modifying the $\alpha 3$ domain of MICB and demonstrated that overexpressing MICB.A2 prevented tumor formation by the mouse prostate tumor cell line TC2. It was also demonstrated that, when soluble MICB was persistently present, expression of the shedding-resistant MICB.A2 on the tumor cell surface did not prevent or delay tumor formation in vivo. This study signifies the impact of MIC shedding on tumor formation and the magnitude of sustained MIC-induced NKG2D immunity in preventing early tumor development.

Although the mechanisms of MIC shedding are still under investigation (Salih et al., "Down-Regulation of MICA on Human Tumors by Proteolytic Shedding," *J Immunol* 169: 4098-102 (2002); Kaiser et al., "Disulphide-isomerase-enabled Shedding of Tumour-associated NKG2D Ligands," *Nature* 447: 482-6 (2007); Le Maux et al., *Int Immunol* 20: 801-10 (2008), which are incorporated herein by reference in their entirety), clinical evidence has demonstrated that shedding of MIC is common in MIC-positive cancers, such as prostate, colon, breast adenocarcinomas, and melanomas (Groh et al., "Broad Tumor-associated Expression and Recognition By Tumor-derived Gamma Delta T Cells of MICA and MICB," *Proc Natl Acad Sci USA* 96:6879-84 (1999); Vetter et al., "Expression of Stress-induced MHC Class I Related Chain Molecules on Human Melanoma," *J Invest Dermatol* 118: 600-5 (2002); Jinushi et al., "Expression and Role of MICA and MICB in Human Hepatocellular Carcinomas and Their Regulation by Retinoic Acid," *Int J Cancer* 104: 354-61 (2003); Wu et al., "Prevalent Expression of the Immunostimulatory MHC Class I Chain-related Molecule is Counteracted by Shedding in Prostate Cancer," *J Clin Invest* 114: 560-8 (2004), which are incorporated herein by reference in their entirety). In these patients, the function of NK and/or CD8 T cells was compromised due to soluble MIC-induced internalization of the NKG2D receptor (Wu et al., "Prevalent Expression of the Immunostimulatory MHC Class I Chain-related Molecule is Counteracted by Shedding in Prostate Cancer," *J Clin Invest* 114: 560-8 (2004); Groh et al., "Tumour-derived Soluble MIC Ligands Impair Expression of NKG2D and T-cell Activation," *Nature* 419: 734-8 (2002); Doubrovina et al., "Evasion from NK Cell Immunity by MHC Class I Chain-related Molecules Expressing Colon Adenocarcinoma," *J Immunol* 171:6891-9 (2003); Raffaghello L, et al., *Neoplasia* 6: 558-68 (2004), which are incorporated herein by reference in their entirety). Recent studies have demonstrated that MIC expression is not restricted in tumor cells and that MIC can be induced in cells in response to DNA damage (Gasser et al., "The DNA Damage Pathway Regulates Innate Immune System Ligands of the NKG2D Receptor," *Nature* 436: 1186-90 (2005), herein incorporated by reference in its entirety), a prior event to transformation. Therefore, the current study indicates that, in the event of malignant transformation, inhibiting shedding of MIC from MIC-positive transformed cells can prevent the initiation of tumor formation.

Human MICB was overexpressed rather than mouse NKG2D ligands in this study for the following rationales. First, MIC has been shown to be shed by tumor cells in cancer patients, thus the study is clinically relevant. Secondly, MICB has been shown to interact with mouse NKG2D and MICB-positive cells are sensitive to mouse NK cells (Diefenbach et al., "Ligands for the Murine NKG2D Receptor: Expression by Tumor Cells and Activation of NK Cells and Macrophages," *Nat Immunol* 1: 119-26 (2000); Dunn et al., "Human Cytomegalovirus Glycoprotein UL16 Causes Intracellular Sequestration of NKG2D Ligands, Protecting Against Natural Killer Cell Cytotoxicity," *J Exp Med* 197: 1427-39 (2003), which are hereby incorporated by reference in their entirety). It has also been shown that MICB was shed by the mouse prostate cell line TC2 in the same pattern as MIC shedding in prostate cancer patients (Wu, unpublished). Thirdly, although mouse NKG2D ligands are functionally similar to human MIC in NK cell activation, these molecules are structurally different and may have different physiological roles. Mouse NKG2D ligands lack the $\alpha 3$ domain and are mostly GPI-linked proteins (Cerwenka et al., "NKG2D Ligands: Unconventional MHC Class I-like Molecules Exploited by Viruses and Cancer," *Tissue Antigens* 61: 335-43 (2003), which is hereby incorporated by reference in its entirety); in addition, little is known about what controls the expression of mouse NKG2D ligands in vivo and whether they would shed in a similar fashion to MIC in human tumor cells. Lastly, different from human NKG2D ligands, studies have shown that naturally expressed mouse NKG2D ligands on tumor cells may not cause tumor rejection, largely due to insufficient levels of the ligand expression (Diefenbach et al., "Rae1 and H60 Ligands of the NKG2D Receptor Stimulate Tumour Immunity," *Nature* 413: 165-71 (2001), which is hereby incorporated by reference in its entirety) or low affinity of binding to NKG2D (Diefenbach et al., "Selective Associations with Signaling Proteins Determine Stimulatory Versus Costimulatory Activity of NKG2D," *Nat Immunol* 3:1142-9 (2002), which is hereby incorporated by reference in its entirety). In this study, although TC2 cells express some levels of mouse NKG2D ligand RAE-1 variants, TC2 tumors were palpable in SCID mice within a week after implantation and grew aggressively (FIG. 4), indicating that the levels of activating RAE-1 variants expressed by TC2 cells are too low to induce anti-tumor immunity. This was also supported by the low binding ability of soluble mouse NKG2D to TC2 cells (FIG. 3a). Together, the choice of MICB makes the in vivo study described here more clinically relevant to human cancers.

In activated mouse NK cells, due to alternative DNA splicing, two isoforms of NKG2D couple with two intracellular adaptors, DAP10 and DAP12, which trigger phosphatidyl inositols kinase (PI3K) and Syk family protein tyrosine kinase, respectively (Diefenbach et al., "Selective Associations with Signaling Proteins Determine Stimulatory Versus Costimulatory Activity of NKG2D," *Nat Immunol* 3: 1142-9 (2002); Zompi et al., "NKG2D Triggers Cytotoxicity in Mouse NK Cells Lacking DAP12 or Syk Family Kinases," *Nat Immunol* 4: 565-72 (2003), which is hereby incorporated by reference in its entirety). In humans, NKG2D only associates with DAP10. However, in mice NK cells lacking DAP12 or Syk family kinases, the DAP10-PI3K pathway alone is sufficient to initiate ligand-induced NKG2D-mediated killing of target cells (Zompi et al., "NKG2D Triggers Cytotoxicity in Mouse NK Cells Lacking DAP12 or Syk Family Kinases," *Nat Immunol* 4: 565-72 (2003), which is hereby incorporated by reference in its entirety). Thus, regardless that signaling via mouse NKG2D is more complex than human NKG2D, the impact of NKG2D ligand shedding on tumor formation as found in the current study is significant in both species.

Most of the in vitro evidence suggests that engagement of tumor cell surface MIC to NKG2D can activate NK cell immunity against tumor cells. Thus, expression of MIC on tumor cells is proposed to activate host protective anti-tumor immune response. However, most of the epithelial originated human cancer cells were found to have MIC expressed on the surface, indicating the ineptness of MIC-induced NK cell immunity. Consistent with clinical observations, it was also shown that overexpressing the natural cleavable form of MICB in TC2 cells has no significant effect on tumor growth in vivo. Although overexpressing the non-cleavable shedding-resistant MICB.A2 can cause TC2 tumor rejection, this effect can be inhibited by the persistent presence of soluble MICB (FIG. 6a). Together, these data indicate that the role of MIC in host tumor immune surveillance is determined by whether MIC is all or partially membrane-bound. If substantially all of the MIC molecules are sustained as membrane-bound and non-cleavable proteins, significant expression of MIC activates NK cell-mediated host immunity. In contrast, if a portion of the MIC molecules is cleaved and becomes soluble, tumor cells cannot be targeted by NK cells due to soluble MIC-mediated masking and possible down-regulation of the receptor NKG2D, regardless of abundant MIC remaining on the tumor cell surface as observed in many cancer patients (Groh et al., "Broad Tumor-associated Expression and Recognition By Tumor-derived Gamma Delta T Cells of MICA and MICB," *Proc Natl Acad Sci USA* 96:6879-84 (1999); Vetter et al., "Expression of Stress-induced MHC Class I Related Chain Molecules on Human Melanoma," *J Invest Dermatol* 118: 600-5 (2002); Jinushi et al., "Expression and Role of MICA and MICB in Human Hepatocellular Carcinomas and Their Regulation by Retinoic Acid," *Int J Cancer* 104: 354-61 (2003); Wu et al., "Prevalent Expression of the Immunostimulatory MHC Class I Chain-related Molecule is Counteracted by Shedding in Prostate Cancer," *J Clin Invest* 114: 560-8 (2004), which are herein incorporated by reference in their entirety).

In summary, these data provide the first in vivo conclusive evidence of the impact of MIC shedding on tumor growth and of the importance of sustained MIC ligand-NKG2D receptor interaction in control of tumor growth. In addition, these results show no significant difference in tumor growth among animals whether the natural form of MICB or soluble recombinant MICB was expressed. Without wishing to be bound by theory, this observation implies that wild-type MIC expression in established tumors may have very little effect on inducing host NK cell activation, due to shedding of MIC by tumor cells and the consequent dampening of host immunity. Together, these results indicate that strategies to sustain the recognition of NKG2D receptor and tumor MIC ligand can be used to promote NK cell-mediated killing of cancer cells.

Example 2

Short Motif(s) in the Alpha-3 Ectodomain of MICA Are Essential for Tumor Shedding: Anti-Tumor Therapeutic Targets The MHC class I chain-related family of molecule MICA was found to be induced in most transformed human epithelial tumors, including breast, lung, ovary, prostate, kidney, and colon carcinomas (Wu et al., "Prevalent Expression of the Immunostimulatory MHC Class I Chain-related Molecule is Counteracted by Shedding in Prostate Cancer," *J Clin Invest* 114 (4):560-8 (2004); Groh et al., "Broad Tumor-associated Expression and Recognition By Tumor-derived Gamma Delta T Cells of MICA and MICB," *Proc Natl Acad Sci USA* 96 (12):6879-84 (1999); Vetter et al., "Expression of Stress-induced MHC Class I Related Chain Molecules on Human Melanoma," *J Invest Dermatol* 118 (4):600-5 (2002); Seliger et al., *Trends Immunol* 24 (2):82-7 (2003), which are hereby incorporated by reference in their entirety). MICA was identified as a ligand of NKG2D, a C-type lectin-like stimulatory immune receptor that is expressed by all human NK cells, CD8 T cells, and a subset of gamma/delta T cells (Groh V, et al., *Science* 279 (5357):1737-40 (1998); Bauer et al., "Activation of NK Cells and T Cells by NKG2D, A Receptor for Stress-inducible MICA," *Science* 285(5428):727-9 (1999); Diefenbach et al., "The Innate Immune Response to Tumors and Its Role in the Induction of T-cell Immunity," *Immunol Rev* 188:9-21 (2002); Raulet D H., "Roles of the NKG2D Immunoreceptor and its Ligands," *Nat Rev Immunol* 3:781-90 (2003), which are hereby incorporated by reference in their entirety).

In vitro experiments have shown that engagement of NKG2D by MIC(A or B) expressed on the tumor cell surface triggers NK cell anti-tumor cytotoxic responses (Seliger B, et al., (2003), supra; Bauer et al., (1999), supra). This engagement also co-stimulates antigen-specific cytotoxic T cell (CTL) mediated anti-tumor immunity and is necessary for activation of $V_\delta 1\gamma\delta$ T cells (Groh et al., "Costimulation of CD8alphabeta T Cells by NKG2D via Engagement by MIC Induced on Virus-infected Cells," *Nat Immunol* 2 (3):255-60 (2001); Wu et al., "T Cell Antigen Receptor Engagement and Specificity in the Recognition of Stress-inducible MHC Class I-related Chains by Human Epithelial Gamma Delta T Cells," *J Immunol* 169 (3):1236-40 (2002), which are hereby incorporated by reference in their entirety). Xenograft MIC-positive human epithelial tumors were either rejected or exhibited growth inhibition in SCID mice (Doubrovina et al., "Evasion from NK Cell Immunity by MHC Class I Chain-related Molecules Expressing Colon Adenocarcinoma," *J Immunol* 171 (12):6891-9 (2003); Friese et al., "MICA/NKG2D-mediated Immunogene Therapy of Experimental Gliomas," *Cancer Res* 63 (24):8996-9006 (2003), which are hereby incorporated by reference in their entirety), whereas these effects were not observed in animals xenografted with MIC-negative human epithelial tumors. Thus, MIC is proposed as a specific target on epithelial tumor cells to mark nascent tumors for immune surveillance (Nausch et al., "NKG2D Ligands in Tumor Immunity," *Oncogene* 27 (45):5944-58 (2008); Waldhauer et al., "NK Cells and Cancer Immunosurveillance," *Oncogene* 27 (45):5932-43 (2008), which are hereby incorporated by reference in their entirety).

Clinical evidence suggests that tumors may evade the MIC-induced immunity by shedding of MIC. Studies have shown that malignant tumors, including breast, colon, lung, melanoma, and prostate cancers, shed MIC from the cell surface (Wu et al., "Prevalent Expression of the Immunostimulatory MHC Class I Chain-related Molecule is Counteracted by Shedding in Prostate Cancer," *J Clin Invest* 114 (4):560-8 (2004); Groh et al., "Tumour-derived Soluble MIC Ligands Impair Expression of NKG2D and T-cell Activation," *Nature* 419 (6908):734-8 (2002); Raffaghello et al., "Downregulation and/or Release of NKG2D Ligands as Immune Evasion Strategy of Human Neuroblastoma," *Neoplasia* 6 (5):558-68 (2004); Holdenrieder et al., "Soluble MICA in Malignant Diseases," *Int J Cancer* 118 (3):684-7 (2006); Marten et al., "Soluble MIC is Elevated in the Serum of Patients with Pancreatic Carcinoma Diminishing Gamma Delta T Cell Cytotoxicity," *Int J Cancer* 119 (10):2359-65 (2006); Salih et al., "Down-Regulation of MICA on Human Tumors by Proteolytic Shedding," *Hum Immunol* 67 (3):188-95 (2006) Jinushi M et al., *Proc Natl Acad Sci USA* 105 (4):1285-90 (2008), which are hereby incorporated by reference in their entirety). Tumor shedding of MICA may generate at least two negative effects to impair NKG2D-mediated NK cell anti-tumor immunity and antigen-specific CTL anti-tumor immune activation. One is the apparent loss of NKG2D-specific tumor cell surface target molecule MICA (Holdenrieder et al., "Soluble MICA in Malignant Diseases," *Int J Cancer* 118 (3):684-7 (2006); Marten et al., "Soluble MIC is Elevated in the Serum of Patients with Pancreatic Carcinoma Diminishing Gamma Delta T Cell Cytotoxicity," *Int J Cancer* 119 (10):2359-65 (2006), which are hereby incorporated by reference in their entirety). The other is tumor shedding-derived soluble MICA (sMICA)-induced endocytosis of NKG2D on NK and T cells (Groh V, et al., (2002), supra; Raffaghello L, et al., (2004), supra; Holdenrieder et al., (2006), supra; Marten et al., 5 (2006), supra; Salih et al., (2006), supra; Jinushi M et al., 2008, supra).

Because of the apparent negative effects of sMIC in impairing host anti-tumor immunity, inhibiting MIC shedding can have therapeutic utility. Multiple enzymes, such as disulphide-isomerase (Kaiser et al., "Disulphide-isomerase-enabled Shedding of Tumour-associated NKG2D Ligands," *Nature* 447 (7143):482-6 (2007), which is hereby incorporated by reference in its entirety), MMPs (Salih et al., "Down-Regulation of MICA on Human Tumors by Proteolytic Shedding," *J Immunol* 169 (8):4098-102 (2002); Le Maux Chansac et al., "Potentiation of NK Cell-mediated Cytotoxicity in Human Lung Adenocarcinoma: Role of NKG2D-dependent Pathway," *Int Immunol* 20 (7):801-10 (2008), which are hereby incorporated by reference in their entirety), or ADAMS (Waldhauer et al., "Tumor-associated MICA is Shed by ADAM Proteases," *Cancer Res* 68 (15):6368-76 (2008), which is hereby incorporated by reference in its entirety), have been suggested to be involved in MIC shedding. The functional complexity of these enzymes and proteases involved in tumor shedding make it unfeasible to develop specific enzyme inhibitors to inhibit shedding of MICA clinically. Therefore, identification of tumor shedding site(s) or motif(s) involved in or required for cleavage can provide targets for therapeutic inhibition of MIC cleavage. In this study, short amino acid motif(s) in the α3 ectodomain of MICA were identified that are required for shedding. These motifs can be targeted with antibody or small molecule preparations to inhibit tumor shedding of MIC for targeted cancer therapy.

Materials and Methods

Cell Lines and Serum Samples

The mouse prostate tumor cell line TRAMP-C2 (Gift from Dr. N M Greenberg) was grown in DMEM medium supplemented with 10% FCS, 5 µg/mL insulin, 5 µg/mL transferrin, 5 ng/mL selenium (ITS), 1% fungi and 1% P/S. The human prostate tumor cell line, M12, (Bae et al., Metastatic Sublines of an SV40 Large T Antigen Immortalized Human Prostate Epithelial Cell Line," *Prostate* 34 (4):275-82 (1998), which is hereby incorporated by reference inits entirety) was cultured in RPMI1640 medium supplemented with 5% FCS, 10 ng/ml EGF, 0.02 mM dexamethasone, 5 µg/ml insulin, 5 µg/ml transferrin, 5 ng/ml selenium, fungizone, and gentamicin at 37° C. with 5% CO2. C1R-MICA cells (gift from Dr. T. Spies) were cultured in RPMI-1460 supplemented with 10% FCS and 1.0 mg/ml of G418. The Eco-phoenix retrovirus package cell line was cultured in DMEM medium supplemented with 10% FCS, Sodium pyruvate, and 1% P/S, NK-92 cells (ATCC No. CRL-2407) are maintained in MEM-α media supplemented with 12.5% FCS, 12.5% horse serum, 1% P/S, and 1000 U/mL of IL-2. Serum samples from prostate cancer patients were obtained from Seattle VA Clinic. The study was approved by Institutional Human Subject Review Board.

Overexpressing Human MICA in TRAMP-C2 Cells

The cDNA of MICA01 was kindly provided by Dr. A. Steinle (University of Tübingen, Tübingen, Germany). cDNAs were subcloned into the retroviral vector pBMN-GFP (Orbigen Inc, San Diego, Calif.). The Eco-pheonix package cell line was transfected by the recombinant plasmid. The recombinant retrovirus containing the MICA gene was used to infect the TRAMP-C2 cells. Overexpression of MICA in TRAMP-C2 cells was verified by Flow cytometry analyses with the specific antibody 6D4.6 (Biolegend, San Diego, Calif.).

Generation of MICA Mutants

All of the MICA mutants were generated by recombinant PCR techniques (Horton et al., "Gene Splicing by Overlap Extension: Tailor-made Genes Using the Polymerase Chain Reaction," *Biotechniques* 8 (5):528-35 (1990), which is hereby incorporated by reference in its entirety) and confirmed by DNA sequencing. Error-free cDNAs were subcloned into the GFP-IRES pBMNZ retroviral vector (Orbigen) and expressed in TRAMP-C2 cells as described above.

Immunoprecipitation and Western-Blotting

Cells were lysed in Baserga lysis buffer (50 mM HEPES, 150 mM NaCl, 1.5 mM $MgCl_2$, 1 mM EGTA, 1% Triton X-100) with Complete protease inhibitors (Roche Applied Science) for 30 min on ice. Cell culture supernatant or clear cell lysate was incubated with 6D4.6 Ab and ultralink immobilized protein A/G plus (Pierce). Immune complexes were treated with PNGaseF for 1 h at 37° C., separated by SDS/PAGE, and transferred onto a nitrocellulose membrane. The membrane was blotted with rabbit anti-human MICA polyclonal Ab (Santa Cruz Biotechnology) and donkey anti-rabbit-IgG-HRP (Santa Cruz Biotechnology). Proteins were detected with ECL reagents (GE Healthcare).

MIC Shedding Assay

Cells were seeded at the density of 4×10$^5$ cells/well in a 6-well plate in complete media overnight and the media was replaced with 1 ml/well serum-free media for 24 hrs. Supernatant was collected and filtered through a 0.45 μm membrane. Cells were lysed with 1 ml lysis buffer. The amount of soluble MICA in the supernatant and MICA in the cell lysates was measured using a human MICA DuoSet sandwich ELISA kit (R&D Systems). The degree of shedding is expressed as the ratio of sMICA in the supernatant to MICA in the lysates.

Cytotoxicity Assay

NK-92 cells were used as effector cells. Cytotoxicity was performed in triplicates using the standard 4 h 51Cr release assay as previously described (Wu et al., (2004), supra).

Purification of Tumor Shedding-Derived Soluble MICA from Cell Culture Supernatant The 6D4.6 antibody was conjugated to the NHS-activated Sepherose Fast Flow (GE Health care) using the manufacturer's instructions. Complete protease inhibitor cocktail tablets (Roche Applied Science) were added to the cell culture supernatant immediately after collection. The supernatant was filtered through a 0.2 μm membrane to remove cell debris before being loaded on the antibody conjugated Sepharose Fast Flow column. The column was washed with 50 mM NaAc (pH4.5) buffer and sMICA was eluted by 0.1M Citrate buffer (pH2.5). The elution was immediately neutralized with 1.5M Tris (pH 8.3) and concentrated by the Biomax PES-5 column (Centricon Plus-20, Millipore).

Sample Preparation for Mass Spectrometry

For in-gel digestion, purified sMICA was treated with PNGaseF to remove oligosaccharide chains before being loaded on a 10% SDS-PAGE gel. After Commassie Blue staining, the sMICA bands were excised, washed with 50 mM NH$_4$HCO$_3$, dehydrated in acetonitrile (ACN), and dried under a vacuum. The protein bands were incubated with 6.25 ng/μL of trypsin overnight at room temperature and the supernatant was collected. The protein bands were washed once with 5% ACN/0.1% TFA and once with 50% ACN/0.1% TFA. The supernatant from each wash was collected, combined with the digestion supernatant, and dried to 10-20 μL for analysis. For in-solution digestion, ~50 μg of protein was denatured using 6M urea, reduced with DTT and alkylated with iodoacetamide. Sequencing grade trypsin or Glu-C (Roche Diagnostics, Indianapolis, Ind.) was added to the final mixture in a 30:1 ratio and the digestion was allowed to proceed at 37° C. overnight. Peptides were then desalted on a Vydac C18 microspin column (The Nest Group, Southborough, Mass.) according to the manufacturer's instructions.

Mass Spectrometry and HPLC

All data were acquired in three technical replicates. Peptide digests were analyzed by electrospray ionization in the positive ion mode using the LTQ-Orbitrap (Thermo Fisher, San Jose, Calif.). For each injection, an estimated amount of 0.1 μg of digested MICA sample was loaded onto the pre-column at 4 μL/min in water/acetonitrile (95/5) with 0.1% (vol/vol) formic acid. Peptides were eluted using a linear acetonitrile gradient flowing at 250 nL/min using a mobile phase consisting of: A, water, 0.1% formic acid; B, acetonitrile, 0.1% formic acid (Yi et al., "A Microcapillary Trap Cartridge-microcapillary High-performance Liquid Chromatography Electrospray Ionization Emitter Device Capable of Peptide Tandem Mass Spectrometry at the Attomole Level on an Ion Trap Mass Spectrometer with Automated Routine Operation," *Rapid Communications in Mass Spectometry* 17 (18): 2093-8 (2003), which is hereby incorporated by reference in its entirety). The gradient program was: 0 min: A (95%), B (5%), 55 min: A (65%), B (35%), 60 min: A (15%), B (85%), 65 min: A (5%), B (95%), 75-90 min: A (95%), B (5%); (stop). Data-dependent analyses were carried out using MS survey scans in the Orbitrap followed by data-dependent selection of the three most abundant precursor ions for tandem mass spectrometry in the LTQ. Collision energy was set to 35% for CID in the LTQ (Nunn et al., "Comparison of a *Salmonella typhimurium* Proteome Defined by Shotgun Proteomics Directly on an LTQ-FT and By Proteome Pre-Fractionation on an LCQ-DUO," *Brief Funct Genomic Proteomic* 5 (2):154-168 (2006), which is hereby incorporated by reference in its entirety).

Database Search

Raw data from mass spectrometric acquisitions were converted to .dta file format using Bioworks 3.0 software (Thermo Fisher). Database search was performed with Phenyx (GeneBio SA, Geneva, Switzerland) against the human International Protein Index (IPI) database. Precursor ion tolerance was set to 2.1 Da. Unspecific searches (no enzyme specified) were performed allowing two missed cleavages. Methionine residues were considered as being present in reduced and oxidized form. Cysteine residues were considered alkylated with iodoacetamide.

Results

Conserved Shedding Pattern of MICA

Figure 7A:
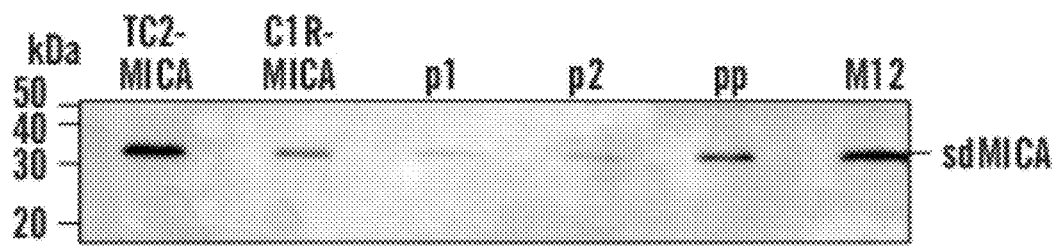
FIG. 7a shows the detection of tumor-shed soluble MIC (sdMIC) by Western-blot in various cells and sera of prostate cancer patients. 10 ml culture supernatant of $1\times10^6$ TRAMP-C2 (TC2)-MICA, C1R-MICA, and M12 cells, 3 ml serum from two prostate cancer patients (p1, p2), and 5 ml pooled sera from 5 prostate cancer patients (pp5) were incubated with the anti-MIC mAb 6D4.6. The sdMICA immunocomplexes were separated on SDS-PAGE and immunoblotted with goat anti-MICA antibody H-300.

The patterns of MIC shedding were first analyzed from a MICA-expressing mouse prostate tumor cell line TRAMP-C2, a human prostate tumor cell line M12, a MICA-expressing human B cell lymphoma cell line C1R, and human prostate carcinomas. Serum from two individual prostate cancer patients was used and pooled sera from five prostate cancer patients was used to assay the pattern of shedding-derived soluble MIC (thereafter termed sdMIC) by prostate carcinomas. The mAb 6D4.6 which is specific to the α1α2 ectodomain of MIC was used to immunoprecipitate sdMIC from the supernatant of cell cultures and the sera from prostate cancer patients. The immunocomplexes were separated on an SDS-PAGE gel and sdMIC was identified by immunoblotting with the rabbit anti-human MIC polyclonal antibody, H-300. As shown in FIG. 7a, the sdMIC resulted from shedding by TRAMP-C2-MICA, M12, and C1R-MICA cells and from sera of prostate cancer patients showed similar molecular weights on the SDS-PAGE gel. After removal of sugar chains with PNGaseF, sdMIC from all cell lines and patients' sera showed a molecular weight of approximately 30-32 kDa. This indicates that MICA was shed at conserved sites in tumor cell lines and carcinomas from prostate cancer patients.

Figure 8B:
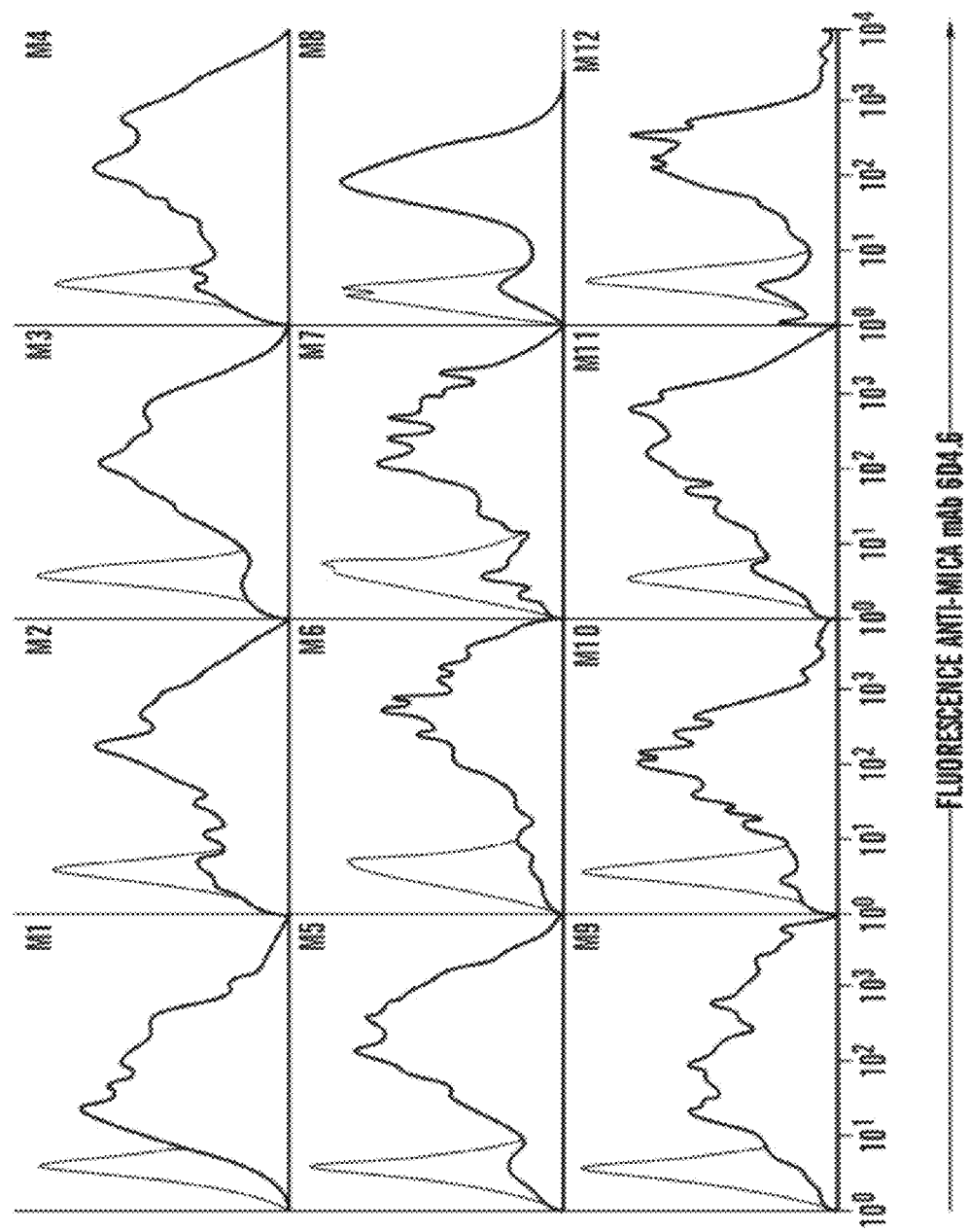
FIG. 8b depicts flow cytometry histograms showing surface expression of MICA mutants in TRAMP-C2 cells (filled profiles). TRAMP-C2 cells were transduced with retrovirus expressing mutant MICA and stained with anti-MIC mAb 6D4.6 followed by a PE-conjugated secondary reagent. Cells were analyzed with Cellquest software. Open profiles, negative control TRAMP-C2 cells stained with 6D4.6 antibody.

A region in the α3 domain (aa 215-274) of MICB, a closely related molecule of MICA, is required for mediating tumor shedding (Wu et al., "Obstructing Shedding of the Immunostimulatory MHC Class I Chain-related Gene B Prevents Tumor Formation," *Clin Can Res* 15 (2):632-40 (2009), which is hereby incorporated by reference in its entirety). It was addressed whether a similar region in MICA is critical for shedding. A region of amino acid 218-274 of MICA was replaced with corresponding sequence of HLA-A2 (FIG. 7b) to generate the mutant MICA.A2 and over-expressed MICA.A2 in TRAMP-C2 cells (FIG. 7c). ELISA assays show that TRAMP-C2 cells shed MICA, but not MICA.A2 (FIG. 7d), indicating that sequences in the region of 218-274 are necessary for shedding of MICA. To further define residues or peptide motifs that may be critical for MIC shedding, a serial of MICA mutants within this region was constructed (FIG. 8a). These mutants were stably expressed in the TRAMP-C2 cell line using a retroviral system. Expression of these mutant forms of MICA on the surface of TRAMP-C2 cells was confirmed by flow cytometry analyses (FIG. 8b). Cell culture supernatant and cell lysates of TRAMP-C2 cells expressing these MICA mutants were collected respectively and immune precipitated with the anti-MIC mAb 6D4.6. Immune complexes were analyzed by western-blot to assess the appearance of sdMICA in the culture supernatant.

Figure 8C:
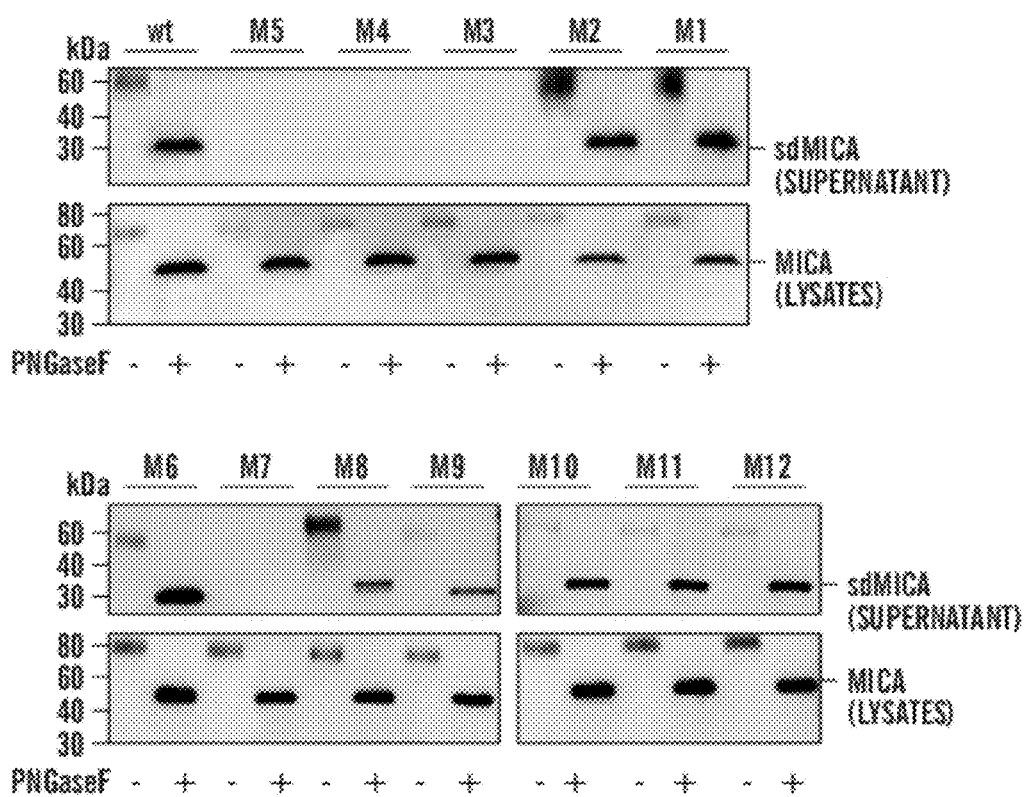
FIG. 8c depicts Western blots showing the shedding characteristics of MICA mutants in TRAMP-C2 cells. Culture supernatant (SN) was collected and incubated with the mAb 6D4.6 which recognizes the α1α2 domain of MIC. Meantime, cell lysate (LY) was immunoprecipitated with mAb 6D4.6 to confirm the expression of MIC. Immunocomplexes containing sdMIC and MIC were separated on SDS-PAGE and detected by the goat anti-MIC antibody E-16 specific for the N-terminus of MIC. PNGaseF was used for deglycosylation. Data represents three independent experiments.

Three mutants were constructed to cover parts of the region of aa 218-274: M1 (residue $Q^{218}$-$D^{236}$), M2 residue $C^{250}$-$F^{257}$), and M3 (residue $N^{238}$ to $R^{248}$). Only mutant M3, was shown to be shedding-resistant (FIG. 8c), indicating that residues in the region of $N^{243}$ to $R^{253}$ are critical in mediating shedding. To further define residues or regions that are required for MICA shedding, several mutants were constructed to cover variable lengths of the region $N^{243}$ to $R^{253}$ (FIG. 8a). Mutants M5 and M7, which cover the shortest motif from the N-terminus (N243GTYQT) (SEQ ID NO: 1) or the C-terminus (Y264QTWVATR) (SEQ ID NO: 2) of the region $N^{243}$ to $R^{253}$ respectively, were identified to be shedding-resistant (FIG. 8c). Specifically, no sdMICA was seen in the culture supernatant, while these mutant MICA molecules were abundantly expressed on the surface of TC2 cells as shown by flow cytometry analyses (FIG. 8b).

Mutants M5 and M7 contain common mutations covering residues $Y^{246}$ to $T^{248}$. To further investigate how various mutations in $Y^{246}$ to $T^{248}$ would affect shedding, mutants M10, M11, and M12 were constructed (FIG. 8a). None of these mutants interfered with shedding (FIG. 8c).

The Shedding-Sensitive Motif(s) is/are not Host-Specific

Figure 9A:
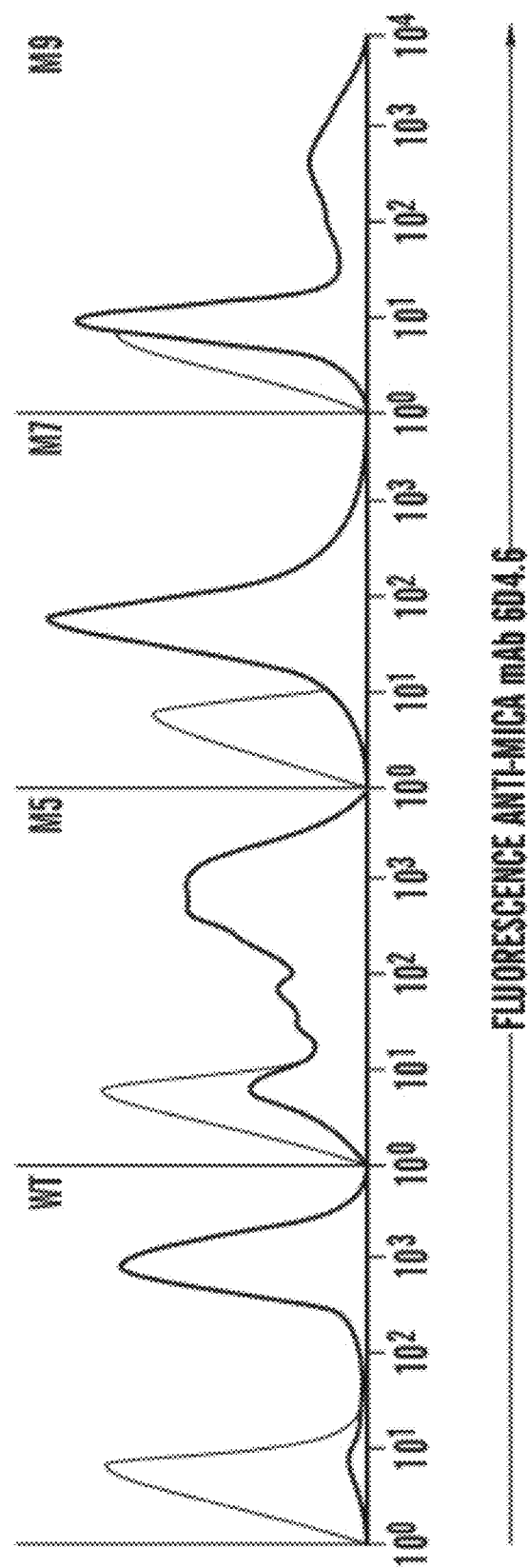
FIG. 9a depicts a flow cytometry histogram showing surface expression of the wild-type MCA (wtMICA) and shedding-resistant MICA mutants M5 and M7 in C1R cells (filled profiles). C1R cells were transduced with retrovirus expressing wtMICA, MICA mutants M5 and M7 respectively and stained with anti-MIC mAb 6D4.6 followed by a PE-conjugated secondary reagent. Open profiles, negative control C1R cells stained with 6D4.6 antibody.
Figure 9B:
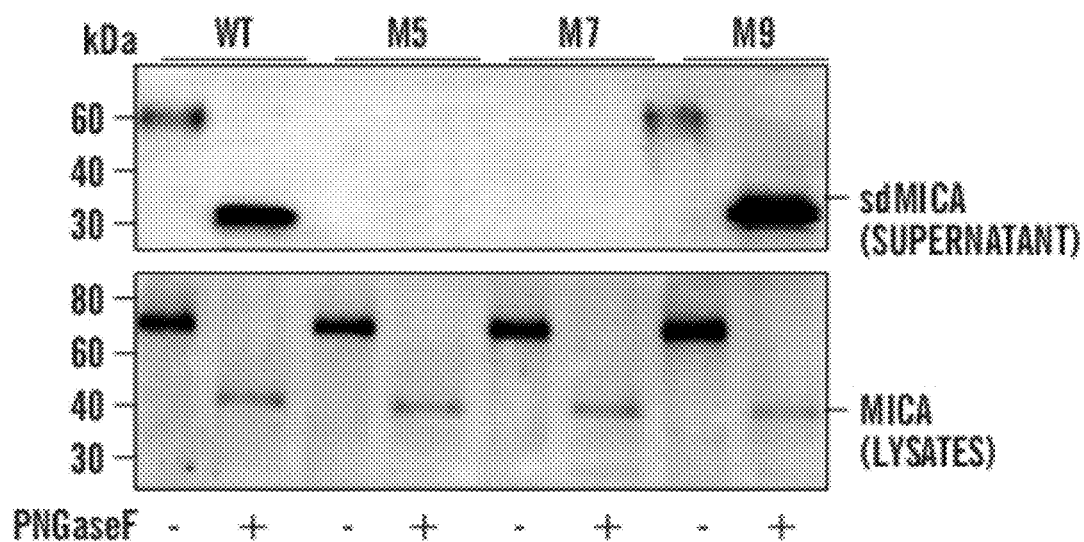
FIG. 9b shows that shedding was assayed by immunoprecipitation and Western-blotting as described in TC2 cells.
Figure 9C:
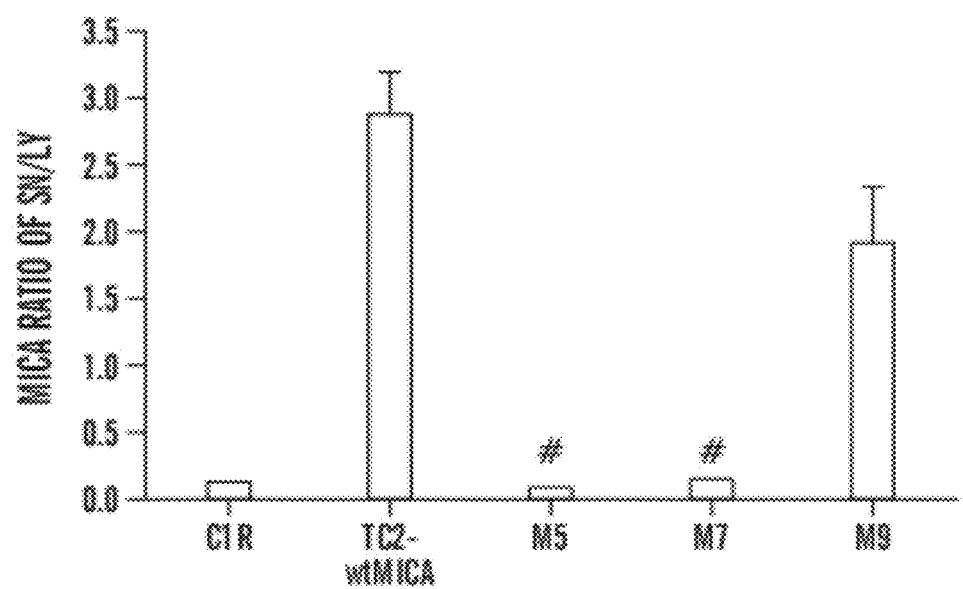
FIG. 9c shows that the resistance to shedding of M5 and M7 in C1R cells was confirmed by ELISA as described in TRAMP-C2 cells. C1R cells do not express endogenous MIC and were used as negative controls for MIC. #, no significant difference from background value of C1R cells. Data represents three independent experiments.

It was investigated whether the mutant M5 or M7 is also shedding-resistant in human tumor cell lines. MICA-M5 and MICA-M7 were stably expressed in human B-cell lymphoma C1R cell lines using a retroviral expression vector (FIG. 9a). Culture supernatant was collected for immunoprecipitation and Western Blotting analyses. The degree of shedding was also assayed by ELISA as described above. No shedding was detected of these two mutants in C1R cells (FIGS. 9b and 9c), indicating that the identified short shedding-sensitive motif is not host-specific.

Mass Spectrometry Analyses of sdMICA

To address whether the two shedding-sensitive motifs identified may contain potential MICA shedding site(s), mass spectrometric analyses was performed on the sdMICA from TRAMP-C2 and C1R cells. sdMICA was purified from the culture supernatant of TRAMP-C2-MICA or C1R-MICA cells using the mAb 6D4.6 conjugated NHS-activated Sepharose Fast Flow column. The eluted fraction was assayed by Western-blotting with the MICA-specific antibody E-16 to confirm the identity of soluble form of MICA (data not shown). Purified sdMICA was deglycosylated, in-gel trypsin digested, and analyzed on an LTQ-Orbitrap mass spectrometer. The recombinant soluble MICA (rsMICA) sample from a commercial source was analyzed in parallel as a control to ensure the quality of the sample preparation and instrumental accuracy. The commercial rsMICA was expressed in E. Coli and covers the sequence of the entire extracellular domain and the near-transmembrane region of MICA (aa E1-S296, FIG. 1b)

Three peptides with non-tryptic C- or N-termini were present in all samples, however, one other peptides with non-tryptic C-termini was present only in the sdMICA samples, not in the control rsMICA sample (FIG. 10a). This peptide has sdMICA-specific non-tryptic C-terminus of $FTCYME^{266}$ (SEQ ID NO: 114). This finding was consistent in four independent experiments conducted in MS-Spectrometry facilities at two Institutions.

The in gel-trypsin mass-spectrometry analyses of commercial rsMICA recovered sequences only up to $PVPSGK^{281}$ (SEQ ID NO: 115) (data not shown), which indicated the possibility of incomplete extraction of peptides from the gel. To test this, sdMICA and control rsMICA were digested with trypsin in-solution. Mass spectrometric analysis of the in-solution digest did not provide sequence coverage beyond $K^{281}$ of the extracellular domain (data not shown).

The incomplete sequence coverage of control rsMICA during tryptic digestion analyses could be due to exclusion of small peptides (less than 6 aa) that were generated by cleavage. To compensate this limitation, peptide digests were also analyzed using the GluC protease (cleaves at C-terminal to residue E or D). In the analysis of GluC digests, several non-GluC peptides were identified that contained a staggered C-terminus proximal to or in the near-transmembrane region in all the samples (FIG. 10b). Most of these C-termini were also reported in other studies (Le Maux Chansac et al., "Potentiation of NK Cell-mediated Cytotoxicity in Human Lung Adenocarcinoma: Role of NKG2D-dependent Pathway," Int Immunol 20 (7):801-10 (2008), which is hereby incorporated by reference in its entirety). This indicates that the near-transmembrane region of MICA is susceptible to non-specific exopeptide activity.

Figure 12A:
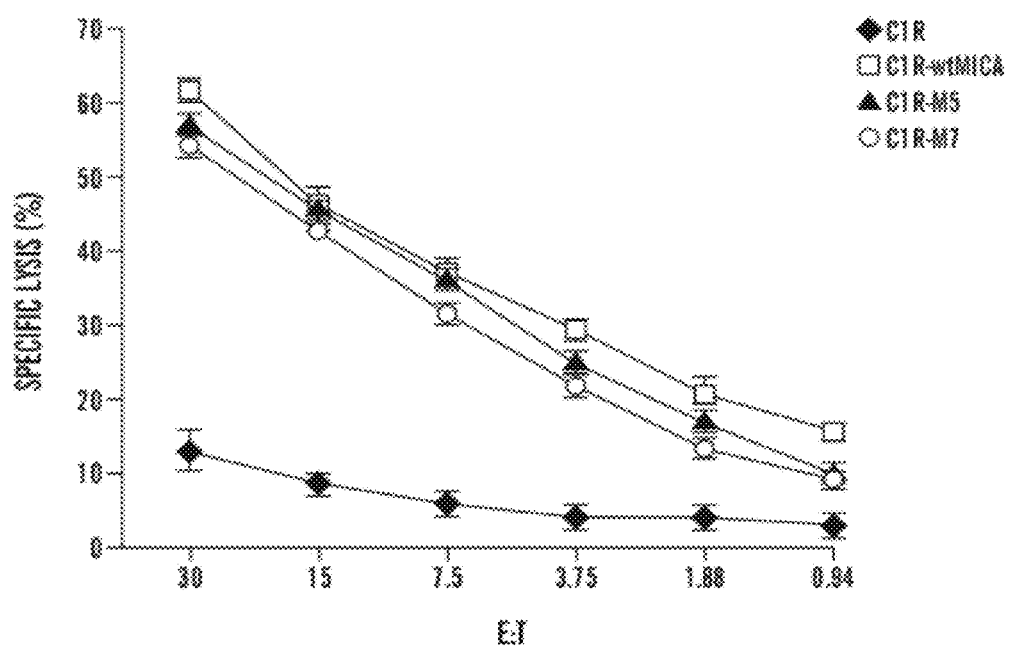
FIG. 12a shows specific lysis of NK-92 cells against M5 or M7-expressing C1R cells. C1R-MICA and C1R cells are used as positive and negative controls.
Figure 12B:
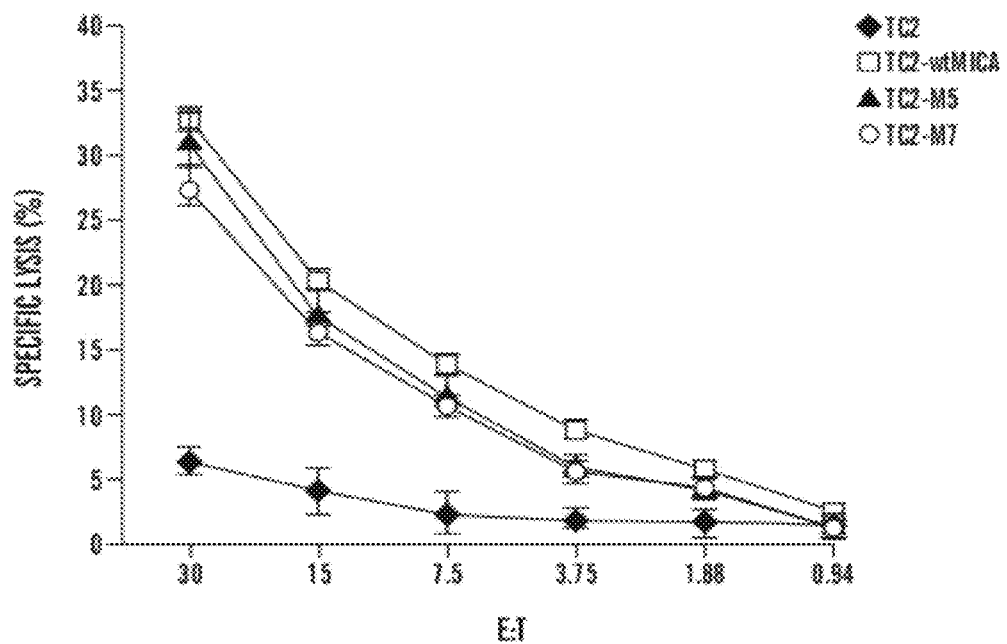
FIG. 12b shows specific lysis of NK-92 cells against M5 or M7-expressing TRAMP-C2 cells. TRAMP-C2-MICA and TRAMP-C2 cells are used as positive and negative controls. E:T, effector:Target. Data represents three independent experiments.

To further investigate how the region covering $FTCYME^{266}$/H (SEQ ID NO: 116) and the near transmembrane region would influence MICA shedding, mutants M13 and M14 were constructed (FIG. 12a) that together span the two regions, respectively. When overexpressed in TRAMP-C2 cells (FIG. 12b), neither mutation stopped MICA shedding (FIG. 12c). However, mutant M13 has reduced shedding of MICA (FIG. 12d).

NKG2D-Dependent Recognition of the Shedding-Resistant MICA by NK Cells

Since NKG2D only interacts with the α1α2 ectodomain of MIC (Horton et al., "Gene Splicing by Overlap Extension: Tailor-made Genes Using the Polymerase Chain Reaction," Biotechniques 8 (5):528-35 (1990); Li et al., "Complex Structure of the Activating Immunoreceptor NKG2D and its MHC Class I-like Ligand MICA," Nat Immunol 2 (5):443-51 (2001), which are hereby incorporated by reference in their entirety), mutations in the shedding-sensitive motifs are not likely to affect the recognition of MIC by NKG2D. In a previous study, it was shown that partial replacement of the α3 domain of MIC, which contains the shedding-sensitive motifs, with the corresponding sequence of HLA.A2 did not affect the recognition and binding ability of MIC to NKG2D (Bae et al., (1998), supra). To further confirm that tumor cells expressing the shedding-resistant MIC mutants are sensitive to NKG2D-dependent NK cell cytotoxicity, standard 4-h cytotoxicity assays were performed. Pure populations of M5 or M7 MICA mutants-expressing $C^1R$ and TRAMP-C2 cells were isolated by repeated flow cytometry sorting (data not shown) and used as target cells for NK-92 cells. C1R cells expressing M9 and M23 MICA mutants are sensitive to the cytotoxicity of NK-92 cells (FIG. 12).

Herein a motif in MIC is described that is critical for shedding by tumor cells. This motif is located in the extracellular α3 domain proximal to the transmembrane region. Mutation in this motif prevented the shedding event completely. Tumor shedding of MIC is commonly found in cancer patients and has been proposed to be one of the mechanisms of tumor evasion from immune surveillance and progress (Friese MA, (2003), supra; Nausch, and Cerwenka A. (2008), supra). As demonstrated conclusively in Example 1, tumor shedding of MIC promotes tumor progression, and obstructing shedding of MIC prevents tumor establishment in vivo.

Figures 11A, 11B:
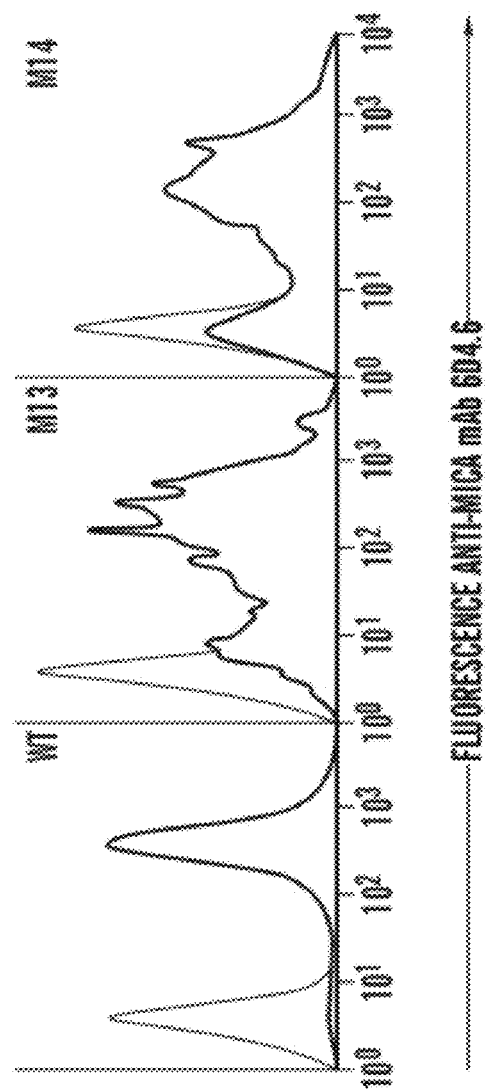
FIG. 11a shows mutations in the C-termus of the α-3 domain and the near-transmembrane region of MICA (SEQ ID NOs 27 to 30). The C-terminus of the α-3 domain of MICA was replaced with corresponding HLA-A2 sequence to generate mutant M13. The near-transmembrane region of MICA was replaced with corresponding HLA-A2 sequence to generate mutant M14.
FIG. 11b depicts histograms of flow cytometry analyses showing expression of the mutants in TRAMP-C2 cells (filled profiles). Cells were stained with anti-MIC mAb 6D4.6 followed by a PE-conjugated secondary reagent. Cells were analyzed with Cellquest software. Open profile, negative control TRAMP-C2 cells were stained with 6D4.6 antibody.
Figure 11C:
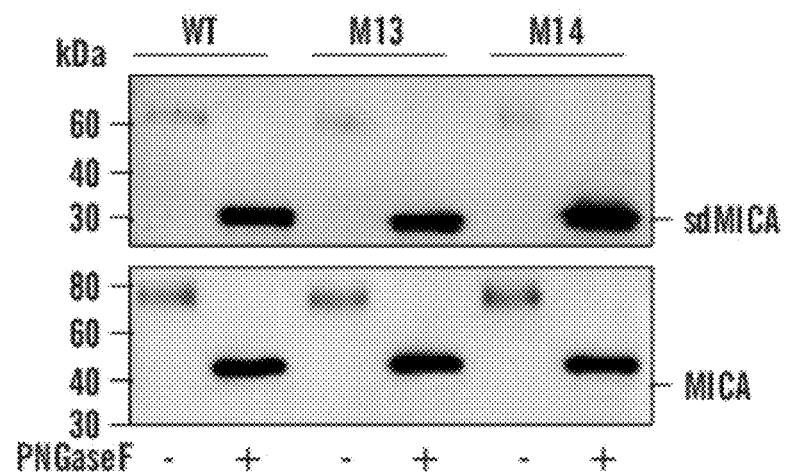
FIG. 11c shows that shedding was assayed by immunoprecipitation and Western-blotting as described above.
Figure 11D:
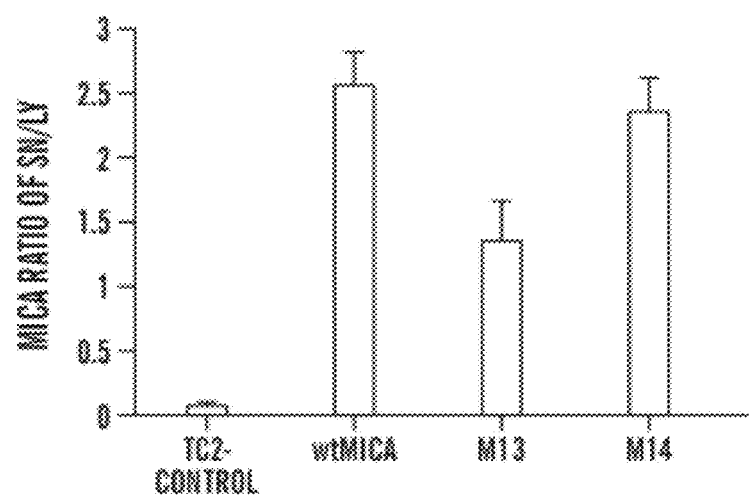
FIG. 11d depicts an ELISA showing shedding characteristics of M13 and M14 in TRAMP-C2. Data represents three independent experiments.

Several groups have attempted to identify cleavage site(s) of MIC by mass-spectrometry analyses for targeting MIC shedding. The domain proximal to the transmembrane region has been reported to generate peptides with non-tryptic staggered or ragged C-terminus and have been suggested to be involved in MIC(A) cleavage (Salih et al., (2006), supra; Le Maux Chansac B, et al., (2008), supra). Consistent with these findings, the mass-spectrometry analyses described herein of GluC digests of cleaved sMICA from the culture supernatant of MIC(A)-expressing tumor cell lines revealed similar peptides with a ragged C-terminus in the same region. In addition, it is shown that these peptides also appear in the control purified recombinant sMIC(A) sample, which was expressed in *E. Coli* (FIG. 10b). The data described herein indicates that the near transmembrane region of MIC(A) is susceptible to non-specific exopeptide activity and generates a sMIC(A) with a ragged C-terminus. The cleavage of MIC(A) by exopeptide activity is unlikely to be a process relevant to tumor shedding as it also appears in the control purified rsMIC(A) samples. Moreover, mutations in the near transmembrane region that generate the ragged C-terminus did not stop shedding, although they resulted in a reduction in the degree of shedding (FIG. 11d). This indicates that other sites besides this region may be involved in MIC(A) cleavage.

The tryptic mass spectrometric data described herein indicates there is an additional cleavage site located in the α3 domain of MIC(A) near the C-termini (FIG. 10a). Mutation in the region covering the potential site of YME$^{266}$/H did not stop shedding, but did result in a significant reduction in shedding.

It is widely recognized that tumor shedding of MIC results in impairment of NK cell and T cell anti-tumor immunity, however, the mechanism by which tumors shed MIC is not fully understood. The to-date studies have suggested that multiple mechanisms may be involved. Kaiser et al have suggested that ERp57 or disulphide isomerase is involved in MIC shedding (Salih et al., (2006), supra), whereas others have suggested that MMPs or ADAMS may be involved (Kaiser et al., (2007), supra; Salih et al., (2002), supra; Le Maux Chansac B, et al., (2008), supra). Because of incomplete knowledge of the mechanisms and the possibility of the involvement of multiple proteases in MIC(A) shedding, it would be difficult to overcome such a biological process with a specific protease inhibitor for clinical application. Further, most of the proteases found to be involved in MIC(A) shedding are also required for normal physiological function. Treatment with a protease inhibitor clinically would potentially generate high toxicity. On the other hand, MIC is generally absent in normal tissues and only present in transformed or some viral infected cells; therefore targeting the shedding-sensitive motif in MIC(A) in patients would only generate minimal toxicity. The shedding-sensitive motif in MIC(A) identified herein represents a target to inhibit MIC shedding for clinical applications. Furthermore, it is shown herein that the shedding motif is conserved among different cell lines that were tested. Pooled sera from prostate cancer patients shows similar or identical bands as in these cell lines, indicating that the shedding-sensitive motif is conserved in patients as well.

Example 3

An Six-Amino Acid Motif in the α3 Domain of MICA is the Cancer Therapeutic Target to Inhibit Shedding Here an six-amino acid (6-aa) motif in the α3 domain of MIC was identified that is critical for the interaction of MIC with ERp5 to enable shedding. Mutations in this motif prevented MIC shedding but did not interfere with NKG2D-mediated recognition of MIC. This study identifies the 6-aa motif as a feasible target to inhibit MIC shedding for cancer therapy.

Materials and Methods

Cell Lines

The mouse prostate tumor cell line TRAMP-C2 was grown in DMEM medium supplemented with 10% FCS, 5 μg/ml insulin, 5 μg/ml transferrin, and 5 ng/ml selenium (ITS). The human B cell lymphoma cell line C1R was cultured in RPMI-1460 supplemented with 10% FCS. The Eco-Phoenix and Ampho-Pheonix retrovirus package cell lines were cultured in DMEM medium supplemented with 10% FCS and 25 mM sodium pyruvate. NK-92 cells were maintained in MEM-α media supplemented with 12.5% FCS, 12.5% horse serum, and 1000 U/ml of IL-2.

Overexpressing Human MICA and MICA Mutants in TRAMP-C2 and C1R Cells

The cDNA of wild-type MICA*01 (wtMICA) was kindly provided by Dr. A. Steinle (University of Tübingen, Tübingen, Germany). cDNAs of MICA mutants were generated by recombinant PCR techniques as described (Wu et al., "Obstructing Shedding of the Immunostimulatory MHC Class I Chain-related Gene B Prevents Tumor Formation," *Clin Cancer Res* 15: 632-640 (2009), which is hereby incorporated by reference in its entirety). cDNAs were subcloned into the retroviral vector pBMN-GFP (Orbigen Inc). To overexpress the wtMICA and MICA mutants in TRAMP-C2 and C1R cells, the Eco-Phoenix and Ampho-*Phoenix* package cell lines were transfected with the recombinant plasmids respectively. The recombinant retrovirus from the respective package cells were used to infect TRAMP-C2 and C1R cells.

Flow Cytometry

For detection of cell surface expression of wtMICA or MICA mutants, single cell suspension was incubated with the mAb 6D4.6 (Biolegend) followed by a PE-conjugated secondary reagent. Cells were analyzed with a BD FACScan. Data were analyzed with the CellQuest software (BD Bioscience).

Immunoprecipitation and Western-Blotting

Cells were lysed in Baserga lysis buffer (50 mM HEPES, 150 mM NaCl, 1.5 mM MgCl$_2$, 1 mM EGTA, 1% Triton X-100) with Complete Protease Inhibitors (Roche Applied Science). Cell culture supernatant or clear cell lysate was incubated with the mAb 6D4.6 and ultralink immobilized protein A/G plus (Pierce). Immune complexes were treated with PNGase F to remove oligosaccharide chains, separated by SDS-PAGE, and transferred onto a nitrocellulose membrane. The membrane was blotted with the rabbit anti-human MICA polyclonal Ab H-300 (Santa Cruz Biotechnology) and donkey anti-rabbit-IgG-HRP (Santa Cruz Biotechnology). Proteins were detected with ECL reagents (GE Healthcare).

Co-Immunoprecipitation

To assess the interaction of MICA mutants with ERp5, cells were surface biotinylated with EZ-Link Sulfo-NHS-SS-Biotin (Pierce) and fixed with 10% (w/v) TCA (trichloro acetic acid) for 30 min before lysed in 1% NP-40 lysis buffer containing 50 mM Tris (pH 7.4), 150 mM NaCl, 5 mM EDTA, 40 mM N-ethylmaleimide and Complete Protease Inhibitors (Roche Applied Science). Clear cell lysates were neutralized to pH 7.0 with 1 M Tris buffer (pH 9.5) and incubated with the anti-MIC mAb 6D4.6 and ultralink immobilized protein A/G plus (Pierce). Immune complexes were resolved in SDS-PAGE and transferred onto a nitrocellulose membrane. The membrane was blotted with HRP-Streptavidin (KPL), or the rabbit anti-human MICA polyclonal Ab H-300 (Santa Cruz Biotechnology), or the rabbit anti-ERp5 (also called P5) antibody ab11432 (Abcam). In order to distinguish ERp5 and MICA by molecular mass, MICA was not deglycosylated with PNGase F in this assay.

MICA Shedding Assay

Cells were seeded at the density of $4 \times 10^5$ cells/well in a 6-well plate in complete media overnight and replaced with 1 ml/well serum-free media for 24 h. Supernatant was collected and filtered through an 0.45 μm membrane. Cells were lysed with 1 ml Baserga lysis buffer. The amount of soluble MICA in the supernatant and the amount of MICA in the cell lysates were measured using human MICA DuoSet sandwich ELISA kit (R&D Systems). The degree of shedding is expressed as the ratio of sMICA in the culture supernatant to MICA in cell lysates.

Cytotoxicity Assay

NK-92 cells were used as effector cells. Cytotoxicity assay was performed in triplicates using the standard 4 h 51Cr release assay as previously described (Wu et al., "Obstructing Shedding of the Immunostimulatory MHC Class I Chain-related Gene B Prevents Tumor Formation," *Clin Cancer Res* 15: 632-640 (2009), which is hereby incorporated by reference in its entirety). For blocking the activity of NKG2D receptor, NK cell was incubated with 30 ng/ml of rsMICA (GenWay Biotechnology Inc.) for 1 h prior to being used for cytotoxicity assay.

Purification of Tumor Shedding-Derived sMICA from Cell Culture Supernatant

The mAb 6D4.6 was conjugated to the NHS-activated Sepharose Fast Flow (GE Health care) by following the manufacture's instructions. Cell culture supernatant containing sMICA was filtered through 0.2 μm membrane before loaded onto the antibody conjugated Sepharose Fast Flow column. The column was washed with 50 mM NaOAc (pH 4.5) buffer and sMICA was eluted by 0.1 M citrate buffer (pH 2.5). The elution was neutralized with 1.5 M Tris (pH 8.3) immediately and concentrated by the Biomax PES-5 column (Centricon Plus-20, Millipore).

Tandem Mass-Spectrometry Analysis

Purified sMICA was treated with PNGase F before loading on a 10% SDS-PAGE. After Commassie Blue staining, the sMICA bands were excised, washed with 50 mM $NH_4HCO_3$, dehydrated in acetonitrile (ACN), and vacuum dried. The protein bands were incubated with 6.25 ng/μL of trypsin overnight at room temperature. The peptide digests were analyzed by electrospray ionization in the positive ion mode using the LTQ-Orbitrap (Thermo Fisher). Database search was performed with Phenyx software (GeneBio SA, Geneva, Switzerland) against the human International Protein Index (IPI) database.

Statistical Analysis

Data were analyzes using JMP software. Significance between two comparison groups was determined by student's t-test. $P<0.05$ was considered significant.

Results

Mutation of a 6-aa Motif in the α3 Domain of MIC Prevents Shedding.

Figure 13C:
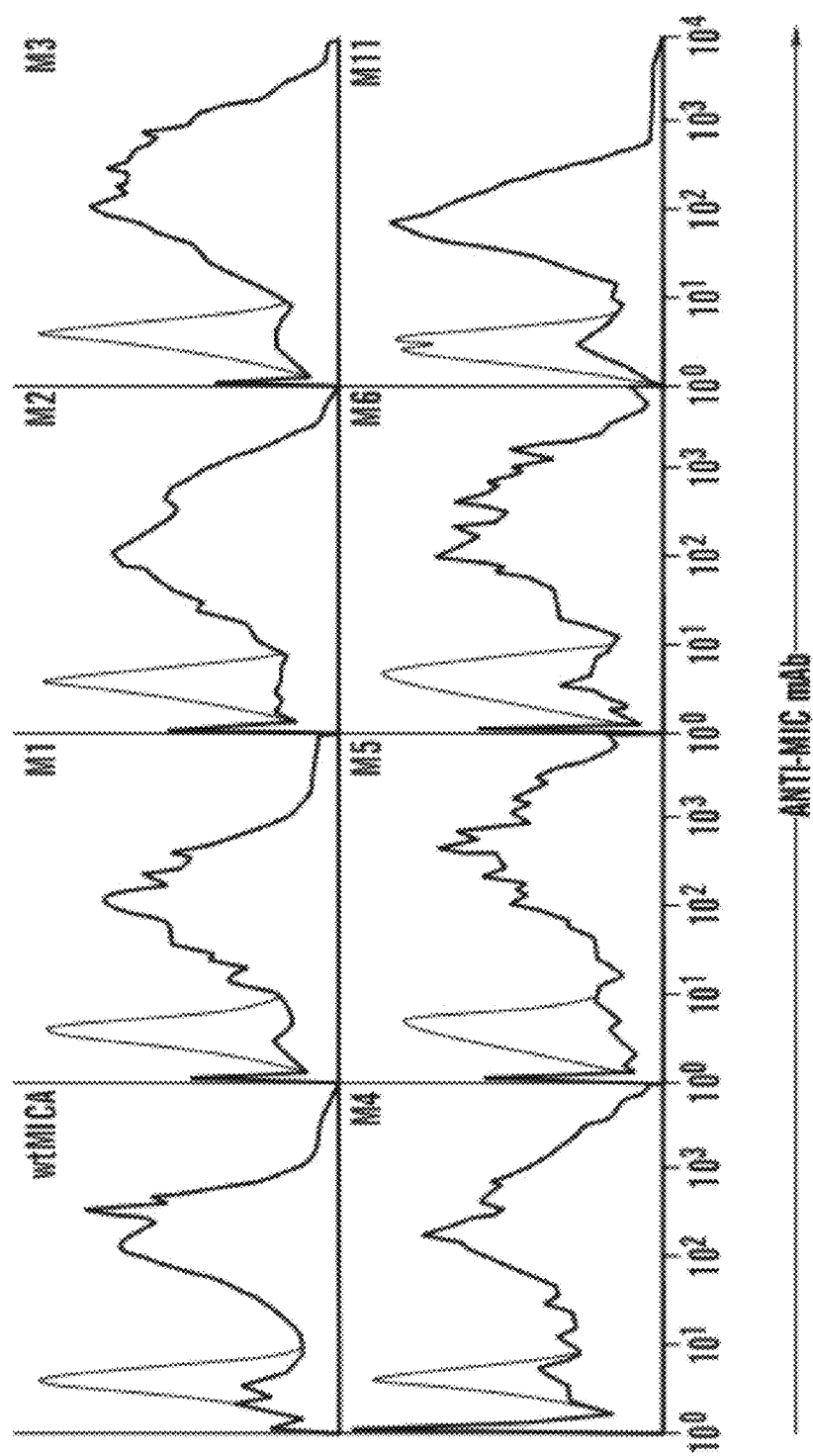
FIG. 13c shows flow cytometry histograms showing surface expression of MICA mutants in TRAMP-C2 cells (filled profiles). Open profiles, negative control TRAMP-C2 cells stained with the mAb 6D4.6. Note that, due to titer differences in retrovirus used for transduction, the histograms showed heterogeneity in the surface expression levels of MICs.

Examples described herein above have indicated that partial mutation of the α3 domain (aa 215 to 274) of MIC prevented MIC shedding (FIG. 13a) (see also Wu et al., "Obstructing Shedding of the Immunostimulatory MHC Class I Chain-related Gene B Prevents Tumor Formation," *Clin Cancer Res* 15: 632-640 (2009), which is hereby incorporated by reference in its entirety). To further define residues or peptide motif(s) critical for shedding of MICA as therapeutic targets, a panel of MICA mutants was constructed within this region by replacing interested residues or motifs with corresponding sequences of HLA-A2 (FIG. 13b). These mutants were stably expressed in the MIC-negative mouse prostate tumor TRAMP-C2 cell lines using a retroviral system. All these mutants were expressed on the cell surface as shown by flow cytometry analyses (FIG. 13c). To assess the shedding nature of these MICA mutants, cell culture supernatant and cell lysates were collected and immune precipitated with the anti-MIC mAb 6D4.6. Immune complexes were analyzed by Western blotting with the anti-MIC polyclonal antibody H-300.

Figure 14A:
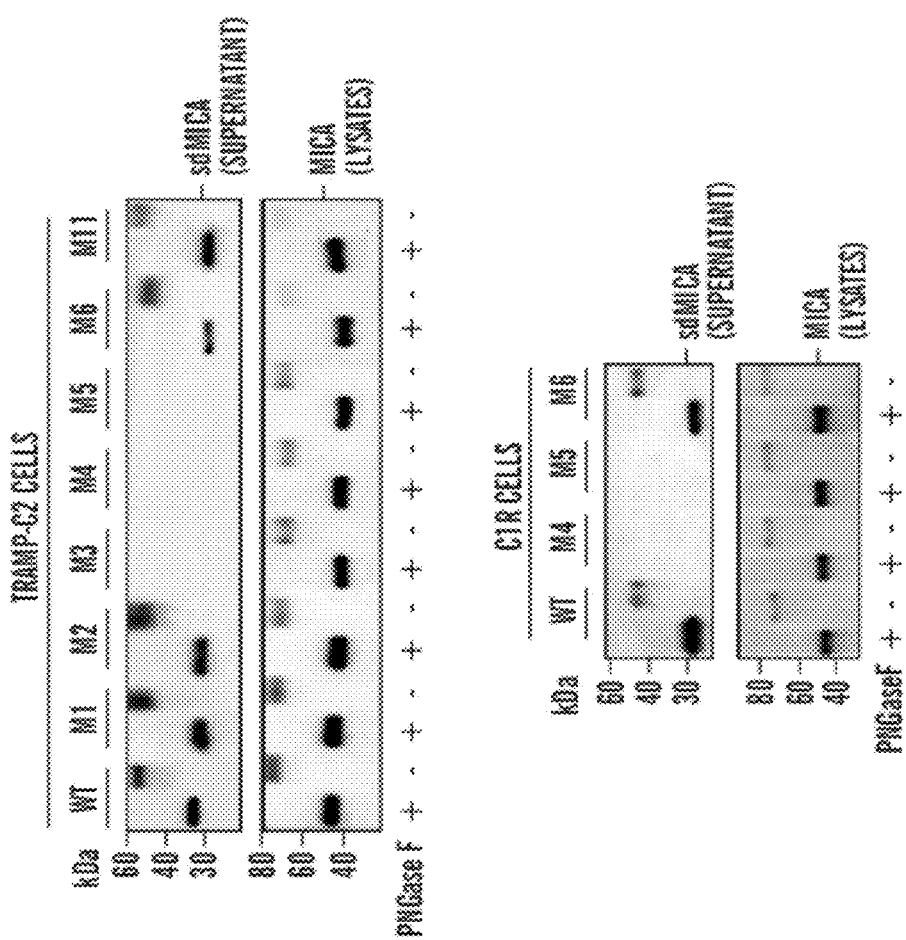
FIG. 14a depicts Western blots showing the shedding resulting sMICA in the culture supernatant (SN) and full-length MICA in the cell lysates (LY). PNGase F was used for deglycosylation.
Figure 17:
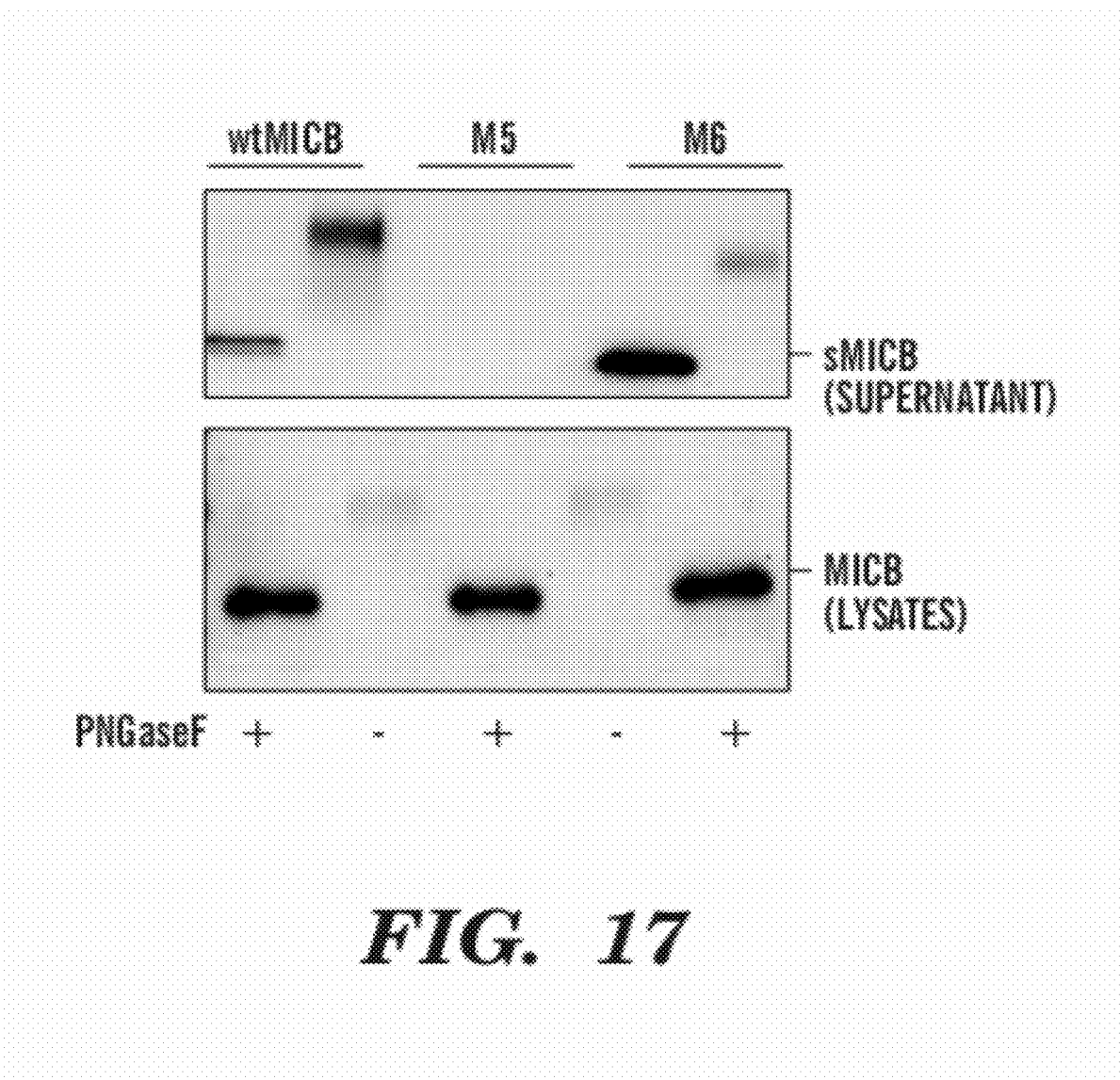
FIG. 17 depicts Western blotting showing that mutation in the 6-aa motif also prevents MICB shedding in TRAMP-C2 cells. MICB mutants M5 and M6 were generated similarly to MICA mutants M5 and M6 respectively. MICB-M5 has mutations in the 6-aa motif of $N^{238}$ to $T^{243}$. Mutant MICB-M6 has mutations in the 5-aa motif of $N^{238}$ to $Q^{242}$. wtMICB, MICB-M5, and MICB-M6 were overexpressed in TRAMP-C2 cells respectively using the retroviral system as described in the material and methods. sMICB from the culture supernatant and MICB from the cell lysates were immunoprecipitated with the anti-MIC mAb 6D4.6. The immunocomplexes were treated with PNGase F, resolved in SDS-PAGE, and immunoblotted with the goat anti-MICB antibody AF1599 (R&D systems).

First, three mutants that cover different regions of aa 218-274: M1 (residues $Q^{218}$ to $D^{236}$), M2 (residues $C^{250}$ to $F^{257}$), and M3 (residues $N^{238}$ to $R^{248}$) were constructed. Only mutant M3 was shown to be shedding-resistant, specifically, no sMICA was seen in the culture supernatant while full-length MIC was detected in the cell lysates (FIG. 14a). This suggests that residues in the region covered by mutant M3 ($N^{238}$ to $R^{248}$) are critical for shedding. Several mutants covering variable lengths of the region $N^{238}$ to $R^{248}$ (M4 to M6, FIG. 13b) were further constructed. Mutant M4 ($N^{238}$ to $V^{245}$) and M5 ($N^{238}$ to $T^{243}$) were shedding-resistant whereas mutant M6 ($N^{238}$ to $Q^{242}$) was not, suggesting that the 6-aa motif covered by M5 ($N^{238}$ to $T^{243}$) is critical for MICA shedding. Mutants M5 and M6 differ in one amino acid $T^{243}$ which was shown not critical for MICA shedding as the mutation of $T^{243}$ to Ala (M7) did not prevent MICA shedding. Together, these results suggest that the 6-aa motif ($N^{238}$ to $T^{243}$) is critical for MICA shedding, possibly by maintaining a biological conformation of MICA. The same results were also observed with similar mutations in the MICB molecule (FIG. 17).

Figure 14B:
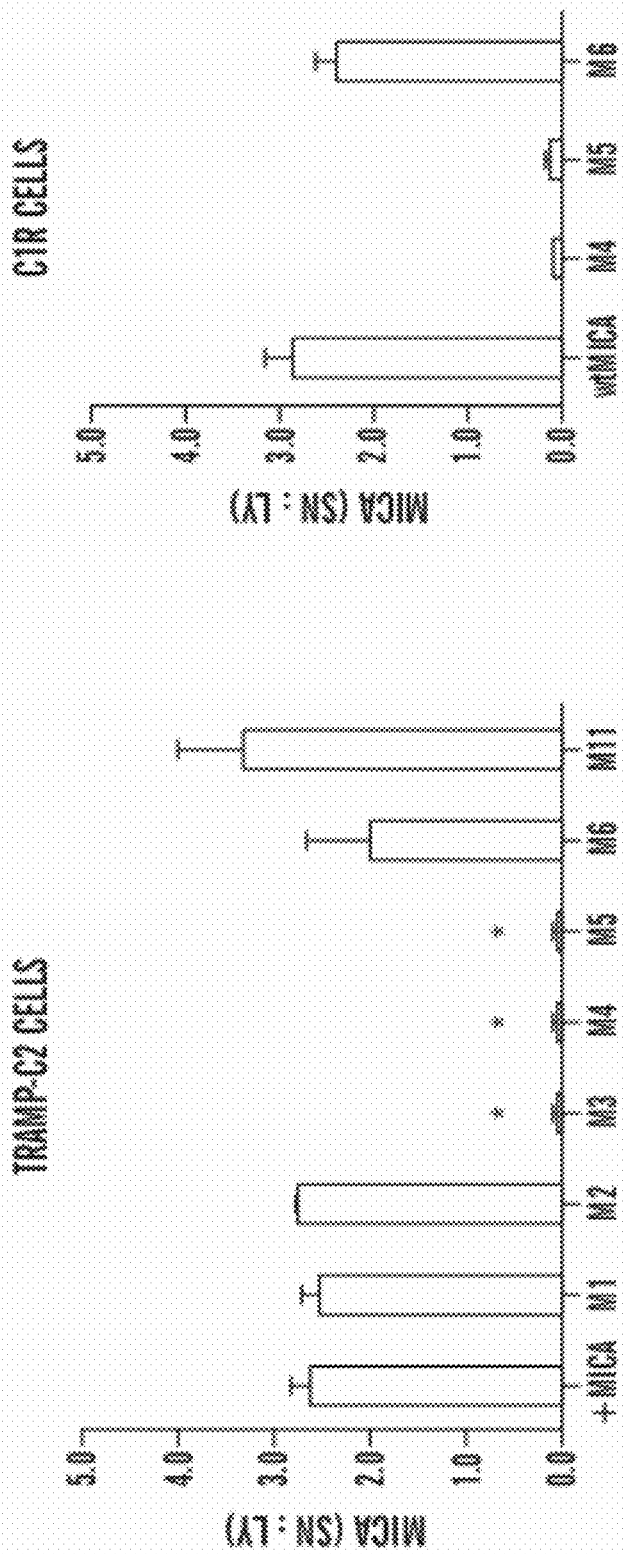
FIG. 14b shows that ELISA quantitatively assayed the degree of shedding of MICA mutants in TRAMP-C2 and C1R cells. (LY). Results represent three independent experiments. *, P<0.001 compared to wtMICA.

The shedding of MICA was evaluated using an ELISA. In a given number of cells, the amount of sMICA released to the culture supernatant and MICA in the cell lysates was measured. The degree of shedding was indicated as ratio of sMICA in the culture supernatant to MICA in the cell lysates. Consistent with western-blot analyses, no shedding was seen in mutants M3, M4, and M5 (FIG. 14b). Together, an 6-aa shedding motif was identified in the α3 domain of MIC that is critical for shedding.

The 6-aa shedding motif is not host-specific and is conserved among all MIC alleles. Whether the MICA mutants M4 and M5 are also shedding-resistant in human tumor cell lines was investigated. wtMICA and mutants M4, M5, and M6 were stably expressed in C1R cell lines using retroviral expression vector. Culture supernatant was collected for immunoprecipitation and Western-blot analyses. The degree of shedding was also assayed by ELISA as described above. As shown in FIGS. 14a and 14b, no shedding was detected with mutant M4 or M5 whereas wtMICA and mutant M6 was shed by C1R cells. These results suggest that the identified 6-aa shedding motif is not host-specific.

Figure 18:
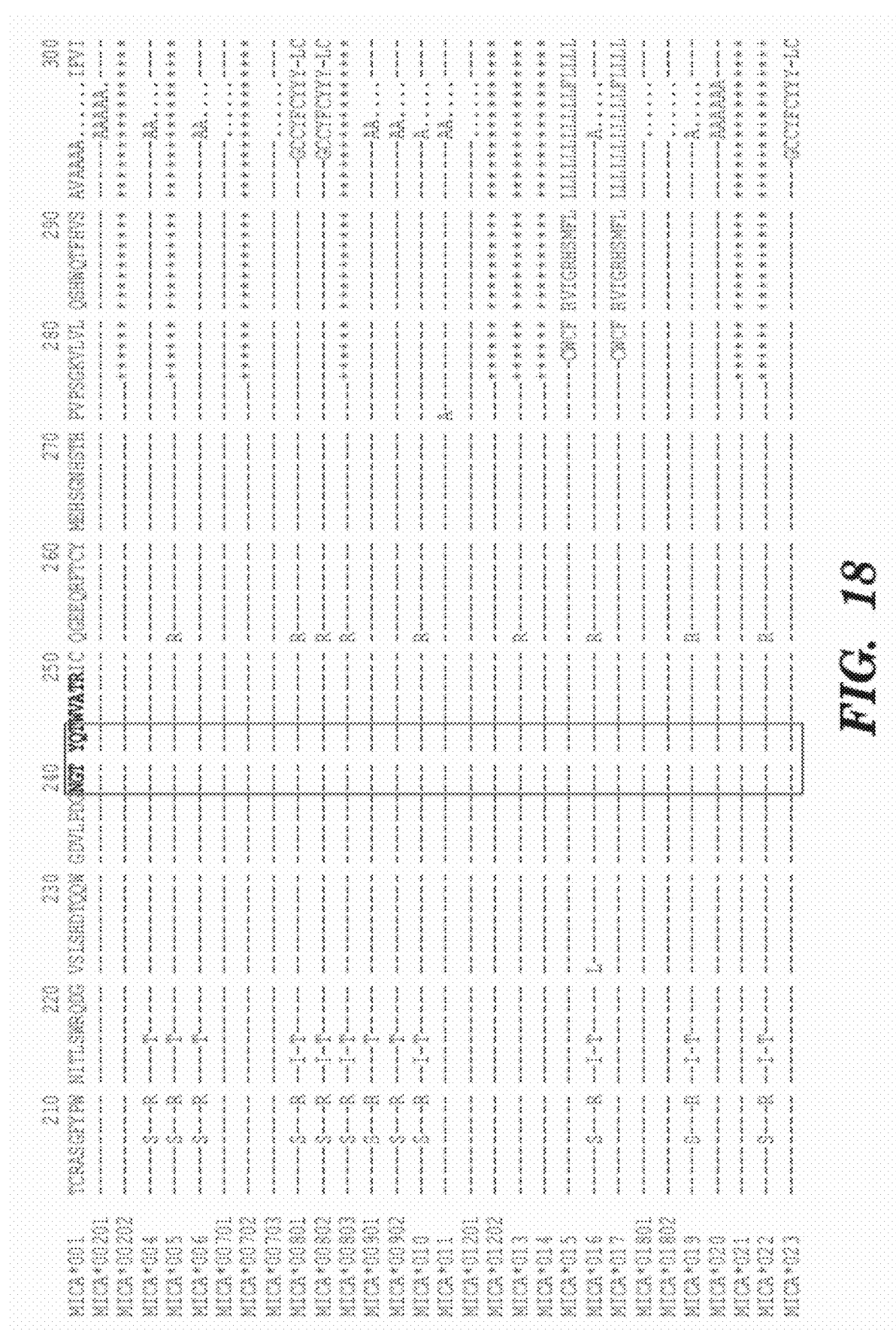
FIG. 18 depicts MICA alleles (SEQ ID NOs 31 to 88). The sequences and alignments were extracted from Bahram et al., "MIC and Other NKG2D Ligands: From None to Too Many," Curr Opin Immunol 17:505-9 (2005), which is hereby incorporated by reference in its entirety. The 11-aa shedding-motif is bold and boxed.
Figure 18:
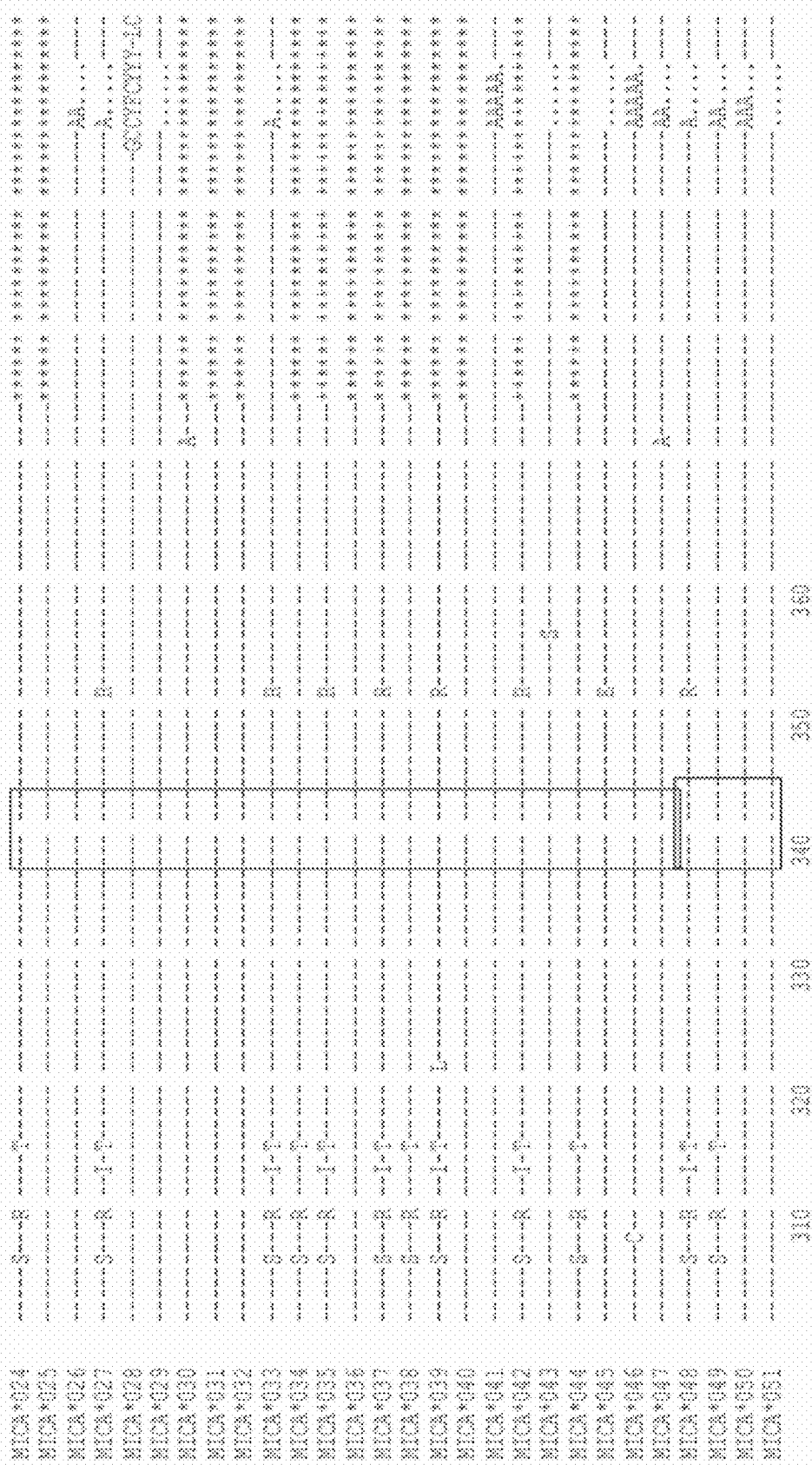
Figure 19:
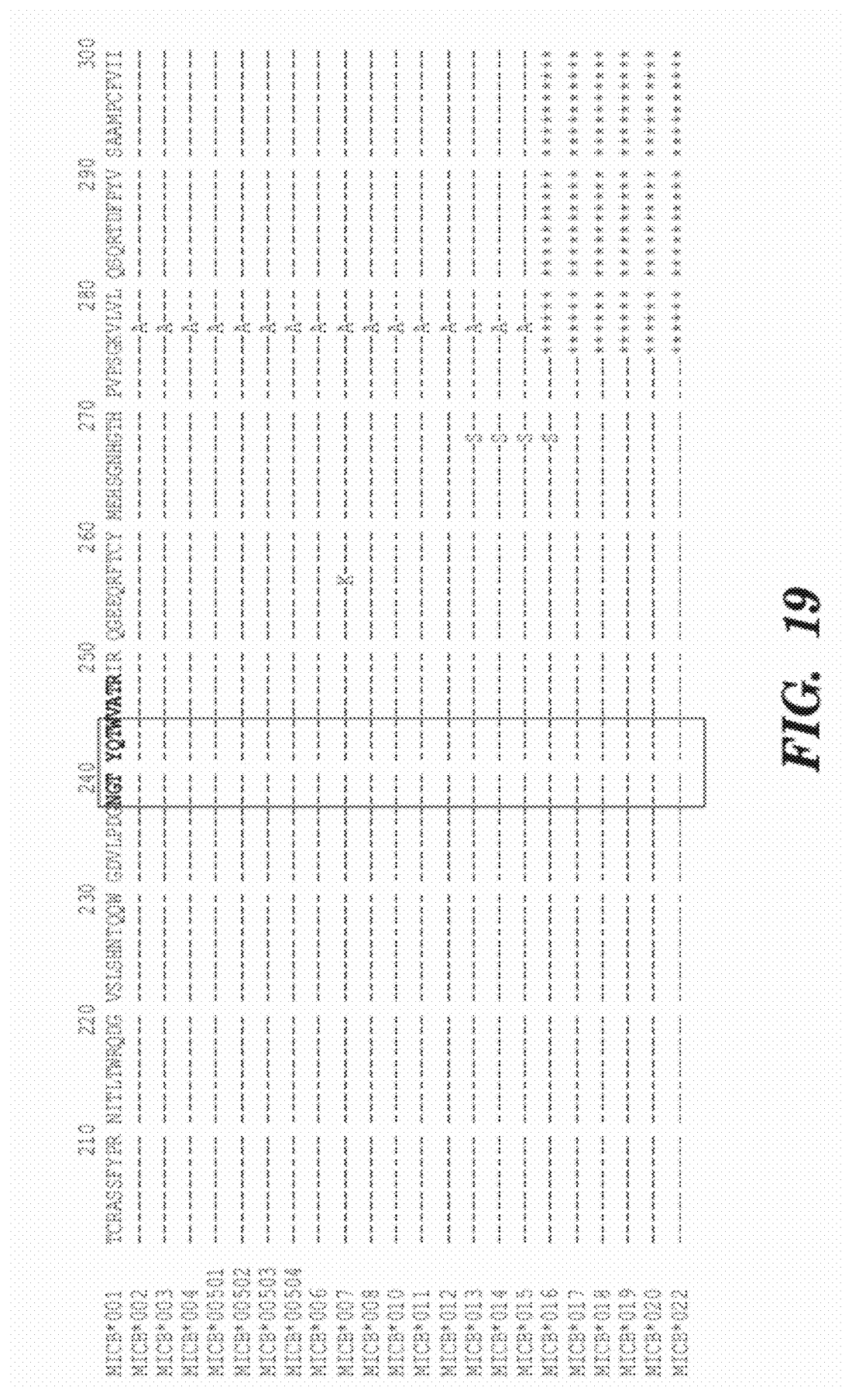

MIC is highly polymorphic. There are now 51 recognized human MICA alleles and at least 22 MICB alleles (Bahram et al., "MIC and Other NKG2D Ligands: From None to Too Many," *Curr Opin Immunol* 17:505-509 (2005), which is hereby incorporated by reference in its entirety). Multiple alignment comparison showed that the sequence of 6-aa shedding-motif, residues $N^{238}$ to $T^{243}$, is identical among all recognized MICA and MICB alleles (FIGS. 18 and 19). These results indicate that the 6-aa shedding motif of MIC is evolutionarily selected to be conserved for a specific function. The term "MIC" as used herein is therefore intended to encompass all alleles of MICA and MICB that include the 6-aa shedding motif identified herein.

The 6-aa shedding motif does not contain MICA cleavage site(s). To address whether the 6-aa shedding motif contains potential MICA shedding site(s), in-gel trypsin digestion and tandem mass spectrometric analyses of sMICA purified from the culture supernatant of TRAMP-C2-MICA cells were performed. In agreement with similar analyses of MICA by other studies (Waldhauer et al., "Tumor-associated MICA is Shed by ADAM Proteases," *Cancer Res* 68 6368-6376 (2008), which is hereby incorporated by reference in its entirety), in three independent experiments, staggered non-tryptic C-terminus of sMICA were identified in the near transmembrane region (FIG. 15a); no non-tryptic C-termini was identified within the 6-aa shedding motif. These results suggest that the 6-aa shedding motif does not contain potential proteolytic MICA cleavage site.

The 6-aa Shedding Motif is Critical for MICA to Interact with ERp5

The mechanisms by which the 6-aa shedding motif is critical for MIC shedding were further pursued. Since the 6-aa motif does not contain MIC cleavage site(s), it may play a regulatory role in MIC shedding. Studies have shown that the protein disulphide isomerase ERp5 is required for enabling MICA shedding through disulphide-bond interaction with the α3 domain of MICA, and presumably with MICB as well (Kaiser et al., "Disulphide-isomerase-enabled Shedding of Tumour-associated NKG2D Ligands," *Nature* 447 482-486 (2007), which is hereby incorporated by reference in its entirety). Since the identified 6-aa shedding motif is located between the two Cysteine (C) residues that form the disulphide bond in the α3 domain of MIC (FIG. 13a), it was investigated whether the 6-aa motif is critical for the physical interaction of MIC with ERp5. To test this, co-immunoprecipitation of MICA with the anti-MIC mAb 6D4.6 from the cell lysates of TRAMP-C2 cells overexpressing wtMICA and the shedding-resistant MICA-M5 was performed. To detect cell surface proteins interacting with MICA, cells were surface biotinylated before being lysed for co-immunoprecipitation. The immunocomplexes were resolved in SDS-PAGE and blotted with HRP-streptavidin, the anti-MICA polyclonal antibody H-300, or the anti-ERp5 polyclonal antibody ab11432. As shown in FIGS. 15b-15d, wtMICA forms a complex with ERp5; on the contrary, the shedding-resistant MICA mutant M5 does not form a complex with ERp5. These results suggest that the 6-aa shedding motif covered by the mutant M5 is critical for MICA, and presumably MICB, to interact with ERp5 to enable shedding.

Mutation of the 6-aa Motif does not Affect the Recognition of MICA by NKG2D

Figure 16A:
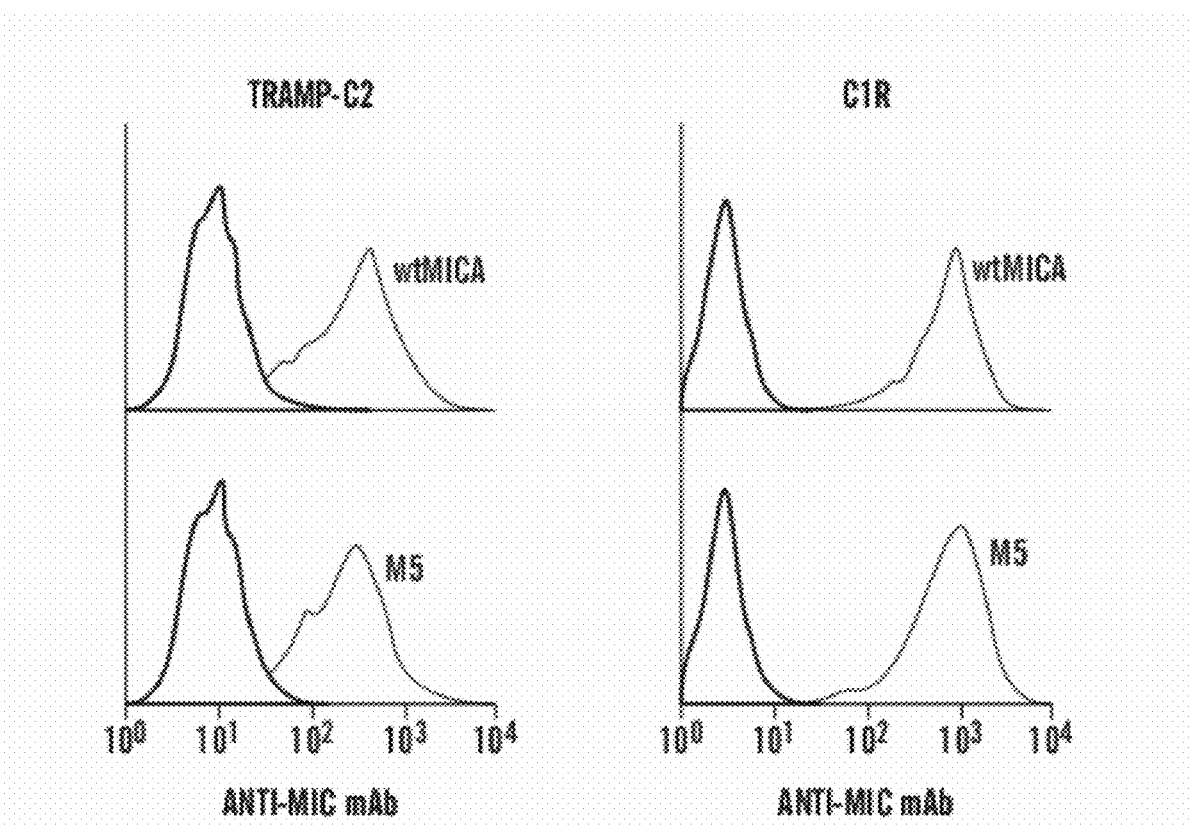
FIG. 16a depicts flow cytometry showing comparable surface wtMICA and MICA mutant M5 expression in isolated pure populations of TRAMP-C2 (TC2) and C1R cells (open profiles). Filled profiles, negative control TC2 or C1R cells stained with the anti-MIC mAb 6D4.6.

Since NKG2D only interacts with the α1α2 ectodomain of MICA (Li et al., "Complex Structure of the Activating Immunoreceptor NKG2D and its MHC Class I-like Ligand MICA," *Nat Immunol* 2 443-451 (2001), which is hereby incorporated by reference in its entirety), mutations in the 6-aa shedding motif (M5) are not likely to impair the recognition of MICA by NKG2D. To confirm this, standard 4 h NK cell cytotoxicity assays were performed. Pure populations of TRAMP-C2 and C1R cells expressing comparable surface levels of wtMICA and the MICA mutant M5 were isolated by repeated flow cytometry sorting (FIG. 16a) and used as target cells for NK-92 cells. The wtMICA and MICA-M5-expressing TRAMP-C2 and C1R cells showed comparable sensitive to the cytotoxicity of NK-92 cells and the sensitivity was inhibited by pre-incubating NK-92 cells with 30 ng/ml of rsMICA. This confirms that disruption of the 6-aa shedding motif does not impair NKG2D-mediated recognition of MICA by NK cells. These results support the conclusion that antibodies or small molecules binding to the 6-aa shedding motif to block the interaction of MICA with ERp5 would not be expected to interfere with the sensitivity of MICA-expressing cells to NK cells.

Of note, although wtMICA was shed by TRAMP-C2 and C1R cells, there was no significant difference (p=0.12 at $LD_{50}$) in sensitivity to NK cells between cells expressing wtMICA and comparable surface levels of mutant M5 in the 4 h in vitro cytotoxicity assay. This observation is consistent with a previous report (Wu et al., "Obstructing Shedding of the Immunostimulatory MHC Class I Chain-related Gene B Prevents Tumor Formation," *Clin Cancer Res* 15 632-640 (2009), which is hereby incorporated by reference in its entirety), showing that in the 4 h in vitro cytotoxicity assay, the killing ability of NK cells was not significantly affected by soluble MIC resulting from target cells shedding. Indeed, in a dynamic shedding study, it is shown that there is little accumulation of sMICA in the culture supernatant within 6 h of culture (FIG. 20).

In conclusion, although MIC was cleaved at multiple sites and potentially by multiple enzymes, an 6-aa motif has been identified that can be an effective target to block the interaction of MIC with ERp5 and thus to inhibit MIC shedding. The fact that the 6-aa motif is conserved among all recognized MIC alleles and that MIC is generally absent in normal tissues makes it feasible to target the 6-aa motif for therapeutic intervention.

One strategy to inhibit MIC shedding for therapy is to block the interaction of ERp5 with MIC. Here, a six-amino acid (6-aa) motif in the α3 domain of MICA has been identified that is critical for interaction of MICA with ERp5. Mutations of this motif inhibited MICA to interact with ERp5 and prevented MICA shedding, but did not interfere with the recognition of MICA by NKG2D. The studies indicate that the 6-aa motif is a feasible target to inhibit MIC shedding for cancer therapy.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A method for treating MIC-positive cancer, the method comprising administering to an individual in need thereof, a therapeutically effective amount of a purified antibody or a polypeptide comprising an antigen-binding fragment thereof that specifically binds to the amino acid sequence NGTYQT (SEQ ID NO: 1) located in the α3 ectodomain of a MIC polypeptide;
  wherein the interaction of the MIC polypeptide and ERp5 is inhibited; and
  whereby the shedding of said MIC polypeptide is inhibited;
  whereby said MIC-positive cancer is treated.

2. A method for increasing sensitivity of a MIC-positive tumor to immune cell-mediated killing, the method comprising administering to an individual having a MIC-positive tumor, a therapeutically effective amount of a purified antibody or a polypeptide comprising an antigen-binding fragment thereof that specifically binds to the amino acid sequence NGTYQT (SEQ ID NO: 1) located in the α3 ectodomain of a MIC polypeptide;
  wherein the interaction of the MIC polypeptide and ERp5 is inhibited; and
  whereby the shedding of said MIC polypeptide is inhibited;
  whereby said MIC-positive tumor is rendered more sensitive to immune cell-mediated killing.

3. A method for reducing MIC shedding by a cancer cell, the method comprising contacting a MIC-positive cancer cell with a purified antibody or a polypeptide comprising an antigen-binding fragment thereof that specifically binds to the amino acid sequence NGTYQT (SEQ ID NO: 1) located in the α3 ectodomain of a MIC polypeptide;
  wherein the interaction of the MIC polypeptide and ERp5 is inhibited; and
  wherein said antibody or polypeptide inhibits shedding of said MIC polypeptide, or a fragment thereof.

4. A purified antibody or a polypeptide comprising an antigen-binding fragment thereof that specifically binds to the amino acid sequence NGTYQT (SEQ ID NO:1) located in the α3 ectodomain of a MIC polypeptide;
  wherein the interaction of the MIC polypeptide with ERp5 is inhibited; and
  wherein binding of said antibody or polypeptide to a MIC polypeptide α3 ectodomain inhibits MIC shedding.

5. The method of claim 3 wherein said cancer cell is a cell of an epithelial cell tumor or a cell of a hematopoietic malignancy.

6. The method of claim 1, wherein said cancer comprises an epithelial cell tumor or a hematopoietic malignancy.

* * * * *